United States Patent
Prinz et al.

(10) Patent No.: US 12,084,651 B2
(45) Date of Patent: *Sep. 10, 2024

(54) SURFACE DISPLAY OF WHOLE ANTIBODIES IN EUKARYOTES

(71) Applicant: Merck Sharp & Dohme LLC, Rahway, NJ (US)

(72) Inventors: Bianka Prinz, Lebanon, NH (US); Natarajan Sethuraman, Hanover, NH (US); Dongxing Zha, Houston, TX (US); Stefan Wildt, Somerville, MA (US); Piotr Bobrowicz, Hanover, NH (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 510 days.

This patent is subject to a terminal disclaimer.

(21) Appl. No.: 17/343,905

(22) Filed: Jun. 10, 2021

(65) Prior Publication Data

US 2021/0317441 A1 Oct. 14, 2021

Related U.S. Application Data

(60) Continuation of application No. 16/150,674, filed on Oct. 3, 2018, now Pat. No. 11,046,951, which is a continuation of application No. 15/007,622, filed on Jan. 27, 2016, now abandoned, which is a division of application No. 13/251,410, filed on Oct. 3, 2011, now Pat. No. 9,260,712, which is a division of application No. 12/489,900, filed on Jun. 23, 2009, now Pat. No. 8,067,339.

(60) Provisional application No. 61/208,583, filed on Feb. 25, 2009, provisional application No. 61/134,331, filed on Jul. 9, 2008.

(51) Int. Cl.
| | |
|---|---|
| C12N 15/10 | (2006.01) |
| C07K 16/00 | (2006.01) |
| C07K 16/28 | (2006.01) |
| C07K 16/32 | (2006.01) |
| G01N 33/68 | (2006.01) |

(52) U.S. Cl.
CPC .......... *C12N 15/1037* (2013.01); *C07K 16/00* (2013.01); *C07K 16/2887* (2013.01); *C07K 16/32* (2013.01); *C12N 15/1034* (2013.01); *G01N 33/6854* (2013.01); *C07K 2319/30* (2013.01)

(58) Field of Classification Search
CPC .................. C12N 15/1037; G01N 33/6854
USPC ............................................. 506/9
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,818,700 A | 4/1989 | Cregg et al. |
| 5,693,762 A | 12/1997 | Queen et al. |
| 5,700,678 A | 12/1997 | Toyoshima et al. |
| 5,733,757 A | 3/1998 | Barbas, III et al. |
| 5,772,245 A | 6/1998 | Muhlhausen |
| 5,843,708 A | 12/1998 | Hardman et al. |
| 5,874,247 A | 2/1999 | Toyoshima et al. |
| 5,985,626 A | 11/1999 | Barbas, III et al. |
| 6,114,147 A | 9/2000 | Frenken et al. |
| 6,180,370 B1 | 1/2001 | Queen et al. |
| 6,300,065 B1 | 10/2001 | Kieke et al. |
| 6,368,839 B1 | 4/2002 | Barbas, III et al. |
| 6,632,927 B2 | 10/2003 | Adair et al. |
| 6,699,658 B1 | 3/2004 | Wittrup et al. |
| 6,872,392 B2 | 3/2005 | Nakamura et al. |
| 6,919,183 B2 | 7/2005 | Fandl et al. |
| 6,949,372 B2 | 9/2005 | Betenbaugh et al. |
| 7,029,872 B2 | 4/2006 | Gerngross |
| 7,105,554 B2 | 9/2006 | Orchard et al. |
| 7,132,273 B1 | 11/2006 | Choi et al. |
| 7,166,423 B1 | 1/2007 | Miltenyi et al. |
| 7,198,921 B2 | 4/2007 | Miura et al. |
| 7,259,007 B2 | 8/2007 | Bobrowicz et al. |
| 7,435,553 B2 | 10/2008 | Fandl et al. |
| 7,479,389 B2 | 1/2009 | Nett et al. |
| 8,067,339 B2 | 11/2011 | Prinz et al. |
| 8,877,686 B2 | 11/2014 | Zha et al. |
| 9,260,712 B2 * | 2/2016 | Prinz .................. G01N 33/6854 |
| 2002/0068325 A1 | 6/2002 | Ng et al. |
| 2003/0186374 A1 | 10/2003 | Hufton et al. |
| 2004/0018590 A1 | 1/2004 | Gerngross et al. |
| 2004/0074458 A1 | 4/2004 | Nakamura et al. |

(Continued)

FOREIGN PATENT DOCUMENTS

| | | |
|---|---|---|
| EP | 0682710 B1 | 4/1981 |
| EP | 0667896 B1 | 10/1993 |

(Continued)

OTHER PUBLICATIONS

Williams et al (Microbial Cell Factories (2015) 14:43).*

(Continued)

*Primary Examiner* — Lynn A Bristol
(74) *Attorney, Agent, or Firm* — John David Reilly; John C. Todaro

(57) ABSTRACT

Methods for display of recombinant whole immunoglobulins or immunoglobulin libraries on the surface of eukaryote host cells, including yeast and filamentous fungi, are described. The methods are useful for screening libraries of recombinant immunoglobulins in eukaryote host cells to identify immunoglobulins that are specific for an antigen of interest.

11 Claims, 22 Drawing Sheets

Specification includes a Sequence Listing.

(56) References Cited

U.S. PATENT DOCUMENTS

| | | |
|---|---|---|
| 2004/0219611 A1 | 11/2004 | Racher |
| 2004/0229306 A1 | 11/2004 | Nett |
| 2004/0230042 A1 | 11/2004 | Hamilton |
| 2005/0170452 A1 | 8/2005 | Wildt et al. |
| 2005/0216958 A1 | 9/2005 | Yamane et al. |
| 2005/0260729 A1 | 11/2005 | Hamilton |
| 2006/0040353 A1 | 2/2006 | Davidson et al. |
| 2006/0141540 A1 | 6/2006 | Miltenyl et al. |
| 2006/0211085 A1 | 9/2006 | Bobrowicz |
| 2006/0286637 A1 | 12/2006 | Hamilton |
| 2007/0020260 A1 | 1/2007 | Presta |
| 2007/0037248 A1 | 2/2007 | Bobrowicz et al. |
| 2007/0072262 A1 | 3/2007 | Nett et al. |
| 2009/0005264 A1 | 1/2009 | Rekestraw et al. |
| 2009/0137416 A1 | 5/2009 | Fandl et al. |
| 2014/0342932 A1 | 11/2014 | Chen et al. |
| 2015/0211000 A1 | 7/2015 | Zha et al. |

FOREIGN PATENT DOCUMENTS

| | | |
|---|---|---|
| EP | 1392859 B1 | 1/2002 |
| EP | 1324040 | 7/2003 |
| EP | 1056883 B1 | 5/2005 |
| EP | 1415158 | 6/2005 |
| EP | 1415158 B1 | 8/2005 |
| WO | WO1994009117 | 4/1994 |
| WO | WO1994018330 | 8/1994 |
| WO | WO1999036569 | 7/1999 |
| WO | 00/42176 | 7/2000 |
| WO | 02/057423 | 7/2002 |
| WO | WO2002057423 A2 | 7/2002 |
| WO | WO2003012449 A2 | 2/2003 |
| WO | 2004/057002 | 7/2004 |
| WO | 2007/061631 | 5/2007 |
| WO | 2007/136865 | 11/2007 |
| WO | 2008/008554 | 1/2008 |
| WO | 2009/036379 | 3/2009 |
| WO | 2009/085135 | 7/2009 |
| WO | 2009/105357 | 8/2009 |

OTHER PUBLICATIONS

Tang et al (Metabolites Aug. 2020; 10(8): 320).*
Zimmer, A., Gruss, P. (1991). Use of Polymerase Chain Reaction (PCR) to Detect Homologous Recombination in Transfected Cell Lines. In: Murray, E.J. (eds) Gene Transfer and Expression Protocols. Methods in Molecular Biology, vol. 7. Humana Press. https://doi.org/10.1385/0-89603-178-0:411.*
Liu et al., Disulfide Bond Structures of IgG Molecules, 2012, mAbs, 4:1, pp. 17-23.
U.S. Appl. No. 16/150,674, filed Oct. 3, 2018.
U.S. Appl. No. 15/007,622, filed Jan. 27, 2016.
U.S. Appl. No. 13/251,410, filed Oct. 3, 2011.
U.S. Appl. No. 12/489,900, filed Jun. 23, 2009.
Berens, "Gene regulation by tetracyclines", Eur. J. Biochem. (2003), vol. 270, pp. 3109-3121.
Bessette, "Rapid isolation of high-affinity protein binding . . . ", Protein Engineering, Design & Selection (2004), vol. 17. pp. 731-739.
Bobrowicz, "Engineering of an artificial glycosylation pathway . . . ", Glycobiology (2004), vol. 14, pp. 757-766.
Bobrowicz, "Isolation of three contiguous genes . . . ", Yeast (1997), vol. 13, pp. 819-828.
Boder, "Yeast surface display for screening . . . ", Nature Biotechnology (1997), vol. 15, pp. 553-557.
Boder, "Directed evolution of antibody fragments . . . ", PNAS (2000), vol. 97, pp. 10701-10705.
Caldas, "Design and synthesis of germline-based heml-humanized single chain . . . ", Protein Engineering (2000), vol. 13, pp. 353-360.
Chiba, "Production of human compatible high mannose-type . . . ", J. Biol. Chem. (1998), vol. 273, pp. 26298-26304.
Choi, "Use of combinatorial genetic libraries . . . ", PNAS (2003), vol. 100, pp. 5022-5027.
Choo, "Dealigning DNA-binding proteins on the surface . . . ", Curr. Opin. in Biotech. (1995), vol. 6, pp. 431-436.
Coloma, "Position effects of variable region carbohydrate", J. of Immunol. (1999), vol. 162, pp. 2162-2170.
Cosano, "Cloning and sequence analysis of the Pichla pastoris . . . ", Yeast (1996), vol. 14, pp. 861-867.
Cox, "Phagocytic signaling strategies: . . . ", Immunology (2001), vol. 13, pp. 339-345.
Daeron, "Fc Receptor biology", Ann. Ref. Immunol. (1997), vol. 15, p. 203-234.
Damasceno, "Cooverexpression of chaparones for enhaanced secretion . . . ", Appl Microbiol. Biotechnol. (2007), vol. 74, pp. 381-389.
Daugherty, "Quantitative analysis of the effect of the mutation . . . ", PNAS (2000), vol. 97, pp. 2029-2034.
De Groot, "Genome-wide identification of fungal . . . ", Yeast (2003), vol. 20, pp. 781-796.
Dirienzo, "The outer membrane proteins of gram-negative . . . ", Ann. Rev. Biochem. (1978), vol. 47, pp. 481-532.
Ellman, "Cominatorial thinking in chemistry . . . ", PNAS (1997), vol. 94, pp. 2779-2782.
Francisco, "Production and fluorescence-activated cell sorting . . . ", PNAS (1993), vol. 90, pp. 10444-10448.
Yamane-Ohnuki, "Establishment of FUT8 knockout Chinese hamster . . . ", Biotech. and Bioeng., vol. 87 (2004), pp. 614-622.
Geoffroy, "A new phage display system . . . ", Gene, vol. 151 (1994), pp. 109-113.
Georgiou, "Display of heterologous proteins . . . ", Nature Biotech. (1997), vol. 15, pp. 29-34.
Hamilton, "Production of complex human . . . ", Science (2003), vol. 301, pp. 1244-1246.
Hamilton, "Humanization of yeast to produce . . . ", Science (2006), vol. 313, pp. 1441-1443.
Heyman, "Feedback regulation by IgG . . . ", Immunology Letters (2003), vol. 88, pp. 157-161.
Holler, "In vitro evolution of a T cell . . . ", PNAS (2000), vol. 97, pp. 5387-5392.
Hoogenboom, "Designing and optimizing library . . . ", Trends in Blotech, (1997), vol. 15, pp. 62-70.
Huo, "Co-expression of human protein . . . ", Protein Exp. and Purif, (2007), vol. 54, pp. 234-239.
Inan, "Enhancement of protein secretion . . . ", Blotech, and Bloeng. (2006), vol. 93, p. 771-778.
Jacobs, "Pichia surface display: . . . ", Biotech. Letters (2008), vol. 30, pp. 2173-2181.
Jacobs, "Pichia surface display: . . . ", Pichia Protein Expression Conference, San Diego, CA (Oct. 8-11, 2006), Abstract T23.
Jeffreris, "Glycosylation of recombinant . . . ", Biotech, Prog. (2005), vol. 21, pp. 11-16.
Kanda, "Comparison of cell lines . . . ", Biotech. and Bloeng. (2006), vol. 94, pp. 680-688.
Kanda, "Comparison of biological activity . . . ", Glycobiology (2006), vol. 17, pp. 104-118.
Keizer-Gunnink, "Accumulation of properly folded human type III . . . ", Matrix Blology (2000), vol. 19, pp. 29-36.
Knappik, "Engineered turns of a recombinant antibody . . . ", Protein Eng. (1995), vol. 8, pp. 81-89.
Kohler, "Continuous cultures of fused cells . . . ", Nature (1975), vol. 256, pp. 495-497.
Ladner, "Constrained peptides as binding entities", Trends in Biotech. (1995), vol. 13, pp. 426-430.
Li, "Optimization of humanlzed IgGs . . . ", Nature Biotech. (2006), vol. 24, p. 210-215.
Lin Cereghino, "New selectable marker/auxotrophic host strain . . . ", Gene (2001), vol. 263, pp. 159-169.
Lowman, "Selecting high-affinity binding proteins . . . ", Biochemistry (1991), vol. 30, pp. 10832-10838.
Maras, "Filamentous fungi as production organisms . . . ", Glycoconjugate Journa (1999), vol. 16, pp. 99-107.
Markland, "Selection for Protease Inhibitors . . . ", Methods in Enzymology (1996), vol. 267, pp. 28-51.

(56) References Cited

OTHER PUBLICATIONS

Marks, "By-passing Immunization: . . . ", J. Mol. Biol. (1991), vol. 222, pp. 581-597.
Matthews, "Substrate phage; selection of protease substrates . . . ", Science (1993), vol. 260, pp. 1113-1117.
Mazor, "Isolation of engineered, full-length antibodies . . . ", Nature Biotech. (2007), vol. 25, pp. 563-565.
Mergler, "Development of a bisphenol A-adsorbing yeast . . . ", Appl. Microbiol. Biotech. (2004), vol. 63, pp. 418-421.
Mille, "Identification of a new family of genes . . . ", J. Biol. Chem. (2008), vol. 283, pp. 0724-9736.
Mottershead, "Baculoviral display of functional scFv . . . ", Biochem. and Biophys. Res. Comm. (2000), vol. 275, pp. 84-90.
Weaver-Feldhaus, "Yeast mating for combinatorial Fab library generation . . . ". FEBS Letters (2004), vol. 664, pp. 24-34.
De Wildt, "Heavy chain CDR3 optimization of a germline encoded . . . ", Protein Engineering (1997), vol. 10, pp. 835-841.
Nett, "Cloning and disruption of the PpURA5 gene . . . ", Yeast (2003), vol. 20, pp. 1279-1290.
Nett, "Cloning and disruption of the Pichla pastoris . . . ", Yeast (2005), vol. 22, pp. 295-304.
Nizard, "Prolonged display or rapid interhalization . . . ", Protein Eng. (2001), vol. 14, pp. 439-446.
Phizicky, "Protein-protein Interactions: . . . ", Microbiol, Rev. (1995), vol. 59, pp. 94-123.
Rakestraw, "A flow cytometric assay for screening . . . ", Biotech, Prog, (2006), vol. 22, pp. 1200-1208.
Ravetch, "Fc receptors", Curr. Opin. In Immunol. (1997), vol. 9, pp. 121-125.
Rehberg. "Specific molecular activities of recombinant . . . ", J. Biol. Chem. (1982), vol. 257, pp. 11497-11502.
Ren, "Display of adenoregulin with a novel Pichla pastoris . . . ", Mol. Blotech. (2007), vol. 35, pp. 103-108.
Riechmann, "Phage display and selection of a site-directed randomized . . . ", Biochemistry (1993), vol. 32, pp. 8848-8855.
Ryckaert, "Fishing for lectins from diverse sequence librarles: . . . ," 191st meeting of the Belgian Society of Biochemistry and Molecular Biology, . . . , Vrije Universiteit Brussel, Belgium (Dec. 2, 2005), Abstract.
Sblattero, "Exploiting recombination In single bacterla . . . ", Nature Blotech. (2000), vol. 18, pp. 75-80.
Stemmer, "Rapid evolution of a protein . . . ", Nature (1994), vol. 370, pp. 389-391.
Stemmer, "DNA shuffling by random fragmentation . . . ", PNAS (1994), vol. 91, pp. 10747-10751.
Streuli, "Target cell specificity of two species of human Interferon-alpha . . . ", PNAS (1981), vol. 78, pp. 2848-2852.
Swers, "Shuffled antibody libraries created by in vivo . . . ", Nucleic Acids Res. (2004), vol. 32, pp. 1-8.
Tanino, "Construction of a Pichla pastoris cell-surface display system . . . ", Biotech. Prog. (2006), vol. 22, pp. 989-993.
Toman. "Production of recombinant human type 1 . . . ", J. Blol. Chem. (2000), vol. 275, pp. 23303-23309.
Ulrich, "Expression studies of catalytic antibodies", PNAS (1995), vol. 92, pp. 11907-11911.
Vad, "Engineering of a Pichla pastoris expression system . . . ", J. of Biotech. (2005), vol. 116, pp. 251-260.
Walker, "Effect of redox environment on the in vitro . . . ", J. Blol. Chem. (1994), vol. 269, pp. 28487-28493.
Wang, "Phage display of proteases . . . ", Methods In Enzymology (1996), vol. 267, pp. 52-68.
Wang, "A new yeast display vector . . . ", Protein Eng., Design & Selection (2005), vol. 18, pp. 337-343.
Waterhouse, "Combinatorial Infection and in vivo recombination: . . . ", Nucleic Acids Res. (1993), vol. 21, pp. 2265-2266.
Wysocki, "The *Saccharomyces cerevisiae* ACR3 gene . . . ", J. Biol. Chem. (1997), vol. 272, pp. 30061-30066.
Wildt, "The humanization of N-glycosylation . . . ", Nature Rev. (2005), vol. 3, pp. 119-128.
Yoshino, "Efficient and stable display of functional proteins . . . ", Appl. and Environ. Microbiol. (2006), vol. 72, pp. 465-471.
Zhang, "Enhanced secretion of heterologous proteins . . . ", Biotech. Prog. (2006), vol. 22, pp. 1090-1095.
Kennard, "GPI-Anchored fusion proteins", Methods in Biotech. (1999), vol. 8, pp. 187-200.
Ward, "The effector functions of immunoglobulins: . . . ", Therapeutic Immunology,(1995), vol. 2, pp. 77-94.
Chao, "Isolating and engineering human antibodies . . . ", Nature Protocols (2006), vol. 1, pp. 755-768.
Accession No. X56180, (Apr. 18, 2005), "P. pastoris HIS4 gene for trifunctional enzyme . . . ", pp. 1-3.
Jiang, et al., Protein Expression and Purification, vol. 76, 2011, pp. 7-14.

* cited by examiner

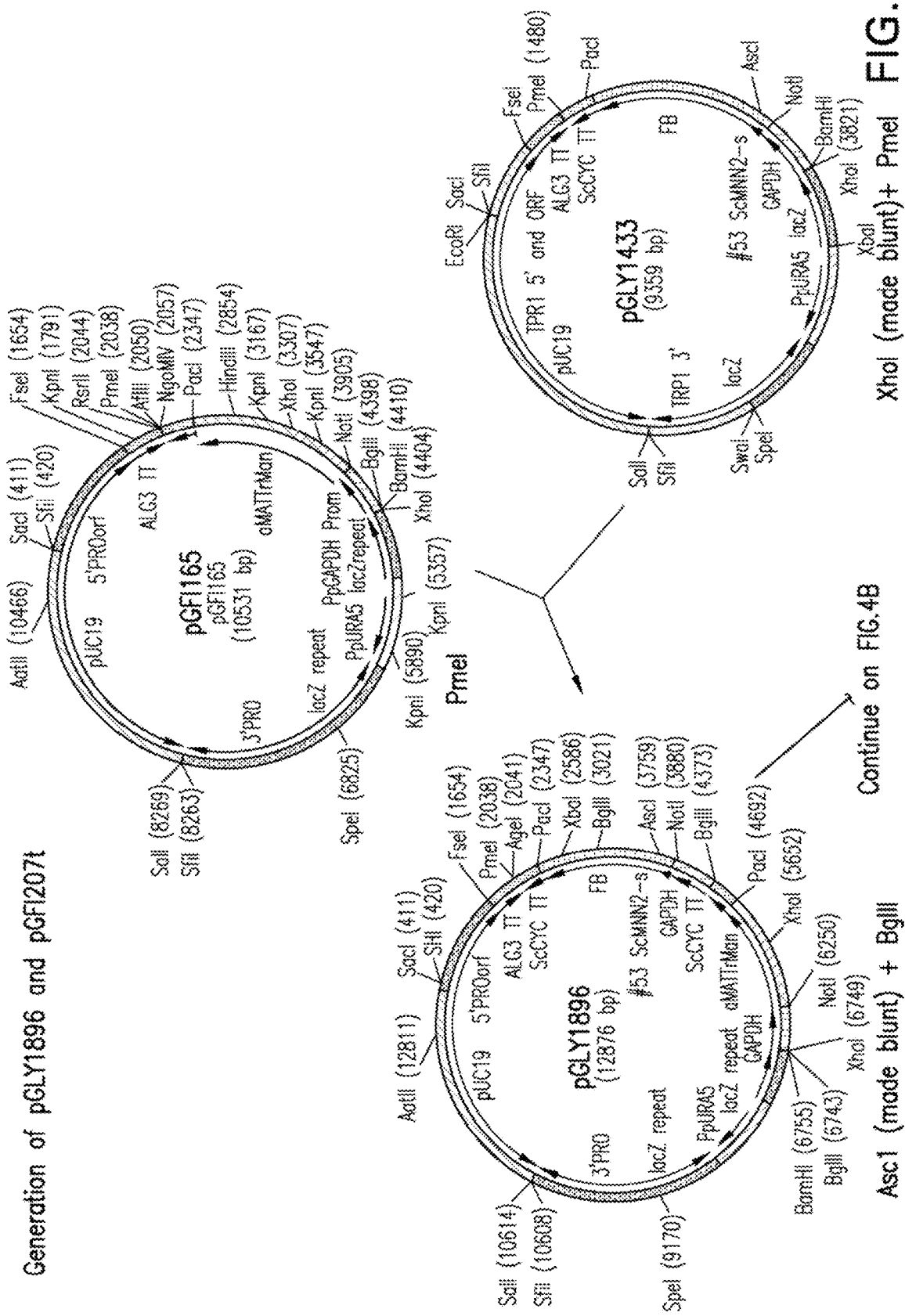

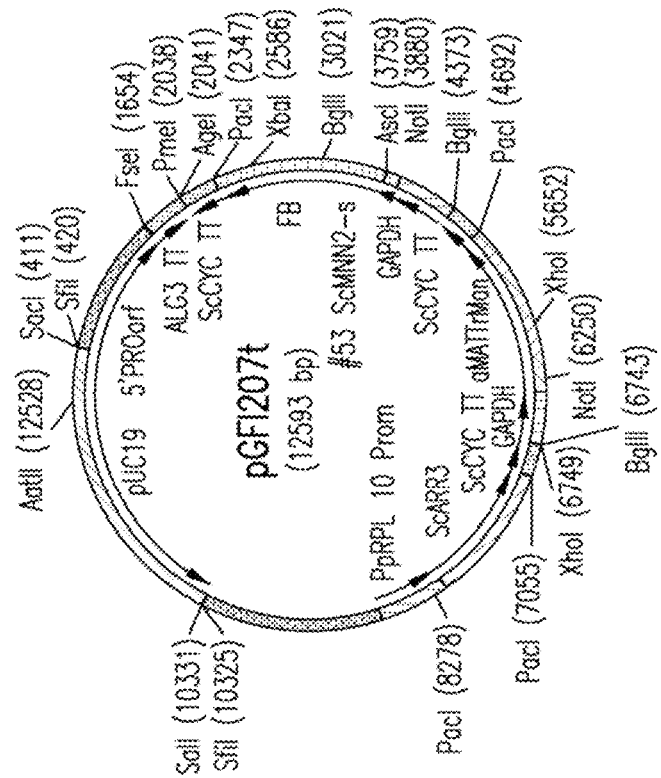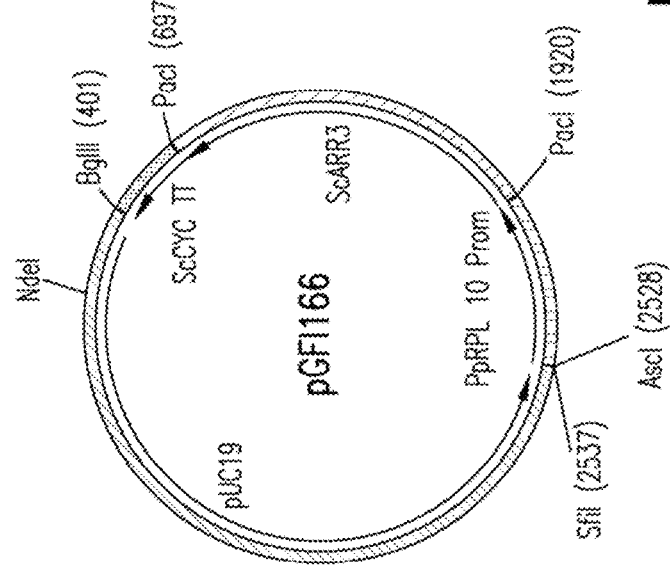
FIG.4B yGLY2696/pGLY4136
10 ng Her2
(prot A/SED1 fusion)

Detection: goat anti-human IgG yGLY2696/pGLY4116
50 ng Her2
(FcRIII/SED1 fusion protein)

Detection: goat anti human IgG

No cell surface display

Glycerol – Methanol

| AOX-protein A anchor | |
|---|---|
| No expression | Expression |

| AOX-antibody | |
|---|---|
| No expression | Expression |

Weak cell surface display

Dextrose – Methanol

| GAPDH-protein A anchor | |
|---|---|
| Expression | Weak expression |

| AOX-antibody | |
|---|---|
| No expression | Expression |

Cell surface display

Glycerol – Dextrose

| GUT1-protein A anchor | |
|---|---|
| Expression | No expression |

| GAPDH-antibody | |
|---|---|
| Weak expression | Expression |

FIG. 17 yGLY5757/pGLY4144
anti-CD20 expressing strain yGLY5434/pGLY4144
anti-Her2 expressing strain

SEQUENCE LISTING

<160> NUMBER OF SEQ ID NOS: 61

<210> SEQ ID NO 1
<211> LENGTH: 30
<212> TYPE: DNA
<213> ORGANISM: Artificial Sequence
<220> FEATURE:
<223> OTHER INFORMATION: PCR primer hPDI/UP1

<400> SEQUENCE: 1
agcgctgacg cccccgagga ggaggaccac                         30

<210> SEQ ID NO 2
<211> LENGTH: 42
<212> TYPE: DNA
<213> ORGANISM: Artificial Sequence
<220> FEATURE:
<223> OTHER INFORMATION: PCR primer hPDI/LP-PacI

<400> SEQUENCE: 2
ccttaattaa ttacagttca tcatgcacag ctttctgatc at           42

<210> SEQ ID NO 3
<211> LENGTH: 47
<212> TYPE: DNA
<213> ORGANISM: Artificial Sequence
<220> FEATURE:
<223> OTHER INFORMATION: PCR primer PB248

<400> SEQUENCE: 3
atgaattcag gccatatcgg ccattgttta ctgtgcgccc acagtag       47

<210> SEQ ID NO 4
<211> LENGTH: 35
<212> TYPE: DNA
<213> ORGANISM: Artificial Sequence
<220> FEATURE:
<223> OTHER INFORMATION: PCR primer PB249

<400> SEQUENCE: 4
atgtttaaac gtgaggatta ctggtgatga aagac                   35

<210> SEQ ID NO 5
<211> LENGTH: 34
<212> TYPE: DNA

```
<213> ORGANISM: Artificial Sequence
<220> FEATURE:
<223> OTHER INFORMATION: PCR primer PB250

<400> SEQUENCE: 5
agactagtct atttggagac attgacggat ccac                              34

<210> SEQ ID NO 6
<211> LENGTH: 46
<212> TYPE: DNA
<213> ORGANISM: Artificial Sequence
<220> FEATURE:
<223> OTHER INFORMATION: PCR primer PB251

<400> SEQUENCE: 6
atctcgagag gccatgcagg ccaaccacaa gatgaatcaa attttg                 46

<210> SEQ ID NO 7
<211> LENGTH: 34
<212> TYPE: DNA
<213> ORGANISM: Artificial Sequence
<220> FEATURE:
<223> OTHER INFORMATION: PCR primer PpPDI/UPi-1

<400> SEQUENCE: 7
ggtgaggttg aggtcccaag tgactatcaa ggtc                              34

<210> SEQ ID NO 8
<211> LENGTH: 34
<212> TYPE: DNA
<213> ORGANISM: Artificial Sequence
<220> FEATURE:
<223> OTHER INFORMATION: PCR primer PpPDI/LPi-1

<400> SEQUENCE: 8
gaccttgata gtcacttggg acctcaacct cacc                              34

<210> SEQ ID NO 9
<211> LENGTH: 34
<212> TYPE: DNA
<213> ORGANISM: Artificial Sequence
<220> FEATURE:
<223> OTHER INFORMATION: PCR primer PpPDI/UPi-2

<400> SEQUENCE: 9
cgccaatgat gaggatgcct cttcaaaggt tgtg                              34

<210> SEQ ID NO 10
<211> LENGTH: 34
<212> TYPE: DNA
<213> ORGANISM: Artificial Sequence
<220> FEATURE:
<223> OTHER INFORMATION: PCR primer PpPDI/LPi-2

<400> SEQUENCE: 10
cacaaccttt gaagaggcat cctcatcatt ggcg                              34

<210> SEQ ID NO 11
<211> LENGTH: 24
<212> TYPE: DNA
<213> ORGANISM: Artificial Sequence
<220> FEATURE:
<223> OTHER INFORMATION: PCR primer PpPDI-5'/UP

<400> SEQUENCE: 11
ggcgattgca ttcgcgactg tatc                                         24
```

<210> SEQ ID NO 12
<211> LENGTH: 23
<212> TYPE: DNA
<213> ORGANISM: Artificial Sequence
<220> FEATURE:
<223> OTHER INFORMATION: PCR primer hPDI-3'/LP

<400> SEQUENCE: 12
cctagagagc ggtggccaag atg        23

<210> SEQ ID NO 13
<211> LENGTH: 25
<212> TYPE: DNA
<213> ORGANISM: Artificial Sequence
<220> FEATURE:
<223> OTHER INFORMATION: PCR primer hPDI/UP

<400> SEQUENCE: 13
gtggccacac caggggggcat ggaac        25

<210> SEQ ID NO 14
<211> LENGTH: 23
<212> TYPE: DNA
<213> ORGANISM: Artificial Sequence
<220> FEATURE:
<223> OTHER INFORMATION: PCR primer hPDI-3'/LP

<400> SEQUENCE: 14
cctagagagc ggtggccaag atg        23

<210> SEQ ID NO 15
<211> LENGTH: 37
<212> TYPE: DNA
<213> ORGANISM: Artificial Sequence
<220> FEATURE:
<223> OTHER INFORMATION: PCR primer hGRP94/UP1

<400> SEQUENCE: 15
agcgctgacg atgaagttga tgtggatggt acagtag        37

<210> SEQ ID NO 16
<211> LENGTH: 38
<212> TYPE: DNA
<213> ORGANISM: Artificial Sequence
<220> FEATURE:
<223> OTHER INFORMATION: PCR primer hGRP94/LP1

<400> SEQUENCE: 16
ggccggcctt acaattcatc atgttcagct gtagattc        38

<210> SEQ ID NO 17
<211> LENGTH: 24
<212> TYPE: DNA
<213> ORGANISM: Artificial Sequence
<220> FEATURE:
<223> OTHER INFORMATION: PCR primer PMT1-KO1

<400> SEQUENCE: 17
tgaacccatc tgtaaataga atgc        24

<210> SEQ ID NO 18
<211> LENGTH: 45
<212> TYPE: DNA
<213> ORGANISM: Artificial Sequence
<220> FEATURE:

<223> OTHER INFORMATION: PCR primer PMT1-KO2

<400> SEQUENCE: 18
gtgtcaccta aatcgtatgt gcccatttac tggaagctgc taacc          45

<210> SEQ ID NO 19
<211> LENGTH: 45
<212> TYPE: DNA
<213> ORGANISM: Artificial Sequence
<220> FEATURE:
<223> OTHER INFORMATION: PCR primer PMT1-KO3

<400> SEQUENCE: 19
ctccctatag tgagtcgtat tcatcattgt actttggtat attgg           45

<210> SEQ ID NO 20
<211> LENGTH: 24
<212> TYPE: DNA
<213> ORGANISM: Artificial Sequence
<220> FEATURE:
<223> OTHER INFORMATION: PCR primer PMT1-KO4

<400> SEQUENCE: 20
tatttgtacc tgcgtcctgt ttgc                                  24

<210> SEQ ID NO 21
<211> LENGTH: 21
<212> TYPE: DNA
<213> ORGANISM: Artificial Sequence
<220> FEATURE:
<223> OTHER INFORMATION: PCR primer PR29

<400> SEQUENCE: 21
cacatacgat ttaggtgaca c                                     21

<210> SEQ ID NO 22
<211> LENGTH: 21
<212> TYPE: DNA
<213> ORGANISM: Artificial Sequence
<220> FEATURE:
<223> OTHER INFORMATION: PCR primer PR32

<400> SEQUENCE: 22
aatacgactc actataggga g                                     21

<210> SEQ ID NO 23
<211> LENGTH: 24
<212> TYPE: DNA
<213> ORGANISM: Artificial Sequence
<220> FEATURE:
<223> OTHER INFORMATION: PCR primer PMT4-KO1

<400> SEQUENCE: 23
tgctctccgc gtgcaataga aact                                  24

<210> SEQ ID NO 24
<211> LENGTH: 45
<212> TYPE: DNA
<213> ORGANISM: Artificial Sequence
<220> FEATURE:
<223> OTHER INFORMATION: PCR primer PMT4-KO2

<400> SEQUENCE: 24
ctccctatag tgagtcgtat tcacagtgta ccatctttca tctcc           45

-continued

<210> SEQ ID NO 25
<211> LENGTH: 45
<212> TYPE: DNA
<213> ORGANISM: Artificial Sequence
<220> FEATURE:
<223> OTHER INFORMATION: PCR primer PMT4-KO3

<400> SEQUENCE: 25
gtgtcaccta aatcgtatgt gaacctaact ctaattcttc aaagc          45

<210> SEQ ID NO 26
<211> LENGTH: 24
<212> TYPE: DNA
<213> ORGANISM: Artificial Sequence
<220> FEATURE:
<223> OTHER INFORMATION: PCR primer PMT4-KO4

<400> SEQUENCE: 26
actagggtat ataattccca aggt                                 24

<210> SEQ ID NO 27
<211> LENGTH: 57
<212> TYPE: DNA
<213> ORGANISM: Artificial Sequence
<220> FEATURE:
<223> OTHER INFORMATION: Pre-pro alpha-mating factor signal peptide
      (ScaMTprepro) (DNA)

<400> SEQUENCE: 27
atgagattcc catccatctt cactgctgtt ttgttcgctg cttcttctgc tttggct    57

<210> SEQ ID NO 28
<211> LENGTH: 19
<212> TYPE: PRT
<213> ORGANISM: Artificial Sequence
<220> FEATURE:
<223> OTHER INFORMATION: Pre-pro alpha-mating factor signal peptide
      (protein)

<400> SEQUENCE: 28

Met Arg Phe Pro Ser Ile Phe Thr Ala Val Leu Phe Ala Ala Ser Ser
1               5                   10                  15

Ala Leu Ala

<210> SEQ ID NO 29
<211> LENGTH: 1353
<212> TYPE: DNA
<213> ORGANISM: Artificial Sequence
<220> FEATURE:
<223> OTHER INFORMATION: Anti-Her2 Heavy chain (VH + IgG1 constant
      region)

<400> SEQUENCE: 29
gaggttcagt tggttgaatc tggaggagga ttggttcaac tggtggttc tttgagattg    60 tcctgtgctg cttccggttt caacatcaag gacacttaca tccactgggt tagacaagct   120
ccaggaaagg gattggagtg ggttgctaga atctacccaa ctaacggtta cacaagatac   180
gctgactccg ttaagggaag attcactatc tctgctgaca cttccaagaa cactgcttac   240
ttgcagatga ctccttgag agctgaggat actgctgttt actactgttc agatggggt    300 ggtgatggtt tctacgctat ggactactgg ggtcaaggaa cttggttac tgtttcctcc    360 gcttctacta aggaccatc tgttttccca ttggctccat cttctaagtc tacttccggt    420
ggtactgctg ctttgggatg tttggttaaa gactacttcc cagagccagt tactgtttct    480

```
tggaactccg gtgctttgac ttctggtgtt cacactttcc cagctgtttt gcaatcttcc      540
ggtttgtact ctttgtcctc cgttgttact gttccatcct cttccttggg tactcagact      600
tacatctgta acgttaacca caagccatcc aacactaagg ttgacaagaa ggttgagcca      660
aagtcctgtg acaagactca tacttgtcca ccatgtccag ctccagaatt gttgggtggt      720
ccttccgttt ttttgttccc accaaagcca aaggacactt tgatgatctc cagaactcca      780
gaggttacat gtgttgttgt tgacgtttct cacgaggacc cagaggttaa gttcaactgg      840
tacgttgacg gtgttgaagt tcacaacgct aagactaagc caagagagga gcagtacaac      900
tccacttaca gagttgtttc cgttttgact gttttgcacc aggattggtt gaacggaaag      960
gagtacaagt gtaaggtttc caacaaggct ttgccagctc aatcgaaaa gactatctcc     1020 aaggctaagg tcaaccaag agagccacag gtttacactt tgccaccatc cagagatgag     1080
ttgactaaga accaggtttc cttgacttgt ttggttaagg gattctaccc atccgacatt     1140
gctgttgaat gggagtctaa cggtcaacca gagaacaact acaagactac tccacctgtt     1200
ttggactctg acggttcctt tttcttgtac tccaagttga ctgttgacaa gtccagatgg     1260
caacagggta acgttttctc ctgttccgtt atgcatgagg ctttgcacaa ccactacact     1320
caaaagtcct tgtctttgtc ccctggtaag taa                                  1353
```

<210> SEQ ID NO 30
<211> LENGTH: 450
<212> TYPE: PRT
<213> ORGANISM: Artificial Sequence
<220> FEATURE:
<223> OTHER INFORMATION: Anti-Her2 Heavy chain (VH + IgG1 constant region)

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 31
<211> LENGTH: 645
<212> TYPE: DNA
<213> ORGANISM: Artificial Sequence
<220> FEATURE:
<223> OTHER INFORMATION: Anti-Her2 light chain (VL + Kappa constant
      region)

<400> SEQUENCE: 31
gacatccaaa tgactcaatc cccatcttct tgtctgctt ccgttggtga cagagttact      60
atcacttgta gagcttccca ggacgttaat actgctgttg cttggtatca acagaagcca    120
ggaaaggctc caaagttgtt gatctactcc gcttccttct tgtactctgg tgttccatcc    180
agattctctg gttccagatc cggtactgac ttcactttga ctatctcctc cttgcaacca    240
gaagatttcg ctacttacta ctgtcagcag cactacacta ctccaccaac tttcggacag    300
ggtactaagg ttgagatcaa agaaactgtt gctgctccat ccgttttcat tttcccacca    360
tccgacgaac agttgaagtc tggtacagct tccgttgttt gtttgttgaa caacttctac    420
ccaagagagg ctaaggttca gtggaaggtt gacaacgctt tgcaatccgg taactcccaa    480
gaatccgtta ctgagcaaga ctctaaggac tccacttact ccttgtcctc cactttgact    540
ttgtccaagg ctgattacga aagcacaag gtttacgctt gtgaggttac acatcaggt    600 ttgtcctccc cagttactaa gtccttcaac agaggagagt gttaa 645

<210> SEQ ID NO 32
<211> LENGTH: 213
<212> TYPE: PRT
<213> ORGANISM: Artificial Sequence
<220> FEATURE:
<223> OTHER INFORMATION: Anti-Her2 light chain (VL + Kappa constant
region)

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 33
<211> LENGTH: 60
<212> TYPE: DNA
<213> ORGANISM: Artificial Sequence
<220> FEATURE:
<223> OTHER INFORMATION: Alpha amylase signal peptide (from Aspergillus
niger -amylase)

<400> SEQUENCE: 33
atggttgctt ggtggtcctt gttcttgtac ggattgcaag ttgctgctcc agctttggct 60

<210> SEQ ID NO 34
<211> LENGTH: 20
<212> TYPE: PRT
<213> ORGANISM: Artificial Sequence
<220> FEATURE:
<223> OTHER INFORMATION: Alpha amylase signal peptide (from Aspergillus
niger -amylase)

<400> SEQUENCE: 34

```
Met Val Ala Trp Trp Ser Leu Phe Leu Tyr Gly Leu Gln Val Ala Ala
1               5                   10                  15

Pro Ala Leu Ala
            20
```

<210> SEQ ID NO 35
<211> LENGTH: 397
<212> TYPE: DNA
<213> ORGANISM: Artificial Sequence
<220> FEATURE:
<223> OTHER INFORMATION: Anti-CD20 Light chain Variable Region

<400> SEQUENCE: 35

```
gagatcgttt tgacacagtc cccagctact ttgtctttgt ccccaggtga aagagctaca    60
ttgtcctgta gagcttccca atctgtttcc tcctacttgg cttggtatca acaaaagcca   120
ggacaggctc caagattgtt gatctacgac gcttccaata gagctactgg tatcccagct   180
agattctctg gttctggttc cggtactgac ttcactttga ctatctcttc cttggaacca   240
gaggacttcg ctgtttacta ctgtcagcag agatccaatt ggccattgac tttcggtggt   300
ggtactaagg ttgagatcaa gcgtacggtt gctgctcctt ccgttttcat tttcccacca   360
tccgacgaac aattgaagtc tggtacccaa ttcgccc                             397
```

<210> SEQ ID NO 36
<211> LENGTH: 132
<212> TYPE: PRT
<213> ORGANISM: Artificial Sequence
<220> FEATURE:
<223> OTHER INFORMATION: Anti-CD20 Light chain Variable Region

<400> SEQUENCE: 36

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Gln Phe Ala
    130
```

<210> SEQ ID NO 37
<211> LENGTH: 445
<212> TYPE: DNA
<213> ORGANISM: Artificial Sequence
<220> FEATURE:
<223> OTHER INFORMATION: Anti-CD20 Heavy chain Variable Region

<400> SEQUENCE: 37

```
gctgttcagc tggttgaatc tggtggtgga ttggttcaac tggtagatc cttgagattg    60
```

-continued

```
tcctgtgctg cttccggttt tactttcggt gactacacta tgcactgggt tagacaagct    120
ccaggaaagg gattggaatg ggtttccggt atttcttgga actccggttc cattggttac    180
gctgattccg ttaagggaag attcactatc tccagagaca acgctaagaa ctccttgtac    240
ttgcagatga actccttgag agctgaggat actgctttgt actactgtac taaggacaac    300
caatacggtt ctggttccac ttacggattg ggagtttggg gacagggaac tttggttact    360
gtctcgagtg cttctactaa gggaccatcc gttttccat ggctccatc ctctaagtct     420 acttccggtg gtacccaatt cgccc                                          445
```

<210> SEQ ID NO 38
<211> LENGTH: 148
<212> TYPE: PRT
<213> ORGANISM: Artificial Sequence
<220> FEATURE:
<223> OTHER INFORMATION: Anti-CD20 Heavy chain Variable Region

<400> SEQUENCE: 38

```
Ala Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Gly Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Asn Gln Tyr Gly Ser Gly Ser Thr Tyr Gly Leu Gly Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Gln Phe Ala
145
```

<210> SEQ ID NO 39
<211> LENGTH: 1476
<212> TYPE: DNA
<213> ORGANISM: Artificial Sequence
<220> FEATURE:
<223> OTHER INFORMATION: Part of human PDI gene

<400> SEQUENCE: 39

```
gacgccccg aggaggagga ccacgtcttg gtgctgcgga aaagcaactt cgcggaggcg    60
ctggcggccc acaagtaccc gccggtggag ttccatgccc cctggtgtgg ccactgcaag    120
gctctggccc ctgagtatgc caaagccgct gggaagctga aggcagaagg ttccgagatc    180
aggttggcca agtggacgc cacggaggag tctgacctag cccagcagta cggcgtgcgc    240
ggctatccca ccatcaagtt cttcaggaat ggagacacgg cttcccccaa ggaatataca    300
gctggcagag aggctgatga catcgtgaac tggctgaaga gcgcacggg cccggctgcc    360 accaccctgc ctgacggcgc agctgcagag tccttggtgg agtccagcga ggtggccgtc    420
```

```
atcggcttct tcaaggacgt ggagtcggac tctgccaagc agttttgca ggcagcagag     480 gccatcgatg acataccatt tgggatcact tccaacagtg acgtgttctc caaataccag     540
ctcgacaaag atggggttgt cctctttaag aagtttgatg aaggccggaa caactttgaa     600
ggggaggtca ccaaggagaa cctgctggac tttatcaaac acaaccagct gccccttgtc     660
atcgagttca ccgagcagac agccccgaag attttggag gtgaaatcaa gactcacatc      720
ctgctgttct tgcccaagag tgtgtctgac tatgacggca aactgagcaa cttcaaaaca     780
gcagccgaga gcttcaaggg caagatcctg ttcatcttca tcgacagcga ccacaccgac     840
aaccagcgca tcctcgagtt ctttggcctg aagaaggaag agtgcccggc cgtgcgcctc     900
atcaccttgg aggaggagat gaccaagtac aagcccgaat cggaggagct gacggcagag     960
aggatcacag agttctgcca ccgcttcctg gagggcaaaa tcaagcccca cctgatgagc    1020
caggagctgc cggaggactg ggacaagcag cctgtcaagg tgcttgttgg gaagaacttt    1080
gaagacgtgg cttttgatga aaaaaaaaac gtctttgtgg agttctatgc cccatggtgt    1140
ggtcactgca aacagttggc tcccatttgg gataaactgg agagacgta caaggaccat     1200 gagaacatcg tcatcgccaa gatggactcg actgccaacg aggtggaggc cgtcaaagtg    1260
cacggcttcc ccacactcgg gttctttcct gccagtgccg acaggacggt cattgattac    1320
aacggggaac gcacgctgga tggttttaag aaattcctag agagcggtgg ccaagatggg    1380
gcaggggatg ttgacgacct cgaggacctc aagaagcag aggagccaga catggaggaa      1440
gacgatgacc agaaagctgt gaaagatgaa ctgtaa                              1476
```

<210> SEQ ID NO 40
<211> LENGTH: 491
<212> TYPE: PRT
<213> ORGANISM: Artificial Sequence
<220> FEATURE:
<223> OTHER INFORMATION: Part of human PDI gene

<400> SEQUENCE: 40

```
Asp Ala Pro Glu Glu Glu Asp His Val Leu Val Leu Arg Lys Ser Asn
1               5                   10                  15

Phe Ala Glu Ala Leu Ala Ala His Lys Tyr Pro Pro Val Glu Phe His
            20                  25                  30

Ala Pro Trp Cys Gly His Cys Lys Ala Leu Ala Pro Glu Tyr Ala Lys
        35                  40                  45

Ala Ala Gly Lys Leu Lys Ala Glu Gly Ser Glu Ile Arg Leu Ala Lys
    50                  55                  60

Val Asp Ala Thr Glu Glu Ser Asp Leu Ala Gln Gln Tyr Gly Val Arg
65                  70                  75                  80

Gly Tyr Pro Thr Ile Lys Phe Phe Arg Asn Gly Asp Thr Ala Ser Pro
                85                  90                  95

Lys Glu Tyr Thr Ala Gly Arg Glu Ala Asp Asp Ile Val Asn Trp Leu
            100                 105                 110

Lys Lys Arg Thr Gly Pro Ala Ala Thr Thr Leu Pro Asp Gly Ala Ala
        115                 120                 125

Ala Glu Ser Leu Val Glu Ser Ser Glu Val Ala Val Ile Gly Phe Phe
    130                 135                 140

Lys Asp Val Glu Ser Asp Ser Ala Lys Gln Phe Leu Gln Ala Ala Glu
145                 150                 155                 160

Ala Ile Asp Asp Ile Pro Phe Gly Ile Thr Ser Asn Ser Asp Val Phe
                165                 170                 175
```

```
Ser Lys Tyr Gln Leu Asp Lys Asp Gly Val Val Leu Phe Lys Lys Phe
            180                 185                 190

Asp Glu Gly Arg Asn Asn Phe Glu Gly Glu Val Thr Lys Glu Asn Leu
        195                 200                 205

Leu Asp Phe Ile Lys His Asn Gln Leu Pro Leu Val Ile Glu Phe Thr
    210                 215                 220

Glu Gln Thr Ala Pro Lys Ile Phe Gly Gly Glu Ile Lys Thr His Ile
225                 230                 235                 240

Leu Leu Phe Leu Pro Lys Ser Val Ser Asp Tyr Asp Gly Lys Leu Ser
                245                 250                 255

Asn Phe Lys Thr Ala Ala Glu Ser Phe Lys Gly Lys Ile Leu Phe Ile
            260                 265                 270

Phe Ile Asp Ser Asp His Thr Asp Asn Gln Arg Ile Leu Glu Phe Phe
        275                 280                 285

Gly Leu Lys Lys Glu Glu Cys Pro Ala Val Arg Leu Ile Thr Leu Glu
    290                 295                 300

Glu Glu Met Thr Lys Tyr Lys Pro Glu Ser Glu Leu Thr Ala Glu
305                 310                 315                 320

Arg Ile Thr Glu Phe Cys His Arg Phe Leu Glu Gly Lys Ile Lys Pro
                325                 330                 335

His Leu Met Ser Gln Glu Leu Pro Glu Asp Trp Lys Gln Pro Val
            340                 345                 350

Lys Val Leu Val Gly Lys Asn Phe Glu Asp Val Ala Phe Asp Glu Lys
        355                 360                 365

Lys Asn Val Phe Val Glu Phe Tyr Ala Pro Trp Cys Gly His Cys Lys
    370                 375                 380

Gln Leu Ala Pro Ile Trp Asp Lys Leu Gly Glu Thr Tyr Lys Asp His
385                 390                 395                 400

Glu Asn Ile Val Ile Ala Lys Met Asp Ser Thr Ala Asn Glu Val Glu
                405                 410                 415

Ala Val Lys Val His Gly Phe Pro Thr Leu Gly Phe Phe Pro Ala Ser
            420                 425                 430

Ala Asp Arg Thr Val Ile Asp Tyr Asn Gly Glu Arg Thr Leu Asp Gly
        435                 440                 445

Phe Lys Lys Phe Leu Glu Ser Gly Gln Asp Gly Ala Gly Asp Val
    450                 455                 460

Asp Asp Leu Glu Asp Leu Glu Glu Ala Glu Glu Pro Asp Met Glu Glu
465                 470                 475                 480

Asp Asp Asp Gln Lys Ala Val His Asp Glu Leu
                485                 490

<210> SEQ ID NO 41
<211> LENGTH: 1554
<212> TYPE: DNA
<213> ORGANISM: Pichia pastoris

<400> SEQUENCE: 41
atgcaattca actggaatat taaaactgtg caagtatttt gtccgctctc cactagca      60 caagcaagtg atcaggaggc tattgctcca gaggactctc atgtcgtcaa attgactgaa    120
gccacttttg agtctttcat caccagtaat cctcacgttt tggcagagtt ttttgcccct    180
tggtgtggtc actgtaagaa gttgggccct gaacttgttt ctgctgccga gatcttaaag    240
gacaatgagc aggttaagat tgctcaaatt gattgtacgg aggagaagga attatgtcaa    300
ggctacgaaa ttaaagggta tcctactttg aaggtgttcc atggtgaggt tgaggtccca    360
```

-continued

```
agtgactatc aaggtcaaag acagagccaa agcattgtca gctatatgct aaagcagagt    420
ttaccccctg tcagtgaaat caatgcaacc aaagatttag acgacacaat cgccgaggca    480
aaagagcccg tgattgtgca agtactaccg gaagatgcat ccaacttgga atctaacacc    540
acattttacg gagttgccgg tactctcaga gagaaattca cttttgtctc cactaagtct    600
actgattatg ccaaaaaata cactagcgac tcgactcctg cctatttgct tgtcagacct    660
ggcgaggaac ctagtgttta ctctggtgag gagttagatg agactcattt ggtgcactgg    720
attgatattg agtccaaacc tctatttgga gacattgacg gatccacctt caaatcatat    780
gctgaagcta acatccccttt agcctactat ttctatgaga acgaagaaca acgtgctgct    840
gctgccgata ttattaaacc ttttgctaaa gagcaacgtg gcaaaattaa ctttgttggc    900
ttagatgccg ttaaattcgg taagcatgcc aagaacttaa acatggatga agagaaactc    960
cctctatttg tcattcatga tttggtgagc aacaagaagt ttggagttcc tcaagaccaa   1020
gaattgacga acaaagatgt gaccgagctg attgagaaat tcatcgcagg agaggcagaa   1080
ccaattgtga aatcagagcc aattccagaa attcaagaag agaaagtctt caagctagtc   1140
ggaaaggccc acgatgaagt tgtcttcgat gaatctaaag atgttctagt caagtactac   1200
gccccttggt gtggtcactg taagagaatg gctcctgctt atgaggaatt ggctactctt   1260
tacgccaatg atgaggatgc ctcttcaaag gttgtgattg caaaacttga tcacactttg   1320
aacgatgtcg acaacgttga tattcaaggt tatcctactt tgatccttta tccagctggt   1380
gataaatcca atcctcaact gtatgatgga tctcgtgacc tagaatcatt ggctgagttt   1440
gtaaaggaga gaggaaccca caaagtggat gccctagcac tcagaccagt cgaggaagaa   1500
aaggaagctg aagaagaagc tgaaagtgag gcagacgctc acgacgagct ttaa         1554
```

<210> SEQ ID NO 42
<211> LENGTH: 517
<212> TYPE: PRT
<213> ORGANISM: Pichia pastoris

<400> SEQUENCE: 42

```
Met Gln Phe Asn Trp Asn Ile Lys Thr Val Ala Ser Ile Leu Ser Ala
1               5                   10                  15

Leu Thr Leu Ala Gln Ala Ser Asp Gln Glu Ala Ile Ala Pro Glu Asp
            20                  25                  30

Ser His Val Val Lys Leu Thr Glu Ala Thr Phe Glu Ser Phe Ile Thr
        35                  40                  45

Ser Asn Pro His Val Leu Ala Glu Phe Phe Ala Pro Trp Cys Gly His
    50                  55                  60

Cys Lys Lys Leu Gly Pro Glu Leu Val Ser Ala Glu Ile Leu Lys
65                  70                  75                  80

Asp Asn Glu Gln Val Lys Ile Ala Gln Ile Asp Cys Thr Glu Lys
                85                  90                  95

Glu Leu Cys Gln Gly Tyr Glu Ile Lys Gly Tyr Pro Thr Leu Lys Val
            100                 105                 110

Phe His Gly Glu Val Glu Val Pro Ser Asp Tyr Gln Gly Gln Arg Gln
        115                 120                 125

Ser Gln Ser Ile Val Ser Tyr Met Leu Lys Gln Ser Leu Pro Pro Val
    130                 135                 140

Ser Glu Ile Asn Ala Thr Lys Asp Leu Asp Asp Thr Ile Ala Glu Ala
145                 150                 155                 160
```

```
Lys Glu Pro Val Ile Val Gln Val Leu Pro Glu Asp Ala Ser Asn Leu
            165                 170                 175

Glu Ser Asn Thr Thr Phe Tyr Gly Val Ala Gly Thr Leu Arg Glu Lys
        180                 185                 190

Phe Thr Phe Val Ser Thr Lys Ser Thr Asp Tyr Ala Lys Lys Tyr Thr
        195                 200                 205

Ser Asp Ser Thr Pro Ala Tyr Leu Leu Val Arg Pro Gly Glu Glu Pro
210                 215                 220

Ser Val Tyr Ser Gly Glu Leu Asp Glu Thr His Leu Val His Trp
225                 230                 235                 240

Ile Asp Ile Glu Ser Lys Pro Leu Phe Gly Asp Ile Asp Gly Ser Thr
                245                 250                 255

Phe Lys Ser Tyr Ala Glu Ala Asn Ile Pro Leu Ala Tyr Tyr Phe Tyr
                260                 265                 270

Glu Asn Glu Glu Gln Arg Ala Ala Ala Asp Ile Ile Lys Pro Phe
        275                 280                 285

Ala Lys Glu Gln Arg Gly Lys Ile Asn Phe Val Gly Leu Asp Ala Val
        290                 295                 300

Lys Phe Gly Lys His Ala Lys Asn Leu Asn Met Asp Glu Glu Lys Leu
305                 310                 315                 320

Pro Leu Phe Val Ile His Asp Leu Val Ser Asn Lys Lys Phe Gly Val
                325                 330                 335

Pro Gln Asp Gln Glu Leu Thr Asn Lys Asp Val Thr Glu Leu Ile Glu
                340                 345                 350

Lys Phe Ile Ala Gly Glu Ala Glu Pro Ile Val Lys Ser Pro Ile
        355                 360                 365

Pro Glu Ile Gln Glu Glu Lys Val Phe Lys Leu Val Gly Lys Ala His
        370                 375                 380

Asp Glu Val Val Phe Asp Glu Ser Lys Asp Val Leu Val Lys Tyr Tyr
385                 390                 395                 400

Ala Pro Trp Cys Gly His Cys Lys Arg Met Ala Pro Ala Tyr Glu Glu
                405                 410                 415

Leu Ala Thr Leu Tyr Ala Asn Asp Glu Asp Ala Ser Ser Lys Val Val
                420                 425                 430

Ile Ala Lys Leu Asp His Thr Leu Asn Asp Val Asp Asn Val Asp Ile
        435                 440                 445

Gln Gly Tyr Pro Thr Leu Ile Leu Tyr Pro Ala Gly Asp Lys Ser Asn
        450                 455                 460

Pro Gln Leu Tyr Asp Gly Ser Arg Asp Leu Glu Ser Leu Ala Glu Phe
465                 470                 475                 480

Val Lys Glu Arg Gly Thr His Lys Val Asp Ala Leu Ala Leu Arg Pro
                485                 490                 495

Val Glu Glu Glu Lys Glu Ala Glu Glu Ala Glu Ser Glu Ala Asp
                500                 505                 510

Ala His Asp Glu Leu
        515

<210> SEQ ID NO 43
<211> LENGTH: 2349
<212> TYPE: DNA
<213> ORGANISM: Artificial Sequence
<220> FEATURE:
<223> OTHER INFORMATION: Part of human GRP94 Gene

<400> SEQUENCE: 43
```

```
gatgatgaag ttgacgttga cggtactgtt gaagaggact tgggaaagtc tagagagggt      60
tccagaactg acgacgaagt tgttcagaga gaggaagagg ctattcagtt ggacggattg     120
aacgcttccc aaatcagaga gttgagagag aagtccgaga agttcgcttt ccaagctgag     180
gttaacagaa tgatgaaatt gattatcaac tccttgtaca agaacaaaga gattttcttg     240
agagagttga tctctaacgc ttctgacgct ttggacaaga tcagattgat ctccttgact     300
gacgaaaacg ctttgtccgg taacgaagag ttgactgtta agatcaagtg tgacaaagag     360
aagaacttgt tgcacgttac tgacactggt gttggaatga ctagagaaga gttggttaag     420
aacttgggta ctatcgctaa gtctggtact tccgagttct tgaacaagat gactgaggct     480
caagaagatg gtcaatccac ttccgagttg attggtcagt tcggtgttgg tttctactcc     540
gctttcttgg ttgctgacaa ggttatcgtt acttccaagc acaacaacga cactcaacac     600
atttgggaat ccgattccaa cgagttctcc gttattgctg acccaagagg taacactttg     660
ggtagaggta ctactatcac tttggttttg aaagaagagg cttccgacta cttggagttg     720
gacactatca agaacttggt taagaagtac tcccagttca tcaacttccc aatctatgtt     780
tggtcctcca agactgagac tgttgaggaa ccaatggaag aagaagaggc tgctaaagaa     840
gagaaagagg aatctgacga cgaggctgct gttgaagaag aggaagaaga aaagaagcca     900
aagactaaga aggttgaaaa gactgtttgg gactgggagc ttatgaacga catcaagcca     960
atttggcaga gaccatccaa agaggttgag gaggacgagt acaaggcttt ctacaagtcc    1020
ttctccaaag aatccgatga cccaatggct tacatccact tcactgctga gggtgaagtt    1080
actttcaagt ccatcttgtt cgttccaact tctgctccaa gaggattgtt cgacgagtac    1140
ggttctaaga agtccgacta catcaaactt tatgttagaa gagttttcat cactgacgac    1200
ttccacgata tgatgccaaa gtacttgaac ttcgttaagg gtgttgttga ttccgatgac    1260
ttgccattga acgtttccag agagactttg cagcagcaca gttgttgaa ggttatcaga    1320 aagaaacttt ttagaaagac tttggacatg atcaagaaga tcgctgacga caagtacaac    1380
gacactttct ggaaagagtt cggaactaac atcaagttgg gtgttattga ggaccactcc    1440
aacagaacta gattggctaa gttgttgaga ttccagtcct ctcatcaccc aactgacatc    1500
acttccttgg accagtacgt tgagagaatg aaagagaagc aggacaaaat ctacttcatg    1560
gctggttcct ctagaaaaga ggctgaatcc tccccattcg ttgagagatt gttgaagaag    1620
ggttacgagg ttatctactt gactgagcca gttgacgagt actgtatcca ggctttgcca    1680
gagtttgacg gaaagagatt ccagaacgtt gctaaagagg tgttaagtt cgacgaatcc    1740 gaaaagacta agaatccag agaggctgtt gagaaagagt tcgagccatt gttgaactgg    1800
atgaaggaca aggctttgaa ggacaagatc gagaaggctg ttgtttccca gagattgact    1860
gaatccccat gtgctttggt tgcttcccaa tacggatgga gtggtaacat ggaaagaatc    1920
atgaaggctc aggcttacca aactggaaag gacatctcca ctaactacta cgcttcccag    1980
aagaaaactt tcgagatcaa cccaagacac ccattgatca gagacatgtt gagaagaatc    2040
aaagaggacg aggacgacaa gactgttttg gatttggctg ttgttttgtt cgagactgct    2100
actttgagat ccggttactt gttgccagac actaaggctt acggtgacag aatcgagaga    2160
atgttgagat tgtccttgaa cattgaccca gacgctaagg ttgaagaaga accagaagaa    2220
gagccagagg aaactgctga agatactact gaggacactg aacaagacga ggacgaagag    2280
atggatgttg gtactgacga gaggaagag acagcaaagg aatccactgc tgaacacgac    2340
gagttgtaa                                                              2349
```

<210> SEQ ID NO 44
<211> LENGTH: 782
<212> TYPE: PRT
<213> ORGANISM: Artificial Sequence
<220> FEATURE:
<223> OTHER INFORMATION: Part of human GRP94 Gene

<400> SEQUENCE: 44

```
Asp Asp Glu Val Asp Val Asp Gly Thr Val Glu Glu Asp Leu Gly Lys
1               5                   10                  15

Ser Arg Glu Gly Ser Arg Thr Asp Asp Glu Val Val Gln Arg Glu Glu
            20                  25                  30

Glu Ala Ile Gln Leu Asp Gly Leu Asn Ala Ser Gln Ile Arg Glu Leu
        35                  40                  45

Arg Glu Lys Ser Glu Lys Phe Ala Phe Gln Ala Glu Val Asn Arg Met
    50                  55                  60

Met Lys Leu Ile Ile Asn Ser Leu Tyr Lys Asn Lys Glu Ile Phe Leu
65                  70                  75                  80

Arg Glu Leu Ile Ser Asn Ala Ser Asp Ala Leu Asp Lys Ile Arg Leu
                85                  90                  95

Ile Ser Leu Thr Asp Glu Asn Ala Leu Ser Gly Asn Glu Glu Leu Thr
            100                 105                 110

Val Lys Ile Lys Cys Asp Lys Glu Lys Asn Leu Leu His Val Thr Asp
        115                 120                 125

Thr Gly Val Gly Met Thr Arg Glu Glu Leu Val Lys Asn Leu Gly Thr
    130                 135                 140

Ile Ala Lys Ser Gly Thr Ser Glu Phe Leu Asn Lys Met Thr Glu Ala
145                 150                 155                 160

Gln Glu Asp Gly Gln Ser Thr Ser Glu Leu Ile Gly Gln Phe Gly Val
                165                 170                 175

Gly Phe Tyr Ser Ala Phe Leu Val Ala Asp Lys Val Ile Val Thr Ser
            180                 185                 190

Lys His Asn Asn Asp Thr Gln His Ile Trp Glu Ser Asp Ser Asn Glu
        195                 200                 205

Phe Ser Val Ile Ala Asp Pro Arg Gly Asn Thr Leu Gly Arg Gly Thr
    210                 215                 220

Thr Ile Thr Leu Val Leu Lys Glu Glu Ala Ser Asp Tyr Leu Glu Leu
225                 230                 235                 240

Asp Thr Ile Lys Asn Leu Val Lys Lys Tyr Ser Gln Phe Ile Asn Phe
                245                 250                 255

Pro Ile Tyr Val Trp Ser Ser Lys Thr Glu Thr Val Glu Glu Pro Met
            260                 265                 270

Glu Glu Glu Glu Ala Ala Lys Glu Lys Glu Glu Ser Asp Asp Glu
        275                 280                 285

Ala Ala Val Glu Glu Glu Glu Glu Lys Lys Pro Lys Thr Lys Lys
    290                 295                 300

Val Glu Lys Thr Val Trp Asp Trp Glu Leu Met Asn Asp Ile Lys Pro
305                 310                 315                 320

Ile Trp Gln Arg Pro Ser Lys Glu Val Glu Asp Gly Tyr Lys Ala
                325                 330                 335

Phe Tyr Lys Ser Phe Ser Lys Glu Ser Asp Asp Pro Met Ala Tyr Ile
            340                 345                 350

His Phe Thr Ala Glu Gly Glu Val Thr Phe Lys Ser Ile Leu Phe Val
        355                 360                 365
```

```
Pro Thr Ser Ala Pro Arg Gly Leu Phe Asp Glu Tyr Gly Ser Lys Lys
    370                 375                 380

Ser Asp Tyr Ile Lys Leu Tyr Val Arg Arg Val Phe Ile Thr Asp Asp
385                 390                 395                 400

Phe His Asp Met Met Pro Lys Tyr Leu Asn Phe Val Lys Gly Val Val
                405                 410                 415

Asp Ser Asp Asp Leu Pro Leu Asn Val Ser Arg Glu Thr Leu Gln Gln
                420                 425                 430

His Lys Leu Leu Lys Val Ile Arg Lys Leu Val Arg Lys Thr Leu
            435                 440                 445

Asp Met Ile Lys Lys Ile Ala Asp Asp Lys Tyr Asn Asp Thr Phe Trp
    450                 455                 460

Lys Glu Phe Gly Thr Asn Ile Lys Leu Gly Val Ile Glu Asp His Ser
465                 470                 475                 480

Asn Arg Thr Arg Leu Ala Lys Leu Leu Arg Phe Gln Ser Ser His His
                485                 490                 495

Pro Thr Asp Ile Thr Ser Leu Asp Gln Tyr Val Glu Arg Met Lys Glu
                500                 505                 510

Lys Gln Asp Lys Ile Tyr Phe Met Ala Gly Ser Ser Arg Lys Glu Ala
            515                 520                 525

Glu Ser Ser Pro Phe Val Glu Arg Leu Leu Lys Lys Gly Tyr Glu Val
530                 535                 540

Ile Tyr Leu Thr Glu Pro Val Asp Glu Tyr Cys Ile Gln Ala Leu Pro
545                 550                 555                 560

Glu Phe Asp Gly Lys Arg Phe Gln Asn Val Ala Lys Glu Gly Val Lys
                565                 570                 575

Phe Asp Glu Ser Glu Lys Thr Lys Glu Ser Arg Glu Ala Val Glu Lys
                580                 585                 590

Glu Phe Glu Pro Leu Leu Asn Trp Met Lys Asp Lys Ala Leu Lys Asp
            595                 600                 605

Lys Ile Glu Lys Ala Val Val Ser Gln Arg Leu Thr Glu Ser Pro Cys
610                 615                 620

Ala Leu Val Ala Ser Gln Tyr Gly Trp Ser Gly Asn Met Glu Arg Ile
625                 630                 635                 640

Met Lys Ala Gln Ala Tyr Gln Thr Gly Lys Asp Ile Ser Thr Asn Tyr
                645                 650                 655

Tyr Ala Ser Gln Lys Lys Thr Phe Glu Ile Asn Pro Arg His Pro Leu
                660                 665                 670

Ile Arg Asp Met Leu Arg Arg Ile Lys Glu Asp Glu Asp Asp Lys Thr
            675                 680                 685

Val Leu Asp Leu Ala Val Val Leu Phe Glu Thr Ala Thr Leu Arg Ser
    690                 695                 700

Gly Tyr Leu Leu Pro Asp Thr Lys Ala Tyr Gly Asp Arg Ile Glu Arg
705                 710                 715                 720

Met Leu Arg Leu Ser Leu Asn Ile Asp Pro Asp Ala Lys Val Glu Glu
                725                 730                 735

Glu Pro Glu Glu Glu Pro Glu Glu Thr Ala Glu Asp Thr Thr Glu Asp
                740                 745                 750

Thr Glu Gln Asp Glu Asp Glu Met Asp Val Gly Thr Asp Glu Glu
            755                 760                 765

Glu Glu Thr Ala Lys Glu Ser Thr Ala Glu His Asp Glu Leu
770                 775                 780
```

<210> SEQ ID NO 45
<211> LENGTH: 1035
<212> TYPE: DNA
<213> ORGANISM: Artificial Sequence
<220> FEATURE:
<223> OTHER INFORMATION: ProteinA fusion protein (apre-5xBD-Htag) as
      EcoRI/SalI fragment, including alpha MF pre signal
      sequence, 5 Fc binding domains, and a HA and 9 x
      HIS tag at the C-terminus

<400> SEQUENCE: 45

```
gaattcgaaa cgatgagatt cccatccatc ttcactgctg ttttgttcgc tgcttcttct      60
gctttggcgg ccgctaatgc tgctcaacac gacgaagctc aacagaacgc tttctaccag     120
gttttgaaca tgccaaactt gaacgctgac cagaggaatg gtttcatcca gtccttgaag     180
gatgacccat ctcaatccgc taacgttttg ggtgaagctc agaagttgaa cgacagtcaa     240
gctcctaagg ctgatgctca acaaaacaac ttcaacaagg accagcaatc tgctttctac     300
gaaatcttga atatgcctaa tttgaacgag gctcagagaa atggattcat tcaatctttg     360
aaagacgacc catcccagtc tactaatgtt ttgggagagg ctaagaaact taatgaaagt     420
caggctccta agctgacaa caactttaac aaagagcagc agaacgcttt ttatgagatt     480
cttaacatgc ctaacttgaa cgaagagcaa agaaacggtt ttattcaatc attgaaggac     540
gatccttcac agtctgctaa cttgttgtcc gaggctaaaa agttgaacga atctcaggct     600
cctaaggctg ataataagtt caacaaagaa caacaaaatg ctttctacga ttttgcac     660 ttgccaaatt tgaatgagga acagagaaac ggttttattc agtcattgaa ggatgaccct     720
tcccaatctg ctaatttgtt ggctgaagct aagaaattga cgacgctca ggctccaaaa     780 gctgataaca aattcaacaa agagcaacag aacgctttct acgaaatctt gcatttgcca     840
aacttgacag aagagcagag aaacggattc attcagtctt tgaaggatga ccctttccgt     900
tccaaagaga ttttggctga ggctaaaaag ttgaatgatg ctcaagctcc aaaaggtggt     960
ggttacccat acgatgttcc agattacgct ggaggtcatc atcatcacca ccatcaccat    1020
catggtggtg tcgac                                                     1035
```

<210> SEQ ID NO 46
<211> LENGTH: 341
<212> TYPE: PRT
<213> ORGANISM: Artificial Sequence
<220> FEATURE:
<223> OTHER INFORMATION: ProteinA fusion protein (apre-5xBD-Htag) as
      EcoRI/SalI fragment, including alpha MF pre signal
      sequence, 5 Fc binding domains, and a HA and 9 x
      HIS tag at the C-terminus

<400> SEQUENCE: 46

Met Arg Phe Pro Ser Ile Phe Thr Ala Val Leu Phe Ala Ala Ser Ser
1               5                   10                  15

Ala Leu Ala Ala Ala Asn Ala Ala Gln His Asp Glu Ala Gln Gln Asn
            20                  25                  30

Ala Phe Tyr Gln Val Leu Asn Met Pro Asn Leu Asn Ala Asp Gln Arg
        35                  40                  45

Asn Gly Phe Ile Gln Ser Leu Lys Asp Asp Pro Ser Gln Ser Ala Asn
    50                  55                  60

Val Leu Gly Glu Ala Gln Lys Leu Asn Asp Ser Gln Ala Pro Lys Ala
65                  70                  75                  80

Asp Ala Gln Gln Asn Asn Phe Asn Lys Asp Gln Gln Ser Ala Phe Tyr
                85                  90                  95

Glu Ile Leu Asn Met Pro Asn Leu Asn Glu Ala Gln Arg Asn Gly Phe
                100                 105                 110

Ile Gln Ser Leu Lys Asp Asp Pro Ser Gln Ser Thr Asn Val Leu Gly
        115                 120                 125

Glu Ala Lys Lys Leu Asn Glu Ser Gln Ala Pro Lys Ala Asp Asn Asn
130                 135                 140

Phe Asn Lys Glu Gln Gln Asn Ala Phe Tyr Glu Ile Leu Asn Met Pro
145                 150                 155                 160

Asn Leu Asn Glu Glu Gln Arg Asn Gly Phe Ile Gln Ser Leu Lys Asp
                165                 170                 175

Asp Pro Ser Gln Ser Ala Asn Leu Leu Ser Glu Ala Lys Lys Leu Asn
            180                 185                 190

Glu Ser Gln Ala Pro Lys Ala Asp Asn Lys Phe Asn Lys Glu Gln Gln
        195                 200                 205

Asn Ala Phe Tyr Glu Ile Leu His Leu Pro Asn Leu Asn Glu Glu Gln
    210                 215                 220

Arg Asn Gly Phe Ile Gln Ser Leu Lys Asp Asp Pro Ser Gln Ser Ala
225                 230                 235                 240

Asn Leu Leu Ala Glu Ala Lys Lys Leu Asn Asp Ala Gln Ala Pro Lys
                245                 250                 255

Ala Asp Asn Lys Phe Asn Lys Glu Gln Gln Asn Ala Phe Tyr Glu Ile
            260                 265                 270

Leu His Leu Pro Asn Leu Thr Glu Glu Gln Arg Asn Gly Phe Ile Gln
        275                 280                 285

Ser Leu Lys Asp Asp Pro Ser Val Ser Lys Glu Ile Leu Ala Glu Ala
    290                 295                 300

Lys Lys Leu Asn Asp Ala Gln Ala Pro Lys Gly Gly Gly Tyr Pro Tyr
305                 310                 315                 320

Asp Val Pro Asp Tyr Ala Gly Gly His His His His His His
                325                 330                 335

His Gly Gly Val Asp
        340

<210> SEQ ID NO 47
<211> LENGTH: 111
<212> TYPE: DNA
<213> ORGANISM: Artificial Sequence
<220> FEATURE:
<223> OTHER INFORMATION: alpha-amylase-ProtAZZ/up primer

<400> SEQUENCE: 47
cggaattcac gatggtcgct tggtggtctt tgtttctgta cggtcttcag gtcgctgcac      60
ctgctttggc ttctggtggt gttactccag ctgctaacgc tgctcaacac g             111

<210> SEQ ID NO 48
<211> LENGTH: 50
<212> TYPE: DNA
<213> ORGANISM: Artificial Sequence
<220> FEATURE:
<223> OTHER INFORMATION: HA-ProtAZZ-XhoIZZ/lp primer

<400> SEQUENCE: 48
gcctcgagag cgtagtctgg aacatcgtat gggtaaccac caccagcatc                50

<210> SEQ ID NO 49
<211> LENGTH: 516
<212> TYPE: DNA

<213> ORGANISM: Artificial Sequence
<220> FEATURE:
<223> OTHER INFORMATION: DNA sequence of the ZZ-domain as EcoRI/XhoI
      fragment with Alpha-amylase sequence

<400> SEQUENCE: 49

```
gaattcacga tggtcgcttg gtggtctttg tttctgtacg gtcttcaggt cgctgcacct     60
gctttggctt ctggtggtgt tactccagct gctaacgctg ctcaacacga tgaagctgtt    120
gacaacaagt tcaacaaaga gcagcagaac gctttctacg agatcttgca cttgccaaac    180
ttgaacgaag agcaaagaaa cgctttcatc cagtccttga aggatgaccc atctcaatcc    240
gctaacttgt tggctgaggc taagaagttg aacgacgctc aagctccaaa ggtcgacaat    300
aagtttaaca agaacaaca aaatgccttc tacgaaattc tgcatctgcc aaccttaac     360 gaggaacaga gaaacgcctt cattcagagt ttgaaggacg atccttccca gtctgctaat    420
ttgcttgccg aagccaagaa attgaatgat gcccaggctc aaaagttga tgctggtggt     480 ggttacccat acgatgttcc agactacgct ctcgag                              516
```

<210> SEQ ID NO 50
<211> LENGTH: 169
<212> TYPE: PRT
<213> ORGANISM: Artificial Sequence
<220> FEATURE:
<223> OTHER INFORMATION: Protein sequence of the ZZ-domain with
      Alpha-amylase leader

<400> SEQUENCE: 50

```
Met Val Ala Trp Trp Ser Leu Phe Leu Tyr Gly Leu Gln Val Ala Ala
1               5                   10                  15

Pro Ala Leu Ala Ser Gly Gly Val Thr Pro Ala Ala Asn Ala Ala Gln
            20                  25                  30

His Asp Glu Ala Val Asp Asn Lys Phe Asn Lys Glu Gln Gln Asn Ala
        35                  40                  45

Phe Tyr Glu Ile Leu His Leu Pro Asn Leu Asn Glu Glu Gln Arg Asn
    50                  55                  60

Ala Phe Ile Gln Ser Leu Lys Asp Asp Pro Ser Gln Ser Ala Asn Leu
65                  70                  75                  80

Leu Ala Glu Ala Lys Lys Leu Asn Asp Ala Gln Ala Pro Lys Val Asp
                85                  90                  95

Asn Lys Phe Asn Lys Glu Gln Gln Asn Ala Phe Tyr Glu Ile Leu His
            100                 105                 110

Leu Pro Asn Leu Asn Glu Glu Gln Arg Asn Ala Phe Ile Gln Ser Leu
        115                 120                 125

Lys Asp Asp Pro Ser Gln Ser Ala Asn Leu Leu Ala Glu Ala Lys Lys
    130                 135                 140

Leu Asn Asp Ala Gln Ala Pro Lys Val Asp Ala Gly Gly Gly Tyr Pro
145                 150                 155                 160

Tyr Asp Val Pro Asp Tyr Ala Leu Glu
                165
```

<210> SEQ ID NO 51
<211> LENGTH: 33
<212> TYPE: DNA
<213> ORGANISM: Artificial Sequence
<220> FEATURE:
<223> OTHER INFORMATION: 5Ecoapp primer

<400> SEQUENCE: 51

```
aacggaattc atgagatttc cttcaatttt tac                              33
```

<210> SEQ ID NO 52
<211> LENGTH: 43
<212> TYPE: DNA
<213> ORGANISM: Artificial Sequence
<220> FEATURE:
<223> OTHER INFORMATION: 3HtagSal primer

<400> SEQUENCE: 52

```
cgatgtcgac gtgatggtga tggtggtgat gatgatgacc acc                   43
```

<210> SEQ ID NO 53
<211> LENGTH: 882
<212> TYPE: DNA
<213> ORGANISM: Artificial Sequence
<220> FEATURE:
<223> OTHER INFORMATION: FcRIII(LF) as EcoRI/SalI fragment

<400> SEQUENCE: 53

```
gaattcatga gatttccttc aattttact gctgttttat tcgcagcatc ctccgcatta    60
gctgctccag tcaacactac aacagaagat gaaacggcac aaattccggc tgaagctgtc  120
atcggttact cagatttaga aggggatttc gatgttgctg ttttgccatt ttccaacagc  180
acaaataacg gttattgtt tataaatact actattgcca gcattgctgc taaagaagaa  240
ggggtatctc tcgagaaaag agctggaatg agaactgagg acttgccaaa ggctgttgtt  300
ttcttggagc acagtggta cagagttttg gagaaggatt ccgttacttt gaagtgtcag  360
ggagcttact ctccagaaga taactccact cagtggttcc acaacgaatc cttgatttct  420
tctcaggctt cctcctactt cattgacgct gctactgttg acgattccgg tgagtacaga  480
tgtcagacta acttgtccac tttgtccgac ccagttcaat ggaggttca catcggttgg  540
ttgttgttgc aagctccaag atgggttttc aaggaggagg acccaattca tttgagatgt  600
cactcttgga gaacactgc tttgcacaaa gttacttact gcagaacgg aaagggtaga  660
aagtatttcc accacaactc cgacttctac atcccaaagg ctactttgaa ggattccggt  720
tcctacttct gtagaggatt gttcggttcc aagaacgttt cttccgagac tgttaacatc  780
actatcactc agggattggc tgtttccact atctcttcct tcttcccacc aggttatcaa  840
ggtggtggtc atcatcatca ccaccatcac catcacgtcg ac                     882
```

<210> SEQ ID NO 54
<211> LENGTH: 292
<212> TYPE: PRT
<213> ORGANISM: Artificial Sequence
<220> FEATURE:
<223> OTHER INFORMATION: FcRIII(LF) with alpha MF pre signal sequence
      and HIS Tag

<400> SEQUENCE: 54

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80
```

```
Ser Leu Glu Lys Arg Ala Gly Met Arg Thr Glu Asp Leu Pro Lys Ala
                85                  90                  95

Val Val Phe Leu Glu Pro Gln Trp Tyr Arg Val Leu Glu Lys Asp Ser
            100                 105                 110

Val Thr Leu Lys Cys Gln Gly Ala Tyr Ser Pro Glu Asp Asn Ser Thr
        115                 120                 125

Gln Trp Phe His Asn Glu Ser Leu Ile Ser Ser Gln Ala Ser Ser Tyr
    130                 135                 140

Phe Ile Asp Ala Ala Thr Val Asp Asp Ser Gly Glu Tyr Arg Cys Gln
145                 150                 155                 160

Thr Asn Leu Ser Thr Leu Ser Asp Pro Val Gln Leu Glu Val His Ile
                165                 170                 175

Gly Trp Leu Leu Leu Gln Ala Pro Arg Trp Val Phe Lys Glu Glu Asp
            180                 185                 190

Pro Ile His Leu Arg Cys His Ser Trp Lys Asn Thr Ala Leu His Lys
        195                 200                 205

Val Thr Tyr Leu Gln Asn Gly Lys Gly Arg Lys Tyr Phe His His Asn
    210                 215                 220

Ser Asp Phe Tyr Ile Pro Lys Ala Thr Leu Lys Asp Ser Gly Ser Tyr
225                 230                 235                 240

Phe Cys Arg Gly Leu Phe Gly Ser Lys Asn Val Ser Ser Glu Thr Val
                245                 250                 255

Asn Ile Thr Ile Thr Gln Gly Leu Ala Val Ser Thr Ile Ser Ser Phe
            260                 265                 270

Phe Pro Pro Gly Tyr Gln Gly Gly His His His His His His
        275                 280                 285

His His Val Asp
    290

<210> SEQ ID NO 55
<211> LENGTH: 1119
<212> TYPE: DNA
<213> ORGANISM: Artificial Sequence
<220> FEATURE:
<223> OTHER INFORMATION: FcRIas EcoRI/SalI fragment:

<400> SEQUENCE: 55
gaattcatga gatttccttc aattttact  gctgttttat tcgcagcatc ctccgcatta      60
gctgctccag tcaacactac aacagaagat gaaacggcac aaattccggc tgaagctgtc     120
atcggttact cagatttaga aggggatttc gatgttgctg ttttgccatt ttccaacagc     180
acaaataacg ggttattgtt tataaatact actattgcca gcattgctgc taagaagaa      240 ggggtatctc tcgagaaaag agctgatact actaaggctg ttatcacttt gcaaccacca     300
tgggtttccg ttttccagga ggagactgtt actttgcact gtgaggtttt gcatttgcct     360
ggttcctctt ccactcagtg gttcttgaac ggtactgcta ctcaaacttc cactccatcc     420
tacagaatta cttccgcttc cgttaacgat tctggtgagt acagatgtca gagaggattg     480
tctggtagat ccgacccaat tcagttggag attcacagag gatggttgtt gttgcaggtt     540 cctccagag  ttttcactga gggtgaacca ttggctttga tgtcacgc  ttggaaggac     600 aagttggttt acaacgtttt gtactacaga aacggaaagg ctttcaagtt cttccactgg     660
aactccaact tgactatctt gaaaactaac atctcccaca acggtactta ccactgttct     720
ggaatgggaa agcacagata cacttccgct ggtatctccg ttactgttaa ggagttgttc     780
```

-continued

```
ccagctccag ttttgaacgc ttccgttact tctccattgt tggagggaaa cttggttact    840
ttgtcctgtg agactaaatt gttgttgcaa agaccaggat tgcagttgta cttctccttc    900
tacatgggtt ccaagacttt gagaggtaga aacacttcct ccgagtacca aatcttgact    960
gctagaagag aggattccgg tttgtactgg tgtgaagctg ctactgagga cggtaacgtt   1020
ttgaagagat ccccagagtt ggagttgcaa gttttgggat tgcaattgcc aactccaggt   1080
ggtggtcatc atcatcacca ccatcaccat cacgtcgac                          1119
```

<210> SEQ ID NO 56
<211> LENGTH: 371
<212> TYPE: PRT
<213> ORGANISM: Artificial Sequence
<220> FEATURE:
<223> OTHER INFORMATION: FcRI with alpha MF pre signal sequence and HIS Tag

<400> SEQUENCE: 56

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Ala Asp Thr Thr Lys Ala Val Ile Thr Leu Gln
                85                  90                  95

Pro Pro Trp Val Ser Val Phe Gln Glu Glu Thr Val Thr Leu His Cys
            100                 105                 110

Glu Val Leu His Leu Pro Gly Ser Ser Ser Thr Gln Trp Phe Leu Asn
        115                 120                 125

Gly Thr Ala Thr Gln Thr Ser Thr Pro Ser Tyr Arg Ile Thr Ser Ala
    130                 135                 140

Ser Val Asn Asp Ser Gly Glu Tyr Arg Cys Gln Arg Gly Leu Ser Gly
145                 150                 155                 160

Arg Ser Asp Pro Ile Gln Leu Glu Ile His Arg Gly Trp Leu Leu Leu
                165                 170                 175

Gln Val Ser Ser Arg Val Phe Thr Glu Gly Glu Pro Leu Ala Leu Arg
            180                 185                 190

Cys His Ala Trp Lys Asp Lys Leu Val Tyr Asn Val Leu Tyr Tyr Arg
        195                 200                 205

Asn Gly Lys Ala Phe Lys Phe Phe His Trp Asn Ser Asn Leu Thr Ile
    210                 215                 220

Leu Lys Thr Asn Ile Ser His Asn Gly Thr Tyr His Cys Ser Gly Met
225                 230                 235                 240

Gly Lys His Arg Tyr Thr Ser Ala Gly Ile Ser Val Thr Val Lys Glu
                245                 250                 255

Leu Phe Pro Ala Pro Val Leu Asn Ala Ser Val Thr Ser Pro Leu Leu
            260                 265                 270

Glu Gly Asn Leu Val Thr Leu Ser Cys Glu Thr Lys Leu Leu Leu Gln
        275                 280                 285

Arg Pro Gly Leu Gln Leu Tyr Phe Ser Phe Tyr Met Gly Ser Lys Thr
    290                 295                 300
```

Leu Arg Gly Arg Asn Thr Ser Ser Glu Tyr Gln Ile Leu Thr Ala Arg
305                 310                 315                 320

Arg Glu Asp Ser Gly Leu Tyr Trp Cys Glu Ala Ala Thr Glu Asp Gly
            325                 330                 335

Asn Val Leu Lys Arg Ser Pro Glu Leu Glu Leu Gln Val Leu Gly Leu
        340                 345                 350

Gln Leu Pro Thr Pro Gly Gly Gly His His His His His His His His
    355                 360                 365

His Val Asp
    370

<210> SEQ ID NO 57
<211> LENGTH: 35
<212> TYPE: DNA
<213> ORGANISM: Artificial Sequence
<220> FEATURE:
<223> OTHER INFORMATION: 5gutBglII primer

<400> SEQUENCE: 57
attgagatct acccaattta gcagcctgca ttctc                          35

<210> SEQ ID NO 58
<211> LENGTH: 36
<212> TYPE: DNA
<213> ORGANISM: Artificial Sequence
<220> FEATURE:
<223> OTHER INFORMATION: 3gutEcoRI primer

<400> SEQUENCE: 58
gtcagaattc atctgtggta tagtgtgaaa aagtag                         36

<210> SEQ ID NO 59
<211> LENGTH: 1010
<212> TYPE: DNA
<213> ORGANISM: Artificial Sequence
<220> FEATURE:
<223> OTHER INFORMATION: Pichia pastoris GUT1 promoter

<400> SEQUENCE: 59
agatctaccc aatttagcag cctgcattct cttgatttta tgggggaaac taacaatagt    60
gttgccttga ttttaagtgg cattgttctt tgaaatcgaa attggggata acgtcatacc   120
gaaaggtaaa caacttcggg gaattgccct ggttaaacat ttattaagcg agataaatag   180
gggatagcga gataggggc ggagaagaag aagggtgtta aattgctgaa atctctcaat    240
ctggaagaaa cggaataaat taactccttc ctgagataat aagatccgac tctgctatga   300
ccccacacgg tactgacctc ggcataccc attggatctg gtgcgaagca acaggtcctg    360
aaacctttat cacgtgtagt agattgacct tccagcaaaa aaaggcatta tatatttgt    420 tgttgaaggg gtgaggggag gtgcaggtgg ttctttatt cgtcttgtag ttaatttcc     480 cggggttgcg gagcgtcaaa agtttgcccg atctgatagc ttgcaagatg ccaccgctta   540
tccaacgcac ttcagagagc ttgccgtaga agaacgtttt cctcgtagt attccagcac    600 ttcatggtga agtcgctatt tcaccgaagg ggggtatta aggttgcgca ccccctcccc    660
acaccccaga atcgtttatt ggctgggttc aatggcgttt gagttagcac attttttcct   720
taaacaccct ccaaacacgg ataaaaatgc atgtgcatcc tgaaactggt agagatgcgt   780
actccgtgct ccgataataa cagtggtgtt ggggttgctg ttagctcacg cactccgttt   840
ttttttcaac cagcaaaatt cgatggggag aaacttgggg tactttgccg actcctccac   900

```
catactggta tataaataat actcgcccac ttttcgtttg ctgcttttat atttcaagga    960
ctgaaaaaga ctcttcttct acttttcac actataccac agatgaattc               1010
```

<210> SEQ ID NO 60
<211> LENGTH: 322
<212> TYPE: PRT
<213> ORGANISM: Artificial Sequence
<220> FEATURE:
<223> OTHER INFORMATION: S. cerevisiae SED1 (without endogenous leader
      sequence

<400> SEQUENCE: 60

```
Val Asp Gln Phe Ser Asn Ser Thr Ser Ala Ser Ser Thr Asp Val Thr
1               5                   10                  15

Ser Ser Ser Ser Ile Ser Thr Ser Ser Gly Ser Val Thr Ile Thr Ser
                20                  25                  30

Ser Glu Ala Pro Glu Ser Asp Asn Gly Thr Ser Thr Ala Ala Pro Thr
            35                  40                  45

Glu Thr Ser Thr Glu Ala Pro Thr Thr Ala Ile Pro Thr Asn Gly Thr
    50                  55                  60

Ser Thr Glu Ala Pro Thr Thr Ala Ile Pro Thr Asn Gly Thr Ser Thr
65                  70                  75                  80

Glu Ala Pro Thr Asp Thr Thr Glu Ala Pro Thr Thr Ala Leu Pro
                85                  90                  95

Thr Asn Gly Thr Ser Thr Glu Ala Pro Thr Asp Thr Thr Glu Ala
                100                 105                 110

Pro Thr Thr Gly Leu Pro Thr Asn Gly Thr Thr Ser Ala Phe Pro Pro
                115                 120                 125

Thr Thr Ser Leu Pro Pro Ser Asn Thr Thr Thr Pro Pro Tyr Asn
130                 135                 140

Pro Ser Thr Asp Tyr Thr Thr Asp Tyr Thr Val Val Thr Glu Tyr Thr
145                 150                 155                 160

Thr Tyr Cys Pro Glu Pro Thr Thr Phe Thr Thr Asn Gly Lys Thr Tyr
                165                 170                 175

Thr Val Thr Glu Pro Thr Thr Leu Thr Ile Thr Asp Cys Pro Cys Thr
                180                 185                 190

Ile Glu Lys Pro Thr Thr Thr Ser Thr Thr Glu Tyr Thr Val Val Thr
                195                 200                 205

Glu Tyr Thr Thr Tyr Cys Pro Glu Pro Thr Thr Phe Thr Thr Asn Gly
    210                 215                 220

Lys Thr Tyr Thr Val Thr Glu Pro Thr Thr Leu Thr Ile Thr Asp Cys
225                 230                 235                 240

Pro Cys Thr Ile Glu Lys Ser Glu Ala Pro Glu Ser Ser Val Pro Val
                245                 250                 255

Thr Glu Ser Lys Gly Thr Thr Lys Glu Thr Gly Val Thr Thr Lys
    260                 265                 270

Gln Thr Thr Ala Asn Pro Ser Leu Thr Val Ser Thr Val Pro Val
    275                 280                 285

Ser Ser Ser Ala Ser Ser His Ser Val Val Ile Asn Ser Asn Gly Ala
    290                 295                 300

Asn Val Val Val Pro Gly Ala Leu Gly Leu Ala Gly Val Ala Met Leu
305                 310                 315                 320

Phe Leu
```

```
<210> SEQ ID NO 61
<211> LENGTH: 969
<212> TYPE: DNA
<213> ORGANISM: Artificial Sequence
<220> FEATURE:
<223> OTHER INFORMATION: S. cerevisiae SED1 (without endogenous leader
      sequence

<400> SEQUENCE: 61
gtcgaccaat tctctaactc tacttccgct tcctctactg acgttacttc ctcctcctct      60
atttctactt cctccggttc cgttactatt acttcctctg aggctccaga atctgacaac     120
ggtacttcta ctgctgctcc aactgaaact tctactgagg ctcctactac tgctattcca     180
actaacggaa cttccacaga ggctccaaca acagctatcc ctacaaacgg tacatccact     240
gaagctccta ctgacactac tacagaagct ccaactactg ctttgcctac taatggtaca     300
tcaacagagg ctcctacaga tacaacaact gaagctccaa caactggatt gccaacaaac     360
ggtactactt ctgctttccc accaactact tccttgccac catccaacac tactactact     420
ccaccataca acccatccac tgactacact actgactaca cagttgttac tgagtacact     480
acttactgtc cagagccaac tactttcaca acaaacggaa agacttacac tgttactgag     540
cctactactt tgactatcac tgactgtcca tgtactatcg agaagccaac tactacttcc     600
actacagagt atactgttgt tacagaatac acaacatatt gtcctgagcc aacaacattc     660
actactaatg gaaaaacata cacagttaca gaaccaacta cattgacaat tacagattgt     720
ccttgtacaa ttgagaagtc cgaggctcct gaatcttctg ttccagttac tgaatccaag     780
ggtactacta ctaaagaaac tggtgttact actaagcaga ctactgctaa cccatccttg     840
actgtttcca ctgttgttcc agtttcttcc tctgcttctt cccactccgt tgttatcaac     900
tccaacggtg ctaacgttgt tgttcctggt gctttgggat tggctggtgt tgctatgttg     960
ttcttgtaa                                                             969
```

SURFACE DISPLAY OF WHOLE ANTIBODIES IN EUKARYOTES

CROSS REFERENCE TO RELATED APPLICATIONS

This patent application is a continuation of U.S. Ser. No. 16/150,674, filed Oct. 3, 2018, which is a continuation of U.S. Ser. No. 15/007,622 filed 27 Jan. 2016, which is a divisional application of U.S. Ser. No. 13/251,410 filed 3 Oct. 2011 and now U.S. Pat. No. 9,260,712, which is a divisional application of U.S. Ser. No. 12/489,900, filed 23 Jun. 2009, and now U.S. Pat. No. 8,067,339, which claims benefit of U.S. Provisional Application No. 61/208,583, filed 25 Feb. 2009 and U.S. Provisional Application No. 61/134,331, filed 9 Jul. 2008, each of which is incorporated herein in its entirety.

REFERENCE TO SEQUENCE LISTING SUBMITTED ELECTRONICALLY

The sequence listing of the present application is submitted electronically via EFS-Web as an ASCII formatted sequence listing with a file name "GFIBIO0034USNP-SEQTXT-9jun.2009.txt", creation date of Jun. 9, 2009, and a size of 61 KB. This sequence listing submitted via EFS-Web is part of the specification and is herein incorporated by reference in its entirety.

BACKGROUND OF THE INVENTION

(1) Field of the Invention

The present invention relates to methods for display of whole immunoglobulins or libraries of immunoglobulins on the surface of eukaryote host cells, including mammalian, plant, yeast, and filamentous fungal cells. The methods are useful for screening libraries of eukaryotic host cells that produce recombinant immunoglobulins to identify particular immunoglobulins with desired properties. The methods are particularly useful for screening immunoglobulin libraries in eukaryote host cells to identify host cells that express an immunoglobulin of interest at high levels, as well as host cells that express immunoglobulins that have high affinity for specific antigens.

(2) Description of Related Art

The discovery of monoclonal antibodies has evolved from hybridoma technology for producing the antibodies to direct selection of antibodies from human cDNA or synthetic DNA libraries. This has been driven in part by the desire to engineer improvements in binding affinity and specificity of the antibodies to improve efficacy of the antibodies. Thus, combinatorial library screening and selection methods have become a common tool for altering the recognition properties of proteins (Ellman et al., Proc. Natl. Acad. Sci. USA 94: 2779-2782 (1997): Phizicky & Fields, Microbiol. Rev. 59: 94-123 (1995)). The ability to construct and screen antibody libraries in vitro promises improved control over the strength and specificity of antibody-antigen interactions.

The most widespread technique for constructing and screening antibody libraries is phage display, whereby the protein of interest is expressed as a polypeptide fusion to a bacteriophage coat protein and subsequently screened by binding to immobilized or soluble biotinylated ligand. Fusions are made most commonly to a minor coat protein, called the gene III protein (pIII), which is present in three to five copies at the tip of the phage. A phage constructed in this way can be considered a compact genetic "unit", possessing both the phenotype (binding activity of the displayed antibody) and genotype (the gene coding for that antibody) in one package. Phage display has been successfully applied to antibodies, DNA binding proteins, protease inhibitors, short peptides, and enzymes (Choo & Klug, Curr. Opin. Biotechnol. 6: 431-436 (1995); Hoogenboom, Trends Biotechnol. 15: 62-70 (1997); Ladner, Trends Biotechnol. 13: 426-430 (1995); Lowman et al., Biochemistry 30: 10832-10838 (1991); Markland et al., Methods Enzymol. 267: 28-51 (1996); Matthews & Wells, Science 260: 1113-1117 (1993); Wang et al., Methods Enzymol. 267: 52-68 (1996)).

Antibodies possessing desirable binding properties are selected by binding to immobilized antigen in a process called "panning". Phage bearing nonspecific antibodies are removed by washing, and then the bound phage are eluted and amplified by infection of $E.$ $coli$. This approach has been applied to generate antibodies against many antigens.

Nevertheless, phage display possesses several shortcomings. Although panning of antibody phage display libraries is a powerful technology, it possesses several intrinsic difficulties that limit its wide-spread successful application. For example, some eukaryotic secreted proteins and cell surface proteins require post-translational modifications such as glycosylation or extensive disulfide isomerization, which are unavailable in bacterial cells. Furthermore, the nature of phage display precludes quantitative and direct discrimination of ligand binding parameters. For example, very high affinity antibodies ($Kd \le 1$ nM) are difficult to isolate by panning, since the elution conditions required to break a very strong antibody-antigen interaction are generally harsh enough (e.g., low pH, high salt) to denature the phage particle sufficiently to render it non-infective.

Additionally, the requirement for physical immobilization of an antigen to a solid surface produces many artifactual difficulties. For example, high antigen surface density introduces avidity effects which mask true affinity. Also, physical tethering reduces the translational and rotational entropy of the antigen, resulting in a smaller DS upon antibody binding and a resultant overestimate of binding affinity relative to that for soluble antigen and large effects from variability in mixing and washing procedures lead to difficulties with reproducibility. Furthermore, the presence of only one to a few antibodies per phage particle introduces substantial stochastic variation, and discrimination between antibodies of similar affinity becomes impossible. For example, affinity differences of six-fold or greater are often required for efficient discrimination (Riechmann & Weill, Biochem. 32: 8848-55 (1993)). Finally, populations can be overtaken by more rapidly growing wild-type phage. In particular, since pIII is involved directly in the phage life cycle, the presence of some antibodies or bound antigens will prevent or retard amplification of the associated phage.

Additional bacterial cell surface display methods have been developed (Francisco, et al., Proc. Natl. Acad. Sci. USA 90: 10444-10448 (1993); Georgiou et al., Nat. Biotechnol. 15: 29-34 (1997)). However, use of a prokaryotic expression system occasionally introduces unpredictable expression biases (Knappik & Pluckthun, Prot. Eng. 8: 81-89 (1995); Ulrich et al., Proc. Natl. Acad. Sci. USA 92: 11907-11911 (1995); Walker & Gilbert, J. Biol. Chem 269: 28487-28493 (1994)) and bacterial capsular polysaccharide layers present a diffusion barrier that restricts such systems to small molecule ligands (Roberts, Annu. Rev. Microbiol. 50: 285-315 (1996)). $E.$ $coli$ possesses a lipopolysaccharide layer or capsule that may interfere sterically with macromolecular binding reactions. In fact, a presumed physiological function of the bacterial capsule is restriction of macromolecular diffusion to the cell membrane, in order to shield the cell from the immune system (DiRienzo et al., Ann. Rev. Biochem. 47: 481-532, (1978)). Since the periplasm of E. coli has not evolved as a compartment for the folding and assembly of antibody fragments, expression of antibodies in E. coli has typically been very clone dependent, with some clones expressing well and others not at all. Such variability introduces concerns about equivalent representation of all possible sequences in an antibody library expressed on the surface of E. coli. Moreover, phage display does not allow some important posttranslational modifications such as glycosylation that can affect specificity or affinity of the antibody. About a third of circulating monoclonal antibodies contain one or more N-linked glycans in the variable regions. In some cases it is believed that these N-glycans in the variable region may play a significant role in antibody function.

The efficient production of monoclonal antibody therapeutics would be facilitated by the development of alternative test systems that utilize lower eukaryotic cells, such as yeast cells. The structural similarities between B-cells displaying antibodies and yeast cells displaying antibodies provide a closer analogy to in vivo affinity maturation than is available with filamentous phage. In particular, because lower eukaryotic cells are able to produce glycosylated proteins, whereas filamentous phage cannot, monoclonal antibodies produced in lower eukaryotic host cells are more likely to exhibit similar activity in humans and other mammals as they do in test systems which utilize lower eukaryotic host cells.

Moreover, the ease of growth culture and facility of genetic manipulation available with yeast will enable large populations to be mutagenized and screened rapidly. By contrast with conditions in the mammalian body, the physicochemical conditions of binding and selection can be altered for a yeast culture within a broad range of pH, temperature, and ionic strength to provide additional degrees of freedom in antibody engineering experiments. The development of yeast surface display system for screening combinatorial protein libraries has been described.

U.S. Pat. Nos. 6,300,065 and 6,699,658 describe the development of a yeast surface display system for screening combinatorial antibody libraries and a screen based on antibody-antigen dissociation kinetics. The system relies on transfecting yeast with vectors that express an antibody or antibody fragment fused to a yeast cell wall protein, using mutagenesis to produce a variegated population of mutants of the antibody or antibody fragment and then screening and selecting those cells that produce the antibody or antibody fragment with the desired enhanced phenotypic properties. U.S. Pat. No. 7,132,273 discloses various yeast cell wall anchor proteins and a surface expression system that uses them to immobilize foreign enzymes or polypeptides on the cell wall.

Of interest are Tanino et al, Biotechnol. Prog. 22: 989-993 (2006), which discloses construction of a Pichia pastoris cell surface display system using Flo1p anchor system; Ren et al., Molec. Biotechnol. 35:103-108 (2007), which discloses the display of adenoregulin in a Pichia pastoris cell surface display system using the Flo1p anchor system; Mergler et al., Appl. Microbiol. Biotechnol. 63:418-421 (2004), which discloses display of K. lactis yellow enzyme fused to the C-terminus half of S. cerevisiae α-agglutinin; Jacobs et al., Abstract T23, Pichia Protein expression Conference, San Diego, CA (Oct. 8-11, 2006), which discloses display of proteins on the surface of Pichia pastoris using α-agglutinin; Ryckaert et al., Abstracts BVBMB Meeting, Vrije Universiteit Brussel, Belgium (Dec. 2, 2005), which discloses using a yeast display system to identify proteins that bind particular lectins; U.S. Pat. No. 7,166,423, which discloses a method for identifying cells based on the product secreted by the cells by coupling to the cell surface a capture moiety that binds the secreted product, which can then be identified using a detection means; U.S. Published Application No. 2004/0219611, which discloses a biotin-avidin system for attaching protein A or G to the surface of a cell for identifying cells that express particular antibodies; U.S. Pat. No. 6,919,183, which discloses a method for identifying cells that express a particular protein by expressing in the cell a surface capture moiety and the protein wherein the capture moiety and the protein form a complex which is displayed on the surface of the cell; U.S. Pat. No. 6,114,147, which discloses a method for immobilizing proteins on the surface of a yeast or fungal using a fusion protein consisting of a binding protein fused to a cell wall protein which is expressed in the cell.

The potential applications of engineering antibodies for the diagnosis and treatment of human disease such as cancer therapy, tumor imaging, sepsis are far-reaching. For these applications, antibodies with high affinity (i.e., Kd≤10 nM) and high specificity are highly desirable. Anecdotal evidence, as well as the a priori considerations discussed previously, suggests that phage display or bacterial display systems are unlikely to consistently produce antibodies of sub-nanomolar affinity. Also, antibodies identified using phage display or bacterial display systems may not be susceptible to commercial scale production in eukaryotic cells. To date, no system has been developed which can accomplish such purpose, and be used.

Therefore, development of further protein expression systems based on improved vectors and host cell lines in which effective protein display facilitates development of genetically enhanced cells for recombinant production of immunoglobulins is a desirable objective.

BRIEF SUMMARY OF THE INVENTION

One of the most powerful applications of the display system herein is its use in the arena of immunoglobulin engineering. It has been shown that scFv antigen-binding units can be expressed on the surface of lower eukaryote host cells with no apparent loss of binding specificity and affinity (See for example, U.S. Pat. No. 6,300,065). It has also been shown that full-length antibodies can be captured and bound to the surface of hybridomas and CHO cells, for example (See U.S. Pat. Nos. 6,919,183 and 7,166,423). While antibodies and fragments thereof to many diverse antigens have been successfully isolated using phage display technology, there is still a need for a robust display system for producing immunoglobulins in eukaryotic host cells and in particular, lower eukaryote host cells. It is particularly desirable to have a robust display system for producing immunoglobulins that have human-like glycosylation patterns. Genetically engineered eukaryote cells that produce glycoproteins that have various human-like glycosylation patterns have been described in U.S. Pat. No. 7,029,872 and for example have been described in Choi et al., Hamilton, et al., Science 313; 1441 1443 (2006); Wildt and Gerngross, Nature Rev. 3: 119-128 (2005); Bobrowicz et al., GlycoBiol. 757-766 (2004); Li et al., Nature Biotechnol. 24: 210-215 (2006);

Chiba et al., J. Biol. Chem. 273: 26298-26304 (1998); and, Mara et al., Glycoconjugate J. 16: 99-107 (1999).

The methods disclosed herein are particularly suited for this application because it allows presentation of a vast diverse repertoire of full-sized immunoglobulins having particular glycosylation patterns on the surface of the cell when the host cells have been genetically engineered to have altered or modified glycosylation pathways. In many respects the subject display system mimics the natural immune system. Antigen-driven stimulation can be achieved by selecting for high-affinity binders from a display library of cloned antibody H and L chains. The large number of chain permutations that occur during recombination of H and L chain genes in developing B cells can be mimicked by shuffling the cloned H and L chains as DNA, and protein and through the use of site-specific recombination (Geoffory et al. Gene 151: 109-113 (1994)). The somatic mutation can also be matched by the introduction of mutations in the CDR regions of the H and L chains.

Immunoglobulins with desired binding specificity or affinity can be identified using a form of affinity selection known as "panning" (Parmley & Smith, Gene 73:305-318 (1988)). The library of immunoglobulins is first incubated with an antigen of interest followed by the capture of the antigen with the bound immunoglobulins. The immunoglobulins recovered in this manner can then be amplified and again gain selected for binding to the antigen, thus enriching for those immunoglobulins that bind the antigen of interest. One or more rounds of selection will enable isolation of antibodies or fragments thereof with the desired specificity or avidity. Thus, rare host cells expressing a desired antibody or fragment thereof can easily be selected from greater than 104 different individuals in one experiment. The primary structure of the binding immunoglobulins is then deduced by nucleotide sequence of the individual host cell clone. When human VH and VL regions are employed in the displayed immunoglobulins, the subject display systems allow selection of human immunoglobulins without further manipulation of a non-human immunoglobulins.

Therefore, in one embodiment, provided is a method for producing eukaryotic host cells that express an immunoglobulin of interest, comprising providing host cells that include a first nucleic acid molecule encoding a capture moiety comprising a cell surface anchoring protein fused to a binding moiety that is capable of specifically binding an immunoglobulin operably linked to a first regulatable promoter; transfecting the host cells with a plurality of nucleic acid molecules encoding a genetically diverse population of heavy and light chains of an immunoglobulin wherein at least one of the heavy or light chain encoding nucleic acid molecules is operably linked to a second regulatable promoter to produce a plurality of genetically diverse host cells capable of displaying an immunoglobulin on the surface thereof; inducing expression of the first nucleic acid molecule encoding the capture moiety for a time sufficient to produce the capture moiety on the surface of the host cells; and inhibiting expression of the first nucleic acid molecule encoding the capture moiety and inducing expression of the nucleic acid molecules encoding the immunoglobulins in the host cells to produce the host cells, which display the immunoglobulin of interest on the surface of the cells. In further aspects, the method further includes contacting the host cells with a detection means that specifically binds to the immunoglobulin of interest displayed on the surface thereof; and isolating host cells in which the detection means is bound to select the host cells that express the immunoglobulin of interest.

In another embodiment, provided is a method for producing eukaryotic host cells that express an immunoglobulin of interest comprising providing a host cell that includes a first nucleic acid molecule encoding a capture moiety comprising a cell surface anchoring protein fused to a binding moiety that is capable of specifically binding an immunoglobulin operably linked to a first regulatable promoter; transfecting the host cell with one or more second nucleic acid molecules encoding an immunoglobulin wherein either the molecules encoding the light chain or the heavy chain are operably linked to a second regulatable promoter, wherein mutagenesis is used to generate a plurality of host cells encoding a variegated population of mutants of the immunoglobulin; inducing expression of the capture moiety for a time sufficient to produce the capture moiety on the surface of the host cells; inhibiting expression of the capture moiety and inducing expression of the variegated population of mutants of the immunoglobulin in the host cells; contacting the plurality of host cells with a detection means that binds to the immunoglobulin of interest to identify host cells in the plurality of host cells that display the immunoglobulin of interest on the surface thereof. In further embodiments, the method further includes isolating the host cells that display the immunoglobulin of interest on the surface of thereof to produce the host cells expressing the immunoglobulin of interest.

In a further embodiment, provided is a method for producing eukaryotic host cells that express an immunoglobulin of interest, comprising: providing a host cell that includes a first nucleic acid molecule encoding a capture moiety comprising a cell surface anchoring protein fused to a binding moiety that is capable of specifically binding an immunoglobulin operably linked to a first regulatable promoter; transfecting the host cells with a one or more nucleic acid molecules encoding the heavy and light chains of an immunoglobulin wherein at least one of the heavy or light chain encoding nucleic acid molecules is operably linked to a second regulatable promoter to generate a plurality of host cells encoding a variegated population of mutants of the immunoglobulins; inducing expression of the capture moiety for a time sufficient to produce the capture moiety on the surface of the host cells; and inhibiting expression of the capture moiety and inducing expression of the variegated population of mutants of the immunoglobulin in the host cells to produce the host cells. In further embodiments, the method further includes contacting the host cells with a detection means that binds to the immunoglobulin of interest to identify host cells that display the immunoglobulin of interest on the surface thereof; and isolating the host cells that display the immunoglobulin of interest on the surface of thereof to produce the host cells that express the immunoglobulin of interest.

In a further embodiment, provided is a method for producing eukaryotic host cells that express an immunoglobulin of interest, comprising providing host cells that include a first nucleic acid molecule encoding a capture moiety comprising a cell surface anchoring protein fused to a binding moiety that is capable of specifically binding an immunoglobulin operably linked to a first regulatable promoter; transfecting the host cells with a plurality of nucleic acid molecules comprising open reading frames (ORFs) encoding a genetically diverse population of heavy and light chains of an immunoglobulin wherein at least the ORFs encoding the heavy chain are operably linked to a second regulatable promoter when the capture moiety binds the heavy chain or at least the ORFs encoding the light chain are operably linked to a second regulatable promoter when the capture moiety binds the light chain to produce a plurality of genetically diverse host cells capable of displaying an immunoglobulin on the surface thereof; inducing expression of the nucleic acid molecule encoding the capture moiety for a time sufficient to produce the capture moiety on the surface of the host cell; and inhibiting expression of the nucleic acid molecule encoding the capture moiety and inducing expression of the nucleic acid molecules encoding the immunoglobulins in the host cells to produce the host cells. In further embodiments, the method further includes contacting the host cells with a detection means that specifically binds to the immunoglobulin of interest displayed on the cell surface of the host cells; and isolating host cells in which the detection means is bound to produce the host cells that express the immunoglobulin of interest.

In a further embodiment, provided is a method of producing eukaryote host cells that produce an immunoglobulin having a VH domain and a VL domain and having an antigen binding site with binding specificity for an antigen of interest, the method comprising (a) providing a library of eukaryote host cells displaying on their surface an immunoglobulin comprising a VH domain and a VL domain, wherein the library is created by (i) providing eukaryote host cells that express a capture moiety comprising a cell surface anchoring protein fused to a moiety capable of binding to an immunoglobulin wherein expression of the capture moiety is effected by a first regulatable promoter; and (ii) transfecting the host cells with a library of nucleic acid molecules encoding a genetically diverse population of immunoglobulins, wherein the VH domains of the genetically diverse population of immunoglobulins are biased for one or more VH gene families and wherein expression of at least one of the heavy or light chains of the immunoglobulins is effected by a second regulatable promoter to produce a plurality of host cells, each expressing an immunoglobulin; (b) inducing expression of the capture moiety in the host cells for a time sufficient to produce the capture moiety on the surface of the host cells; (c) inhibiting expression of the capture moiety and inducing expression of the library of nucleic acid sequences in the host cells, whereby each host cell displays an immunoglobulin at the surface thereof to produce the host cells. In further embodiments, the method further includes (d) identifying host cells in the plurality of host cells that display immunoglobulins thereon that has a binding specificity for the antigen of interest by contacting the plurality of host cells with the antigen of interest and detecting the host cells that have the antigen of interest bound to the immunoglobulin displayed thereon to produce the host cells that produce the immunoglobulin having a VH domain and a VL domain and having the antigen binding site with binding specificity for the antigen of interest.

In a further aspect of the above embodiment, the immunoglobulin comprises a synthetic human immunoglobulin VH domain and a synthetic human immunoglobulin VL domain and wherein the synthetic human immunoglobulin VH domain and the synthetic human immunoglobulin VL domain comprise framework regions and hypervariable loops, wherein the framework regions and first two hypervariable loops of both the VH domain and VL domain are essentially human germ line, and wherein the VH domain and VL domain have altered CDR3 loops. In a further aspect of the above embodiment, in addition to having altered CDR3 loops the human synthetic immunoglobulin VH and VL domains contain mutations in other CDR loops. In a further still aspect of the above embodiment, each human synthetic immunoglobulin VH domain CDR loop is of random sequence, and in a further still aspect of the above embodiment, the human synthetic immunoglobulin VH domain CDR loops are of known canonical structures and incorporate random sequence elements.

In a further embodiment, provided is a eukaryote host cell comprising a nucleic acid molecule encoding a capture moiety comprising a cell surface anchoring protein fused to a binding moiety capable of binding an immunoglobulin operably linked to a regulatable promoter and one or more nucleic acid molecules encoding the heavy and light chains of immunoglobulins, wherein at least one of the nucleic acid molecules encoding the heavy or light chains is operably linked to a second regulatable promoter. In particular embodiments, the nucleic acid molecules encoding both the heavy and light chains are operably linked to a second regulatable promoter. In other embodiments, the nucleic acid molecules encoding the heavy chains are operably linked to a second regulatable promoter and the nucleic acid molecules encoding the light chain are operably linked to a third regulatable promoter or to a constitutive promoter. In other embodiments, the nucleic acid molecules encoding the light chains are operably linked to a second regulatable promoter and the nucleic acid molecules encoding the heavy chain are operably linked to a third regulatable promoter or to a constitutive promoter. In particular aspects, the heavy and light chains are encoded by separate open reading frames (ORFs) wherein each ORF is operably linked to a promoter. In other aspects, the heavy and light chains are encoded by a single ORF, which produces a single fusion polypeptide comprising the heavy and light chains in a tandem orientation, and the ORF is operably linked to a regulatable promoter. The single polypeptide is cleavable between the heavy and light chains to produce separate heavy and light chain proteins, which can then associate to form a functional antibody molecule.

In various aspects of any one of the above embodiments or aspects, the binding moiety that binds the immunoglobulin binds the Fc region of the immunoglobulin. Examples of such binding moieties include, but are not limited to those selected from the group consisting of protein A, protein A ZZ domain, protein G, and protein L and fragments thereof that retain the ability to bind to the immunoglobulin. Examples of other binding moieties, include but are not limited to, Fc receptor (FcR) proteins and immunoglobulin-binding fragments thereof. The FCR proteins include members of the Fc gamma receptor (FcγR) family, which bind gamma immunoglobulin (IgG), Fc epsilon receptor (FcεR) family, which bind epsilon immunoglobulin (IgE), and Fc alpha receptor (FcαR) family, which bind alpha immunoglobulin (IgA). Particular FcR proteins that bind IgG that can comprise the binding moiety herein include at least the IgG binding region of FcγRI, FcγRIIA, FcγRIIB1, FcγRIIB2, FcγRIIIA, FcγRIIIB, or FcγRn (neonatal).

In further aspects of any one of the above embodiments or aspects, detection means is an antigen that is capable of being bound by the immunoglobulin of interest. In particular aspects, the antigen is conjugated to or labeled with a fluorescent moiety. In other aspects, the detection means further includes a detection immunoglobulin that is specific for the immunoglobulin-antigen complex or is specific for another epitope on the antigen and it is this detection immunoglobulin that is conjugated to or labeled with a detection moiety such as a fluorescent moiety.

In further aspects of any one of the above embodiments or aspects, the cell surface anchoring protein is a Glycosylphosphatidylinositol-anchored (GPI) protein. In particular aspects, the cell surface anchoring protein is selected from the group consisting of α-agglutinin, Cwp1p, Cwp2p, Gas1p, Yap3p, Flo1p, Crh2p, Pir1p, Pir4p, Sed1p, Tip1p, Wpip, Hpwp1p, Als3p, and Rbt5p. In further aspects, the cell surface anchoring protein is Sed1p.

The host cell that can be used includes both lower and high eukaryote cells. Higher eukaryote cells include mammalian, insect, and plant cells. In further aspects of any one of the above embodiments or aspects, the eukaryote is a lower eukaryote. In further aspects, the host cell is a yeast or filamentous fungi cell, which in particular aspects is selected from the group consisting of  Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum and Neurospora crassa. In particular aspects, the eukaryote is a yeast and in further aspects, the yeast is Pichia pastoris. While the methods herein have been exemplified using Pichia pastoris as the host cell, the methods herein can be used in other lower eukaryote or higher eukaryote cells for the same purposes disclosed herein.

In further aspects of any one of the aforementioned methods, O-glycosylation of glycoproteins in the host cell is controlled. That is, O-glycan occupancy and mannose chain length are reduced. In lower eukaryote host cells such as yeast, O-glycosylation can be controlled by deleting the genes encoding one or more protein O-mannosyltransferases (Dol-P-Man:Protein (Ser/Thr) Mannosyl Transferase genes) (PMTs) or by growing the host in a medium containing one or more Pmtp inhibitors. In further aspects, the host cell includes a deletion of one or more of the genes encoding PMTs and the host cell is cultivated in a medium that includes one or more Pmtp inhibitors. Pmtp inhibitors include but are not limited to a benzylidene thiazolidinedione. Examples of benzylidene thiazolidinediones that can be used are 5-[[3,4-bis(phenylmethoxy) phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid. In further still aspects, the host cell further includes a nucleic acid that encodes an alpha-1,2-mannosidase that has a signal peptide that directs it for secretion.

In further aspects of any one of the aforementioned methods, host cells further include lower eukaryote cells (e.g., yeast such as Pichia pastoris) that are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Published Patent Application No. 2006/0211085) or abrogating translation of RNAs encoding one or more of the β-mannosyltransferase-susing interfering RNA, antisense RNA, or the like.

In further aspects of any one of the methods herein, the host cells can further include lower eukaryote cells (e.g., yeast such as Pichia pastoris) that are genetically engineered to eliminate glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene or abrogating translation of RNAs encoding one or more of the phosphomannosyltransferases using interfering RNA, antisense RNA, or the like.

In further still aspects, the host cell has been genetically modified to produce glycoproteins that have predominantly an N-glycan selected from the group consisting of complex N-glycans, hybrid N-glycans, and high mannose N-glycans wherein complex N-glycans are selected from the group consisting of $Man_3GlcNAc_2$, $GlcNAC_{(1-4)}Man_3GlcNAc_2$, $Gal_{(1-4)} GlcNAc_{(1-4)}Man_3GlcNAc_2$, and $NANA_{(1-4)}Gal_{(1-4)} Man_3GlcNAc_2$; hybrid N-glycans are selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high Mannose N-glycans are selected from the group consisting of $Man_6GlcNAc_2$, $Man_7GlcNAc_2$, $Man_8GlcNAc_2$, and $Man_9GlcNAc_2$.

In any one of the above embodiments or aspects, the first regulatable promoter is a promoter that is inducible without inducing expression of the second regulatable promoter. The second regulatable promoter is a promoter that is inducible without inducing the expression of the first regulatable promoter. In further aspects, the inducer of the second regulatable promoter inhibits transcription from the first regulatable promoter. In particular aspects in which the host cells are yeast, the first regulatable promoter is the GUT1 promoter and the second regulatable promoter is the GADPH promoter. In other aspects, the first regulatable promoter is the PCK1 promoter and the second regulatable promoter is the GADPH promoter.

In general, in the above embodiments or aspects, the immunoglobulin will be an IgG molecule and can include IgG1, IgG2, IgG3, and IgG4 immunoglobulins and subspecies thereof. However, in particular aspects of the above, the immunoglobulin is selected from the group consisting of IgA, IgM, IgE, camel heavy chain, and llama heavy chain.

The information derived from the host cells and methods herein can be used to produce affinity matured immunoglobulins, derivatives of the antibodies, and modified immunoglobulins or the nucleic acid encoding the desired immunoglobulin can be subcloned into another host cell for production or affinity maturation of the immunoglobulin. Therefore, further provided is a host cell that expresses an immunoglobulin that had been identified using any one of the aforementioned methods but does not necessarily have to be the host cell that was used to identify the immunoglobulin. The host cell can be a prokaryote or eukaryote host cell.

Further provided is an immunoglobulin produced by any one of the above embodiments or aspects.

The following terms, unless otherwise indicated, shall be understood to have the following meanings:

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues in the Golgi apparatus for N-linked glycoproteins.

N-glycans have a common pentasaccharide core of Man3GlcNAc2 ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the Man3GlcNAc2 ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "transfect", transfection", "transfecting" and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia sliptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium* lucknowense, any *Fusarium* sp. and *Neurospora crassa*.

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD, and IgE, respectively.

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3, and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the CH2 domain of the heavy chain immunoglobulin constant region which comprises an N-linked glycosylation site of the CH2 domain, or a variant thereof. Included within the terms are molecules comprising only the Fc region, such as immunoadhesins (U.S. Published Patent Application No. 20040136986), Fc fusions, and antibody-like molecules.

The term "Fc" fragment refers to the 'fragment crystallized' C-terminal region of the antibody containing the CH2 and CH3 domains. The term "Fab" fragment refers to the 'fragment antigen binding' region of the antibody containing the VH, CH1, VL and CL domains.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be synthesized by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567 to Cabilly et al.).

The term "fragments" within the scope of the terms "antibody" or "immunoglobulin" include those produced by digestion with various proteases, those produced by chemical cleavage and/or chemical dissociation and those produced recombinantly, so long as the fragment remains capable of specific binding to a target molecule. Among such fragments are Fc, Fab, Fab', Fv, F(ab')2, and single chain Fv (scFv) fragments. Hereinafter, the term "immunoglobulin" also includes the term "fragments" as well.

Immunoglobulins further include immunoglobulins or fragments that have been modified in sequence but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (See, for example, Intracellular Antibodies: Research and Disease Applications, (Marasco, ed., Springer-Verlag New York, Inc., 1998).

The term "catalytic antibody" refers to immunoglobulin molecules that are capable of catalyzing a biochemical reaction. Catalytic antibodies are well known in the art and have been described in U.S. Patent Application Nos. 7205136; 4888281; 5037750 to Schochetman et al., U.S. Patent Application Nos. 5733757; 5985626; and U.S. Pat. No. 6,368,839 to Barbas, III et al.

As used herein, the term "consisting essentially of" will be understood to imply the inclusion of a stated integer or group of integers; while excluding modifications or other integers which would materially affect or alter the stated integer. With respect to species of N-glycans, the term "consisting essentially of" a stated N-glycan will be understood to include the N-glycan whether or not that N-glycan is fucosylated at the N-acetylglucosamine (GlcNAc) which is directly linked to the asparagine residue of the glycoprotein.

As used herein, the term "predominantly" or variations such as "the predominant" or "which is predominant" will be understood to mean the glycan species that has the highest mole percent (%) of total neutral N-glycans after the glycoprotein has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A in 40 mole percent, species B in 35 mole percent and species C in 25 mole percent, the composition comprises predominantly species A, and species B would be the next most predominant species. Some host cells may produce compositions comprising neutral N-glycans and charged N-glycans such as mannosylphosphate. Therefore, a composition of glycoproteins can include a plurality of charged and uncharged or neutral N-glycans. In the present invention, it is within the context of the total plurality of neutral N-glycans in the composition in which the predominant N-glycan determined. Thus, as used herein, "predominant N-glycan" means that of the total plurality of neutral N-glycans in the composition, the predominant N-glycan is of a particular structure.

As used herein, the term "essentially free of" a particular sugar residue, such as fucose, or galactose and the like, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent. Thus, substantially all of the N-glycan structures in a glycoprotein composition according to the present invention are free of fucose, or galactose, or both.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast (for example, *Pichia* sp.; *Saccharomyces* sp.; *Kluyveromyces* sp.; *Aspergillus* sp.), and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

The interaction of antibodies and antibody-antigen complexes with cells of the immune system and the variety of responses, including antibody-dependent cell-mediated cytotoxicity (ADCC) and complement-dependent cytotoxicity (CDC), clearance of immunocomplexes (phagocytosis), antibody production by B cells and IgG serum half-life are defined respectively in the following: Dacron et al., 1997, Annu. Rev. Immunol. 15: 203-234; Ward and Ghetie, 1995, Therapeutic Immunol. 2:77-94; Cox and Greenberg, 2001, Semin. Immunol. 13: 339-345; Heyman, 2003, Immunol. Lett. 88:157-161; and Ravetch, 1997, Curr. Opin. Immunol. 9: 121-125.

BRIEF DESCRIPTION OF THE DRAWINGS

FIG. 4A and FIG. 4B illustrate the construction of plasmid vector pGFI207t.

FIG. 17 illustrates the hypothetical expression of Protein A/SED1 fusion protein and antibody under the control of different combinations of promoters.

FIG. 19A shows the results for the anti-CD20 expressing strain and FIG. 19B shows the results for the anti-Her2 expressing strain. Y2696/pGLY4144 represents the negative control without co-expression of antibody.

DETAILED DESCRIPTION OF THE INVENTION

Figure 1:
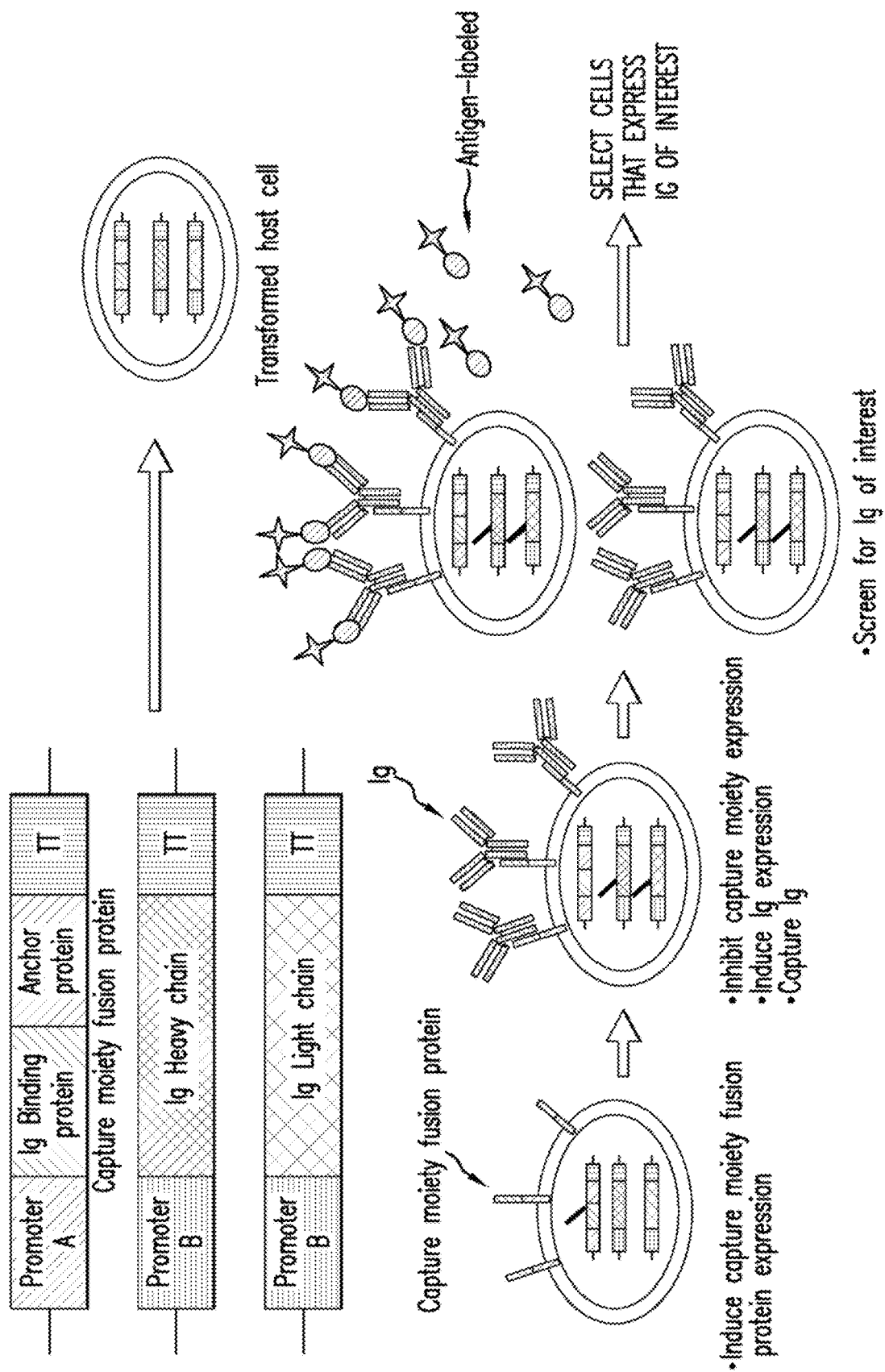
FIG. 1 illustrates the general operation of the method using an embodiment wherein the immunoglobulin (Ig) light and heavy chains are separately expressed and detection of cells that express the immunoglobulin of interest is via a labeled antigen.

The present invention provides a protein display system that is capable of displaying diverse libraries of immunoglobulins on the surface of a eukaryote host cell. The compositions and methods are particularly useful for the display of collections of immunoglobulins in the context of discovery (that is, screening) or molecular evolution protocols. A salient feature of the method is that it provides a display system in which a whole, intact immunoglobulin molecule of interest can be displayed on the surface of a host cell without having to express the immunoglobulin molecule of interest either as fusion protein in which it is fused to a surface anchor protein or other moiety that enables capture of the immunoglobulin by a capture moiety bound to the cell surface. Another feature of the method is that it enables screening diverse libraries of immunoglobulins in host cells for a host cell in the library that produces an immunoglobulin of interest and then enables the host cell to be separated from the other host cells in the library that do not express the immunoglobulin of interest. Importantly, the isolated host cell can then be used for production of the immunoglobulin of interest for use in therapeutic or diagnostic applications. This is an improvement over phage and yeast display methods wherein a diverse library of scFV or Fab fragments are screened for a host cell that expresses an scFV or Fab of interest, which is then used in a series of steps to construct a mammalian host cell that expresses a whole immunoglobulin with the characteristics of the scFV or Fab of interest. These subsequent steps present the risk that the desired affinity or specificity of an scFV or Fab that has been identified during the maturation process of converting the scFV or Fab into a whole immunoglobulin could be abrogated or diminished.

While current phage-based methods provide substantial library diversity and have greatly improved the processes for developing immunoglobulins, a disadvantage is that the prokaryotic host cells used to construct the libraries do not produce N-linked glycosylated glycoproteins. Posttranslational modifications such as glycosylation can affect specificity or affinity of the immunoglobulin. It is estimated that about 15-20% of circulating monoclonal antibodies derived entirely in mammalian cells contain one or more N-linked glycans in the variable regions. (Jefferis, Biotechnol Progress 21: 11-16 (2005)) In some cases it is believed that these N-glycans in the variable region may play a significant role in immunoglobulin function. For example, both positive and negative influences on antigen binding have been seen in antibody molecules with variable region N-glycosylation. N-glycosylation consensus sites added within the CDR2 region of an anti-dextran antibody were filled with carbohydrates of varying structure and showed changes in affinity, half-life and tissue targeting in a site dependent manner (Coloma et al., The Journal of Immunology 162: 2162-2170 (1999)). Therefore, libraries produced and screened in prokaryotic host cells will tend to be biased against immunoglobulin species that might have glycosylation in the variable region. Thus, immunoglobulins that might have particularly desirable specificity or affinity due in whole or in part to glycosylation of one or more sites in the variable regions will not be identified. Conversely, antibodies identified through prokaryotic screening methods may, when expressed in a eukaryotic host, have glycosylation structures that unfavorably impact folding or affinity. The methods and systems herein for the first time enable libraries of immunoglobulins to be screened wherein the libraries include populations of immunoglobulins that are glycosylated in the variable region. This has the potential effect of increasing the diversity of the library over what would be expected if the diversity of the library was based solely on sequence. This improvement is expected to increase the ability to develop immunoglobulins that have greater specificity or affinity than current methods permit.

The methods and systems herein also provide another advantage over current methods in that eukaryote host cells that have been genetically engineered to produce glycoproteins that have predominantly particular N-glycan structures can be used. The N-glycan structures include any of the N-glycan structures currently found on human immunoglobulins or N-glycan structures that lack features not found in glycoproteins from higher eukaryotes. For example, in the case of yeast, the host cells can be genetically engineered to produce immunoglobulins wherein the N-glycans are not hypermannosylated. The host cells can be genetically engineered to limit the amount of O-glycosylation or to modify O-glycosylation to resemble O-glycosylation in mammalian cells.

A significant advantage of the methods and systems is that the host cell identified in the library to produce a desired immunoglobulin can be used without further development or manipulation of the host cell or the nucleic acid molecule encoding the immunoglobulin for production of the immunoglobulin. That is, cultivating the host cells identified herein as expressing the desired immunoglobulin under conditions that induce expression of the desired immunoglobulin without inducing expression of the capture moiety either before, after, or at the same time: the cells secrete the desired immunoglobulin, which can then be recovered from the culture medium using methods well known in the art. An important element is that the immunoglobulin that is produced is a whole, intact immunoglobulin molecule. This ability to use library cells to produce whole, intact immunoglobulins is not possible with the current phage-based or yeast-based systems. In those systems, the nucleic acid molecules encoding the desired Fab or scFV has to be further manipulated to construct a nucleic acid molecule that encodes a whole, intact immunoglobulin, which is then transfected into a mammalian cell for production of the whole, intact immunoglobulin. Thus, the methods and systems herein provide significant improvements to the development and production of immunoglobulins for therapeutic or diagnostic purposes.

What is provided then is a method for constructing and isolating a eukaryotic host cell expressing an immunoglobulin of interest from a library of host cells expressing a plurality of immunoglobulins. The method enables the construction and selection of immunoglobulins with desirable specificity and/or affinity properties. In general, the method comprises providing a host cell that comprises a first nucleic acid molecule encoding a capture moiety comprising a cell surface anchoring protein fused to a binding moiety that is capable of specifically binding an immunoglobulin operably linked to a first regulatable promoter. The host cell can be further genetically engineered to produce immunoglobulins having particular predominant N-glycan structures.

In one aspect, the host cell is propagated in a culture to provide a multiplicity of host cells, which are then transfected with a plurality of second nucleic acid molecules, each nucleic acid molecule encoding the heavy and/or light chains of an immunoglobulin wherein at least the nucleic acid encoding a heavy chain is operably linked to a second regulatable promoter when the capture moiety binds the heavy chain or at least the nucleic acid encoding a light chain is operably linked to a second regulatable promoter when the capture moiety binds the light chain. This produces a plurality of host cells wherein each host cell in the plurality of host cells capable of displaying an immunoglobulin on the surface thereof and each host cell in the plurality of host cells is capable of displaying a particular distinct immunoglobulin species. In general, the diversity of the host cell population in the plurality of host cells will depend on the diversity of the library of nucleic acid molecules that was transfected into the host cells.

In another aspect, the host cell is propagated in a culture to provide a multiplicity of host cells, which are then transfected with one or more nucleic acid second molecules encoding the heavy and/or light chains of an immunoglobulin wherein at least the nucleic acid encoding a heavy chain is operably linked to a second regulatable promoter when the capture moiety binds the heavy chain or at least the nucleic acid encoding a light chain is operably linked to a second regulatable promoter when the capture moiety binds the light chain to provide a multiplicity of host cells that are capable of displaying the encoded immunoglobulin on the surface thereof. Mutagenesis of the multiplicity of host cells is used to generate a plurality of host cells that encode a variegated population of mutants of the immunoglobulin. The diversity is dependent on the mutagenesis method used. Suitable methods for mutagenesis include but are not limited to cassette mutagenesis, error-prone PCR, chemical mutagenesis, or shuffling to generate a refined repertoire of altered sequences that resemble the parent nucleic acid molecule. In further aspects, the host cell is propagated in a culture to provide a multiplicity of host cells, which are then transfected with a plurality of second nucleic acid molecules, each nucleic acid molecule encoding the heavy and/or light chains of an immunoglobulin wherein at least the nucleic acid encoding a heavy chain is operably linked to a second regulatable promoter when the capture moiety binds the heavy chain or at least the nucleic acid encoding a light chain is operably linked to a second regulatable promoter when the capture moiety binds the light chain to produce a plurality of host cells that are capable of displaying an immunoglobulin on the surface thereof. Mutagenesis is then used to generate further increase the diversity of the plurality of host cells that are capable of displaying an immunoglobulin on the surface thereof.

In particular embodiments, the nucleic acid molecules encoding both the heavy and light chains are operably linked to a second regulatable promoter. In other embodiments, the nucleic acid molecules encoding at least one of the heavy chains are operably linked to a second regulatable promoter and the nucleic acid molecules encoding the light chain are operably linked to a third regulatable promoter or to a constitutive promoter. In particular aspects, a plurality of nucleic acids encoding sub-populations of heavy chains are provided wherein expression of each sub-population is effected by a second, third, or more regulatable promoter such that different sub-populations can be expressed at a particular time while other sub-populations are not expressed at that time.

In general, the heavy and light chains are encoded by separate open reading frames (ORFs) wherein each ORF is operably linked to a promoter. However, in other aspects, the heavy and light chains are encoded by a single ORF, which produces a single fusion polypeptide comprising the heavy and light chains in a tandem orientation, and the ORF is operably linked to a regulatable promoter. The single polypeptide is cleavable between the heavy and light chains to produce separate heavy and light chain proteins, which can then associate to form a functional antibody molecule. (See for example, U.S. Published Application No. 2006/ 0252096).

In any one of the above aspects, the expression of the first nucleic acid molecule encoding the capture moiety is induced for a time sufficient to produce the capture moiety and allow it to be transported to and then bound to the surface of the host cell such that the capture moiety is capable of binding immunoglobulin molecules as they are secreted from the host cell. Expression of the capture moiety is then reduced or inhibited and expression of the nucleic acid molecules encoding the heavy and/or light chains of the immunoglobulins operably linked to the second regulatable promoter is induced. While expression of both the heavy and light chains can be induced, in particular aspects, the expression of the heavy chain is induced and expression of the light chain is constitutive. In other aspects, when the capture moiety binds the light chain, expression of the light chain can be regulated and expression of the heavy chain can be constitutive. Thus, whether it is the heavy chain or the light chain that is captured determines whether it is the light chain or the heavy chain whose expression is regulated.

Inhibition of expression of the capture moiety can be effected by no longer providing the inducer than induces expression of the capture moiety, or by providing an inhibitor of the first regulatable promoter that inhibits expression of the capture moiety, or by using an inducer of expression of the immunoglobulins heavy and/or light chains operably linked to a second or more inducible promoter that also inhibits expression of the capture moiety. Inhibition can be complete repression of expression or a reduction in expression to an amount wherein expression of the capture moiety is such that it does not interfere with the processing and transport of the heavy and light chains through the secretory pathway. The expressed immunoglobulin heavy and/or light chains are processed and transported to the cell surface via the host cell secretory pathway where they are captured by the capture moiety bound to the host cell surface for display. The plurality of host cells with the expressed immunoglobulins displayed thereon are then screened using a detection means that will bind to the immunoglobulin of interest but not to other immunoglobulins to identify the host cells that display the immunoglobulin of interest on the surface thereof from those host cells that do not display the immunoglobulin of interest. Host cells that express and display the immunoglobulin of interest are separated from the host cells that do not express and display the immunoglobulin of interest to produce a population of host cells comprising exclusively or enriched for the host cells displaying the immunoglobulin of interest. These separated host cells can be propagated and used to produce the inunumoglobulin of interest in the quantities needed for the use intended. The nucleic acid encoding the immunoglobulin can be determined and an expression vector encoding the heavy and light chains of the immunoglobulin can be constructed and used to transfect another host cell, which can be a prokaryotic or eukaryotic host cell.

Detection and analysis of host cells that express the immunoglobulin of interest can be achieved by labeling the host cells with an antigen that is specifically recognized by the immunoglobulin of interest. In particular aspects, the antigen is labeled with a detection moiety. In other aspects the antigen is unlabeled and detection is achieved by using a detection immunoglobulin that is labeled with a detection moiety and binds an epitope of the antigen that is not bound by the immunoglobulin of interest. This enables selection of host cells that produce immunoglobulins that bind the antigen at an epitope other than the epitope bound by the detection immunoglobulin. In another aspect, the detection immunoglobulin is specific for the immunoglobulin-antigen complex. Regardless of the detection means, a high occurrence of the label indicates the immunoglobulin of interest has desirable binding properties and a low occurrence of the label indicates the immunoglobulin of interest does not have desirable binding properties.

Detection moieties that are suitable for labeling are well known in the art. Examples of detection moieties, include but are not limited to, fluorescein (FITC), Alexa Fluor® dyes such as Alexa Fluor® 488 (Invitrogen), green fluorescence protein (GFP), Carboxyfluorescein succinimidyl ester (CFSE), DyLight® Fluors (Thermo Fisher Scientific), HyLite® Fluors (AnaSpec), and phycoerythrin. Other detection moieties include but are not limited to, magnetic beads which are coated with the antigen of interest or immunoglobulins that are specific for the immunoglobulin of interest or immunoglobulin-antigen complex. In particular aspects, the magnetic beads are coated with anti-fluorochrome immunoglobulins specific for the fluorescent label on the labeled antigen or immunoglobulin. Thus, the host cells are incubated with the labeled-antigen or immunoglobulin and then incubated with the magnetic beads specific for the fluorescent label.

Analysis of the cell population and cell sorting of those host cells that display the immunoglobulin of interest based upon the presence of the detection moiety can be accomplished by a number of techniques known in the art. Cells that display the immunoglobulin of interest can be analyzed or sorted by, for example, flow cytometry, magnetic beads, or fluorescence-activated cell sorting (FACS). These techniques allow the analysis and sorting according to one or more parameters of the cells. Usually one or multiple secretion parameters can be analyzed simultaneously in combination with other measurable parameters of the cell, including, but not limited to, cell type, cell surface antigens, DNA content, etc. The data can be analyzed and cells that display the immunoglobulin of interest can be sorted using any formula or combination of the measured parameters. Cell sorting and cell analysis methods are known in the art and are described in, for example, The Handbook of Experimental Immunology, Volumes 1 to 4, (D. N. Weir, editor) and Flow Cytometry and Cell Sorting (A. Radbruch, editor, Springer Verlag, 1992). Cells can also be analyzed using microscopy techniques including, for example, laser scanning microscopy, fluorescence microscopy; techniques such as these may also be used in combination with image analysis systems. Other methods for cell sorting include, for example, panning and separation using affinity techniques, including those techniques using solid supports such as plates, beads, and columns.

In further aspects, provided is a library method for identifying and selecting cells that produce an immunoglobulin having a desired specificity and/or affinity for a particular antigen. The method comprises providing a library of eukaryote host cells displaying on their surface an immunoglobulin comprising a VH domain and a VL domain, wherein the library is created by (i) providing eukaryote host cells that express a capture moiety comprising a cell surface anchoring protein fused to a moiety capable of binding an immunoglobulin wherein expression of the capture moiety is effected by a first regulatable promoter; and (ii) transfecting the host cells with a library of nucleic acid sequences encoding a genetically diverse population of immunoglobulins, wherein the VH domains of the genetically diverse population of immunoglobulins are biased for one or more VH gene families and wherein expression of at least one or more heavy or light chains is effected by a second regulatable promoter to produce a plurality of host cells, each host cell in the plurality of host cells expresses an immunoglobulin species. Expression of the capture moiety is induced in the plurality of host cells for a time sufficient to produce the capture moiety on the surface of the host cells. Then expression of the of the capture moiety while expression of the library of nucleic acid sequences is induced in the plurality of host cells to produce a plurality of host cells wherein each host cell displays an immunoglobulin species at the surface thereof. Host cells in the plurality of host cells that display immunoglobulins thereon that has a binding specificity for the antigen of interest are identified by contacting the plurality of host cells with the antigen of interest and detecting the host cells that have the antigen of interest bound to the immunoglobulin displayed thereon to produce the host cells that produce the immunoglobulin having a VH domain and a VL domain and having the antigen binding site with binding specificity for the antigen of interest. In particular aspects, the immunoglobulin comprises a synthetic human immunoglobulin VH domain and a synthetic human immunoglobulin VL domain and further, the synthetic human immunoglobulin VH domain and the synthetic human immunoglobulin VL domain comprise framework regions and hypervariable loops, wherein the framework regions and first two hypervariable loops of both the VH domain and VL domain are essentially human germ line, and wherein the VH domain and VL domain have altered CDR3 loops.

This provides a library of host cells that are capable of expressing a plurality of immunoglobulin molecules, which can be captured and displayed on the cell surface for detection by a detection means that can bind an immunoglobulin specific for a particular antigen and thereby enable the host cell expressing the immunoglobulin to be identified from the plurality of host cells in the library. In general, the detection means will usually use the antigen that has been labeled with a detection moiety. These host cells can be isolated from the plurality of host cells by any means currently used for selection of particular cells in a population of cells, e.g., FACS sorting.

Thus, the method comprises at least two components. The first component is a helper vector that contains an expression cassette comprising the first nucleic acid molecule that encodes and expresses a capture moiety that in particular embodiments comprises a cell surface anchoring protein or cell wall binding protein that is capable of binding or integrating to the surface of the host cell fused at its N- or C-terminus to a binding moiety capable of binding an immunoglobulin. The binding moiety is located at the end of the cell surface anchoring protein that is exposed to the extracellular environment such that the binding moiety is capable of interacting with an immunoglobulin. The immunoglobulin binding moiety includes the immunoglobulin binding domains from such molecules as protein A, protein G, protein L, or the like or an Fc receptor.

The second component is one or more vectors that contain expression cassettes that encode and express the heavy and light chains of an immunoglobulin of interest or libraries of which the immunoglobulin of interest is to be selected (for example, a library of vectors expressing immunoglobulins). In particular aspects, the nucleic acid molecule encoding the immunoglobulin may include the nucleotide sequences encoding both the heavy and the light chains of the immunoglobulins, e.g., an immunoglobulin having a VH domain and a VL domain and having an antigen binding site with binding specificity for an antigen of interest. In other aspects, the heavy and light chains are encoded on separate nucleic acid molecules. In either case, these nucleic acid molecules may further include when desirable codon optimizations to enhance translation of the mRNA encoding the immunoglobulins in the host cell chosen. The nucleic acid molecule may further include when desirable replacement of endogenous signal peptides with signal peptides that are appropriate for the host cell chosen.

In one aspect, the above nucleic acid molecule can comprise a single expression cassette operably linked to a second regulatable promoter wherein the open reading frames (ORFs) for the light and heavy chains are in frame and separated by a nucleic acid molecule encoding in frame a protease cleavage site that upon expression produces a fusion protein that is processed post-translationally with a protease specific for the protease cleavage site to produce the light and heavy chains of the immunoglobulin. Examples of these expression cassettes can be found in for example, U.S. Publication No. 20060252096. In another aspect, the heavy and light immunoglobulin chains are expressed from separate expression cassettes wherein the ORF encoding each of the light and heavy chains is operably linked to a second regulatable promoter. Examples of these expression cassettes can be found in for example, U.S. Pat. Nos. 4,816,567 and 4,816,397. In a further aspect, the heavy and light immunoglobulin chains are expressed from separate expression cassettes wherein the ORF encoding the heavy chain is operably linked to a second regulatable promoter and the ORF encoding the light chain is operably linked to a constitutive promoter.

In particular aspects, the encoded immunoglobulin comprises a synthetic human immunoglobulin VH domain and a synthetic human immunoglobulin VL domain and wherein the synthetic human immunoglobulin VH domain and the synthetic human immunoglobulin VL domain comprise framework regions and hypervariable loops, wherein the framework regions and first two hypervariable loops of both the VH domain and VL domain are essentially human germ line, and wherein the VH domain and VL domain have altered CDR3 loops. In further still aspects, in addition to having altered CDR3 loops, the human synthetic immunoglobulin VH and VL domains contain mutations in other CDR loops. In further aspects, each human synthetic immunoglobulin VH domain CDR loop is of random sequence. In further still aspects, the human synthetic immunoglobulin VH domain CDR loops are of known canonical structures and incorporate random sequence elements.

Both of the components can be provided in vectors which integrate the nucleic acid molecules into the genome of the host cell by homologous recombination. Homologous recombination can be double crossover or single crossover homologous recombination. Roll-in single crossover homologous recombination has been described in Nett et al., Yeast 22: 295-304 (2005). Each component can be integrated in the same locus in the genome or in separate loci in the genome. Alternatively, one or both components can be transiently expressed in the host cell.

FIG. 1 illustrates the general operation of the method using an embodiment wherein the immunoglobulin light and heavy chains are separately expressed and detection is via a labeled antigen. FIG. 1 shows an expression cassette encoding the capture moiety fusion protein operably linked to promoter A and expression cassettes encoding the immunoglobulin (Ig) light and heavy chains, each operably linked to promoter B. As shown, the host cell is transfected with the expression cassettes and the transformed cells grown under conditions that induce expression of the capture moiety fusion protein via promoter A. The capture moiety fusion protein is anchored to the cell surface. Then the cells are grown under conditions that inhibit or reduce expression of the capture moiety fusion protein but induce expression of the immunoglobulin light and heavy chains via promoter B. The immunoglobulins are secreted from the cells and captured by the capture moiety fusion protein anchored to the cell surface. The cells with the captured immunoglobulins are then screened for the Ig of interest using a antigen labeled with a detection moiety. As shown, not all cells will produce the immunoglobulin of interest. Cells that bind the labeled antigen are selected and separated from cells that do not produce the immunoglobulin of interest. This produces cells that express the immunoglobulin of interest. These cells can be used for producing the immunoglobulin for use in therapeutic or diagnostic applications. Alternatively, the cells can undergo mutagenesis that introduces mutations into the expression cassettes encoding the immunoglobulins and the cells screened for cells that produce immunoglobulins with properties that have been modified or altered from those properties in the immunoglobulin prior to mutagenesis and which are desired. Cells that express immunoglobulins having modified or altered but desired properties can be separated from the other cells and used for producing the immunoglobulin for therapeutic or diagnostic applications.

Glycosylphosphatidylinositol-anchored (GPI) proteins provide a suitable means for tethering the capture moiety to the surface of the host cell. GPI proteins have been identified and characterized in a wide range of species from humans to yeast and fungi. Thus, in particular aspects of the methods disclosed herein, the cell surface anchoring protein is a GPI protein or fragment thereof that can anchor to the cell surface. Lower eukaryotic cells have systems of GPI proteins that are involved in anchoring or tethering expressed proteins to the cell wall so that they are effectively displayed on the cell wall of the cell from which they were expressed. For example, 66 putative GPI proteins have been identified in *Saccharomyces cerevisiae* (See, de Groot et al., Yeast 20: 781-796 (2003)). GPI proteins which may be used in the methods herein include, but are not limited to, *Saccharomyces cerevisiae* CWP1, CWP2, SED1, and GAS1; *Pichia pastoris* SP1 and GAS1; and *H. polymorpha* TIP1. Additional GPI proteins may also be useful. Additional suitable GPI proteins can be identified using the methods and materials of the invention described and exemplified herein.

The selection of the appropriate GPI protein will depend on the particular recombinant protein to be produced in the host cell and the particular post-translation modifications to be performed on the recombinant protein. For example, production of immunoglobulins with particular glycosylation patterns will entail the use of recombinant host cells that produce glycoproteins having particular glycosylation patterns. The GPI protein most suitable in a system for producing antibodies or fragments thereof that have predominantly Man5GlcNAc2 N-glycosylation many not necessarily be the GPI protein most suitable in a system for producing antibodies or thereof having predominantly Gal2GlcNAc2Man3GlcNAc2 N-glycosylation. In addition, the GPI most suitable in a system for producing immunoglobulins specific for one epitope or antigen may not necessarily be the most suitable GPI protein in a system for producing immunoglobulins specific for another epitope or antigen.

Therefore, further provided is a library method for constructing the host cell that is to be used for producing a particular immunoglobulin. In general, the host cell that is desired to produce the particular immunoglobulin is selected based on the desired characteristics that will be imparted to the particular immunoglobulin produced by the host cell. For example, a host cell that produces glycoproteins having predominantly Man5GlcNAc2 or Gal$_2$GlcNAc$_2$Man$_3$GlcNAc$_2$N-glycosylation is selected and a library of vectors encoding GPI proteins fused to one or more immunoglobulin capture moieties is then provided (GPI-IgG capture moiety). A library of host cells is then constructed wherein each host cell to make up the library is transfected with one of the vectors in the library of vectors encoding GPI-IgG capture moiety fusion proteins such that each host cell species in the library will express one particular GPI-IgG capture moiety fusion protein. Each host cell species of the library is then transfected with a vector encoding the desired particular immunoglobulin. The host cell that results in the best presentation of the particular immunoglobulin on the surface of the host cell is selected as the host cell for producing the particular immunoglobulin.

In general, the GPI protein used in the methods disclosed herein is a chimeric protein or fusion protein comprising the GPI protein fused at its N-terminus to the C-terminus of an immunoglobulin capture moiety. The N-terminus of the capture moiety is fused to the C-terminus of a signal sequence or peptide that enables the GPI-IgG capture moiety fusion protein to be transported through the secretory pathway to the cell surface where the GPI-IgG capture moiety fusion protein is secreted and then bound to the cell surface. In some aspects, the GPI-IgG capture moiety fusion protein comprises the entire GPI protein and in other aspects, the GPI-IgG capture moiety fusion protein comprises the portion of the GPI protein that is capable of binding to the cell surface.

The immunoglobulin capture moiety can comprise any molecule that can bind to an immunoglobulins. A multitude of Gram-positive bacteria species have been isolated that express surface proteins with affinities for mammalian immunoglobulins through interaction with their heavy chains. The best known of these immunoglobulin binding proteins are type 1 *Staphylococcus* Protein A and type 2 *Streptococcus* Protein G which have been shown to interact principally through the C2-C3 interface on the Fc region of human immunoglobulins. In addition, both have also been shown to interact weakly to the Fab region, but again through the immunoglobulin heavy chain.

Recently, a novel protein from Peptococcusmagnums, Protein L, has been reported that was found to bind to human, rabbit, porcine, mouse, and rat immunoglobulins uniquely through interaction with their light chains. In humans this interaction has been shown to occur exclusively to the kappa chains. Since both kappa and lambda light chains are shared between different classes, Protein L binds strongly to all human classes, in particular to the multi-subunit IgM, and similarly is expected to bind to all classes in species that show Protein L light chain binding.

Examples of other binding moieties, include but are not limited to, Fc receptor (FcR) proteins and immunoglobulin-binding fragments thereof. The FCR proteins include members of the Fc gamma receptor (FcγR) family, which bind gamma immunoglobulin (IgG), Fe epsilon receptor (FcεR) family, which bind epsilon immunoglobulin (IgE), and Fc alpha receptor (FcαR) family, which bind alpha immunoglobulin (IgA). Particular FcR proteins that bind IgG and can be used to comprise the capture moiety disclosed herein include at least the immunoglobulin binding portion of any one of FcγRI, FcγRIIA, FEcγRIIB1, FcγRIIB2, FcγRIIIA, FcγRIIB13, or FcγRn (neonatal).

Regulatory sequences which may be used in the practice of the methods disclosed herein include signal sequences, promoters, and transcription terminator sequences. It is generally preferred that the regulatory sequences used be from a species or genus that is the same as or closely related to that of the host cell or is operational in the host cell type chosen. Examples of signal sequences include those of *Saccharomyces cerevisiae* invertase; the *Aspergillus niger* amylase and glucoamylase; human serum albumin; *Kluyveromyces maxianus* inulinase; and *Pichia pastoris* mating factor and Kar2. Signal sequences shown herein to be useful in yeast and filamentous fungi include, but are not limited to, the alpha mating factor presequence and preprosequence from *Saccharomyces cerevisiae*; and signal sequences from numerous other species.

Examples of promoters include promoters from numerous species, including but not limited to alcohol-regulated promoter, tetracycline-regulated promoters, steroid-regulated promoters (e.g., glucocorticoid, estrogen, ecdysone, retinoid, thyroid), metal-regulated promoters, pathogen-regulated promoters, temperature-regulated promoters, and light-regulated promoters. Specific examples of regulatable promoter systems well known in the art include but are not limited to metal-inducible promoter systems (e.g., the yeast copper-metallothionein promoter), plant herbicide safner-activated promoter systems, plant heat-inducible promoter systems, plant and mammalian steroid-inducible promoter systems, Cym repressor-promoter system (Krackeler Scientific, Inc. Albany, NY), RheoSwitch System (New England Biolabs, Beverly MA), benzoate-inducible promoter systems (See WO2004/043885), and retroviral-inducible promoter systems. Other specific regulatable promoter systems well-known in the art include the tetracycline-regulatable systems (See for example, Berens & Hillen, Eur J Biochem 270: 3109-3121 (2003)), RU 486-inducible systems, ecdysone-inducible systems, and kanamycin-regulatable system. Lower eukaryote-specific promoters include but are not limited to the *Saccharomyces cerevisiae* TEF-1 promoter, *Pichia pastoris* GAPDH promoter, *Pichia pastoris* GUT1 promoter, PMA-1 promoter, *Pichia pastoris* PCK-1 promoter, and *Pichia pastoris* AOX-1 and AOX-2 promoters. For temporal expression of the GPI-IgG capture moiety and the immunoglobulins, the *Pichia pastoris* GUT1 promoter operably linked to the nucleic acid molecule encoding the GPI-IgG capture moiety and the *Pichia pastoris* GAPDH promoter operably linked to the nucleic acid molecule encoding the immunoglobulin are shown in the examples herein to be useful.

Examples of transcription terminator sequences include transcription terminators from numerous species and proteins, including but not limited to the *Saccharomyces cerevisiae* cytochrome C terminator; and *Pichia pastoris* ALG3 and PMA1 terminators.

Nucleic acid molecules encoding immunoglobulins can be obtained from any suitable source including spleen and liver cells and antigen-stimulated antibody producing cells, obtained from either in vivo or in vitro sources. Regardless of source, the cellular VH and VL mRNAs are reverse transcribed into VH and VL cDNA sequences. Reverse transcription may be performed in a single step or in an optional combined reverse transcription/PCR procedure to produce cDNA libraries containing a plurality of immunoglobulin-encoding DNA molecules. (See, for example, Marks et al., J. Mol. Biol. 222: 581-596 (1991)). Nucleic acid molecules can also be synthesized de novo based on sequences in the scientific literature. Nucleic acid molecules can also be synthesized by extension of overlapping oligonucleotides spanning a desired sequence (See, e.g., Caldas et al., Protein Engineering, 13: 353-360 (2000)). Humanized immunoglobulin-encoding cDNA libraries can be constructed by PCR amplifying the complementary-determining regions (CDR) from the cDNAs in one or more libraries from any source and integrating the PCR amplified CDR-encoding nucleic acid molecules into nucleic acid molecules encoding a human immunoglobulin framework to produce a cDNA library encoding a plurality of humanized immunoglobulins (See, for example, U.S. Pat. Nos. 6,180,370; 6,632,927; and, 6,872,392). Chimeric immunoglobulin-encoding cDNA libraries can be constructed by PCR amplifying the variable regions from the cDNAs in the cDNA library from one species and integrating the nucleic acid molecules encoding the PCR-amplified variable regions onto nucleic acid molecules encoding immunoglobulin constant regions from another species to produce a cDNA library encoding a plurality of chimeric immunoglobulins (See, for example, U.S. Pat. No. 5,843,708). Various methods that have been developed for the creation of diversity within protein libraries, including random mutagenesis (Daugherty et al., Proc. Natl Acad. Sci. USA, 97, 2029-2034 (2000); Boder et al., Proc. Natl Acad. Sci. USA, 97, 10701-10705 (2000); Holler et al., Proc. Natl Acad. Sci. USA, 97, 5387-5392 (2000)), in vitro DNA shuffling (Stemmer, Nature, 370, 389-391 (1994); Stemmer, Proc. Natl Acad.

Sci. USA, 91, 10747-10751 (1994)), in vivo DNA shuffling (Swers et al., Nucl. Acid Res. 32: e36 (2004)), and site-specific recombination (Rehberg et al., J. Biol. Chem., 257, 11497-11502 (1982); Streuli et al., Proc. Natl Acad. Sci. USA, 78, 2848-2852 (1981); Waterhouse et al., (1993) Nucl. Acids Res., 21, 2265-2266 (1993); Sblattero & Bradbury, Nat. Biotechnol., 18, 75-80 (2000)) can be used or adapted to produce the plurality of host cells disclosed herein that express immunoglobulins and the capture moiety comprising a cell surface anchoring protein fused to a binding moiety that is capable of specifically binding an immunoglobulin.

Production of active immunoglobulins requires proper folding of the protein when it is produced and secreted by the cells. In *E. coli*, the complexity and large size of an antibody presents an obstacle to proper folding and assembly of the expressed light and heavy chain polypeptides, resulting in poor yield of intact antibody. The presence of effective molecular chaperone proteins may be required, or may enhance the ability of the cell to produce and secrete properly folded proteins. The use of molecular chaperone proteins to improve production of immunoglobulins in yeast has been disclosed in U.S. Pat. Nos. 5,772,245; 5,700,678 and 5,874,247; U.S. Application Publication No. 2002/0068325; Toman et al., J. Biol. Chem. 275: 23303-23309 (2000); Keizer-Gunnink et al., Martix Biol. 19: 29-36 (2000); Vad et al., J. Biotechnol. 116: 251-260 (2005); Inana et al., Biotechnol. Bioengineer. 93: 771-778 (2005); Zhang et al., Biotechnol. Prog. 22: 1090-1095 (2006); Damasceno et al., Appl. Microbiol. Biotechnol. 74: 381-389 (2006); Huo et al., Protein Express. Purif. 54: 234-239 (2007); and copending application Ser. No. 61/066,409, filed 20 Feb. 2008.

As used herein, the methods can use host cells from any kind of cellular system which can be modified to express a capture moiety comprising a cell surface anchoring protein fused to a binding moiety capable of binding an immunoglobulin and whole, intact immunoglobulins. Within the scope of the invention, the term "cells" means the cultivation of individual cells, tissues, organs, insect cells, avian cells, reptilian cells, mammalian cells, hybridoma cells, primary cells, continuous cell lines, stem cells, plant cells, yeast cells, filamentous fungal cells, and/or genetically engineered cells, such as recombinant cells expressing and displaying a glycosylated immunoglobulin.

In a further embodiment, lower eukaryotes such as yeast or filamentous fungi are used for expression and display of the immunoglobulins because they can be economically cultured, give high yields, and when appropriately modified are capable of suitable glycosylation. Yeast particularly offers established genetics allowing for rapid transfections, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

Host cells useful in the present invention include *Pichia pastoris, Pichia finlandica, Pichia trehalophila, Pichia koclamae, Pichia membranaefaciens, Pichia minuta (Ogataea minuta, Pichia lindneri), Pichia opunliae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa*. Various yeasts, such as *K. lactis, Pichia pastoris, Pichia methanolica*, and *Hansenula polymorpha* are particularly suitable for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale. In the case of lower eukaryotes, cells are routinely grown from between about 1.5 to 3 days under conditions that induce expression of the capture moiety. The induction of immunoglobulin expression while inhibiting expression of the capture moiety is for about 1 to 2 days. Afterwards, the cells are analyzed for those cells that display the immunoglobulin of interest.

Lower eukaryotes, particularly yeast and filamentous fungi, can be genetically modified so that they express glycoproteins in which the glycosylation pattern is human-like or humanized. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in US 2004/0018590. If desired, additional genetic engineering of the glycosylation can be performed, such that the glycoprotein can be produced with or without core fucosylation. Use of lower eukaryotic host cells is further advantageous in that these cells are able to produce highly homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition.

Lower eukaryotes, particularly yeast, can be genetically modified so that they express glycoproteins in which the glycosylation pattern is human-like or humanized. Such can be achieved by eliminating selected endogenous glycosylation enzymes and/or supplying exogenous enzymes as described by Gerngross et al., US 20040018590. For example, a host cell can be selected or engineered to be depleted in 1,6-mannosyl transferase activities, which would otherwise add mannose residues onto the N-glycan on a glycoprotein.

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a Man5GlcNAc2 glycoform, for example, a recombinant glycoprotein composition comprising predominantly a $Man_5GlcNAc_2$ glycoform. For example, U.S. Pat. No. 7,029,872 and U.S. Published Patent Application Nos. 2004/0018590 and 2005/0170452 disclose lower eukaryote host cells capable of producing a glycoprotein comprising a Man5GlcNAc2 glycoform.

In a further embodiment, the immediately preceding host cell further includes a GlcNAc transferase I (GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a GlcNAcMan$_5$GlcNAc$_2$ glycoform, for example a recombinant glycoprotein composition comprising predominantly a GlcNAcMan$_5$GlcNAc$_2$ glycoform. U.S. Pat. No. 7,029,872 and U.S. Published Patent Application Nos. 2004/0018590 and 2005/0170452 disclose lower eukaryote host cells capable of producing a glycoprotein comprising a GlcNAcMan$_5$GlcNAc$_2$ glycoform. The glycoprotein produced in the above cells can be treated in vitro with a hexaminidase to produce a recombinant glycoprotein comprising a Man$_5$GlcNAc$_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a GlcNAcMan$_3$GlcNAc$_2$ glycoform, for example a recombinant glycoprotein composition comprising predominantly a GlcNAcMan$_3$GlcNAc$_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a GlcNAc2Man3GlcNAc2 glycoform. The glycoprotein produced in the above cells can be treated in vitro with a hexaminidase to produce a recombinant glycoprotein comprising a Man3GlcNAc2 glycoform.

In a further embodiment, the immediately preceding host cell further includes GlcNAc transferase II (GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform. U.S. Pat. No. 7,029,872 and U.S. Published Patent Application Nos. 2004/0018590 and 2005/0170452 disclose lower eukaryote host cells capable of producing a glycoprotein comprising a GlcNAc2Man3GlcNAc2 glycoform. The glycoprotein produced in the above cells can be treated in vitro with a hexaminidase to produce a recombinant glycoprotein comprising a Man$_3$GlcNAc$_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a GalGlcNAc$_2$Man$_3$GlcNAc$_2$ or Gal$_2$GlcNAc$_2$Man$_3$GlcNAc$_2$ glycoform, or mixture thereof for example a recombinant glycoprotein composition comprising predominantly a GalGlcNAc$_2$Man$_3$GlcNAc$_2$ glycoform or Gal$_2$GlcNAc$_2$Man$_3$GlcNAc$_2$ glycoform or mixture thereof. U.S. Pat. No. 7,029,872 and U.S. Published Patent Application No. 2006/0040353 discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialtransferase activity to the ER or Golgi apparatus of the host cell. Passage of the recombinant glycoprotein through the ER or Golgi apparatus of the host cell produces a recombinant glycoprotein comprising predominantly a NANA$_2$Gal$_2$GlcNAc2Man$_3$GlcNAc$_2$ glycoform or NANAGal$_2$GlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX)N-glycan structures such as disclosed in U.S. Published Patent Application Nos. 2004/074458 and 2007/0037248.

In further embodiments, the host cell that produces glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target Galactosyltransferase activity to the ER or Golgi apparatus of the host cell. Passage of the recombinant glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising a NANAGalGlcNAcMan$_5$GlcNAc$_2$ glycoform.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include lower eukaryote cells (e.g., yeast such as *Pichia pastoris*) that are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Published Patent Application No. 2006/0211085) and glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377) or grown in the presence of Pmtp inhibitors and/or an alpha-mannosidase as disclosed in Published International Application No. WO 2007061631, or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted alpha-1,2-mannosidase.

PMT deletions or disruptions and/or Pmtp inhibitors control O-glycosylation by reducing O-glycosylation occupancy, that is by reducing the total number of O-glycosylation sites on the glycoprotein that are glycosylated. The further addition of an alpha-1,2-mannsodase that is secreted by the cell controls O-glycosylation by reducing the mannose chain length of the O-glycans that are on the glycoprotein. Thus, combining PMT deletions or disruptions and/or Pmtp inhibitors with expression of a secreted alpha-1,2-mannosidase controls O-glycosylation by reducing occupancy and chain length. In particular circumstances, the particular combination of PMT deletions or disruptions, Pmtp inhibitors, and alpha-1,2-mannosidase is determined empirically as particular heterologous glycoproteins (antibodies, for example) may be expressed and transported through the Golgi apparatus with different degrees of efficiency and thus may require a particular combination of PMT deletions or disruptions, Pmtp inhibitors, and alpha-1,2-mannosidase. In another aspect, genes encoding one or more endogenous mannosyltransferase enzymes are deleted. This deletion(s) can be in combination with providing the secreted alpha-1,2-mannosidase and/or PMT inhibitors or can be in lieu of providing the secreted alpha-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of whole antibodies as they traverse the secretory pathway and are transported to the cell surface. Thus, in cells in which O-glycosylation is controlled, the yield of properly assembled antibodies fragments is increased over the yield obtained in host cells in which O-glycosylation is not controlled.

In addition, O-glycosylation may have an effect on an antibody's affinity and/or avidity for an antigen. This can be particularly significant when the ultimate host cell for production of the antibody is not the same as the host cell that was used for selecting the antibody. For example, O-glycosylation might interfere with an antibody's affinity for an antigen, thus an antibody that might otherwise have high affinity for an antigen might not be identified because O-glycosylation may interfere with the ability of the antibody to bind the antigen. In other cases, an antibody that has high avidity for an antigen might not be identified because O-glycosylation interferes with the antibody's avidity for the antigen. In the preceding two cases, an antibody that might be particularly effective when produced in a mammalian cell line might not be identified because the host cells for identifying and selecting the antibody was of another cell type, for example, a yeast or fungal cell (e.g., a *Pichia pastoris* host cell). It is well known that O-glycosylation in yeast can be significantly different from O-glycosylation in mammalian cells. This is particularly relevant when comparing wild type yeast o-glycosylation with mucin-type or dystroglycan type O-glycosylation in mammals. In particular cases, O-glycosylation might enhance the antibody's affinity or avidity for an antigen instead of interfere. This effect is undesirable when the production host cell is to be different from the host cell used to identify and select the antibody (for example, identification and selection is done in yeast and the production host is a mammalian cell) because in the production host the O-glycosylation will no longer be of the type that caused the enhanced affinity or avidity for the antigen. Therefore, controlling 0-glycosylation can enable use of the materials and methods herein to identify and select antibodies with specificity for a particular antigen based upon affinity or avidity of the antibody for the antigen without identification and selection of the antibody being influenced by the O-glycosylation system of the host cell. Thus, controlling O-glycosylation further enhances the usefulness of yeast or fungal host cells to identify and select antibodies that will ultimately be produced in a mammalian cell line.

Yield of antibodies can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in U.S. Provisional Application Nos. 61/066,409 filed Feb. 20, 2008 and 61/188,723 filed Aug. 12, 2008. Like above, further included are lower eukaryotic host cells wherein, in addition to replacing the genes encoding one or more of the endogenous chaperone proteins with nucleic acid molecules encoding one or more mammalian or human chaperone proteins or overexpressing one or more mammalian or human chaperone proteins as described above, the function or expression of at least one endogenous gene encoding a protein O-mannosyltransferase (PMT) protein is reduced, disrupted, or deleted. In particular embodiments, the function of at least one endogenous PMT gene selected from the group consisting of the PMT1, PMT2, PMT3, and PMT4 genes is reduced, disrupted, or deleted.

Therefore, the methods disclose herein can use any host cell that has been genetically modified to produce glycoproteins that have no N-glycans compositions wherein the predominant N-glycan is selected from the group consisting of complex N-glycans, hybrid N-glycans, and high mannose N-glycans wherein complex N-glycans are selected from the group consisting of $Man_3GlcNAc_2$, $GlcNAC_{(1-4)}Man_3GlcNAc_2$, $Gal_{(1-4)}GlcNAc_{(1-4)}Man_3GlcNAc_2$, and $NANA(i-4)Gal(1\_4)Man_3GlcNAc_2$; hybrid N-glycans are selected from the group consisting of $Man_5GlcNAc_2$, $GlcNAcMan_5GlcNAc_2$, $GalGlcNAcManSGlcNAc_2$, and $NANAGalGlcNAcMan_5GlcNAc_2$; and high Mannose N-glycans are selected from the group consisting of $Man_6GlcNAc_2$, $Man_7GlcNAc_2$, $Man_8GlcNAc_2$, and $Man_9GlcNAc_2$. In particular aspects, the composition of N-glycans comprises about 39% $GlcNAC_2Man_3GlcNAc_2$; 40% $Gal_1GlcNAC_2Man_3GlcNAc_2$; and 6% $Gal_2GlcNAC_2Man_3GlcNAc_2$ or about 60% $GlcNAC_2Man_3GlcNAc_2$; 17% $Gal_1GlcNAC_2Man_3GlcNAc_2$; and 5% $Gal_2GlcNAC_2Man_3GlcNAc_2$, or mixtures in between.

In the above embodiments in which the yeast cell does not display 1,6-mannosyl transferase activity (that is, the OCH1 gene encoding och1p has been disrupted or deleted), the host cell is not capable of mating. Thus, depending on the efficiency of transformation, the potential library diversity of light chains and heavy chains appears to be limited to a heavy chain library of between about 103 to 106 diversity and a light chain library of about 103 to 106 diversity. However, in a yeast host cell that is capable of mating, the diversity can be increased to about 106 to 1012 because the host cells expressing the heavy chain library can be mated to host cells expressing the light chain library to produce host cells that express heavy chain/light chain library. Therefore, in particular embodiments, the host cell is a yeast cell such as *Pichia pastoris* that displays 1,6-mannosyl transferase activities (that is, has an OCH1 gene encoding a function och1p) but which is modified as described herein to display antibodies or fragments thereof on the cell surface. In these embodiments, the host cell can be a host cell with its native glycosylation pathway.

Yeast selectable markers that can be used in the present invention include drug resistance markers and genetic functions which allow the yeast host cell to synthesize essential cellular nutrients, e.g. amino acids. Drug resistance markers which are commonly used in yeast include chloramphenicol, kanamycin, methotrexate, G418 (geneticin), Zeocin, and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et at., Yeast, 13:819-828 (1997); Wysocki et al., J. Biol. Chem. 272: 30061-30066 (1997)). A number of suitable integration sites include those enumerated in U.S. Published application No. 2007/0072262 and include homologs to loci known for *Saccharomyces cerevisiae* and other yeast or fungi. Methods for integrating vectors into yeast are well known, for example, see U.S. Pat. No. 7,479,389, WO2007136865, and PCT/US2008/13719. Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700, the HIS3 and TRP1 genes have been described in Cosano et al., Yeast 14:861-867 (1998), HIS4 has been described in GenBank® Accession No. X56180. In embodiments that express whole antibodies, the nucleic acid molecule encoding the antibody or heavy chain fragment thereof is modified to replace the codon encoding an asparagine residue at position 297 of the molecule (the glycosylation site) with a codon encoding any other amino acid residue. Thus, the antibody that is produced in the host cell is not glycosylated. In this embodiment, the host cell displaying the heavy chain library is mated to the host cell displaying the light chain library and the resulting combinatorial library is screened as taught herein. Because the antibodies lack N-glycosylation, the non-human yeast N-glycans of the host cell which might interfere with antibody affinity for a desired antigen are not present on the recombinant antibodies. Cells producing antibodies that have desired affinity for an antigen of interest are selected. The nucleic acid molecules encoding the heavy and light chains of the antibody thereof are removed from the cells and the nucleic acid molecule encoding the heavy chain is modified to reintroduce an asparagine residue at position 297. This enables appropriate human-like glycosylation at position 297 of the antibody or fragment thereof when the nucleic acid molecule encoding the antibody thereof is introduced into a host cell that has been engineered to make glycoproteins that have hybrid or complex N-glycans as discussed previously.

The cell systems used for recombinant expression and display of the immunoglobulin can also be any higher eukaryote cell, tissue, organism from the animal kingdom, for example transgenic goats, transgenic rabbits, CHO cells, insect cells, and human cell lines. Examples of animal cells include, but are not limited to, SC-I cells, LLC-MK cells, CV-I cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0, NSO cells, and derivatives thereof. Insect cells include cells of *Drosophila melanogaster* origin. These cells can be genetically engineered to render the cells capable of making immunoglobulins that have particular or predominantly particular N-glycans. For example, U.S. Pat. No. 6,949,372 discloses methods for making glycoproteins in insect cells that are sialylated. Yamane-Ohnuki et al. Biotechnol. Bioeng. 87: 614-622 (2004), Kanda et al., Biotechnol. Bioeng. 94: 680-688 (2006), Kanda et al., Glycobiol. 17: 104-118 (2006), and U.S. Pub. Application Nos. 2005/0216958 and 2007/0020260 disclose mammalian cells that are capable of producing immunoglobulins in which the N-glycans thereon lack fucose or have reduced fucose.

In particular embodiments, the higher eukaryote cell, tissue, organism can also be from the plant kingdom, for example, wheat, rice, corn, tobacco, and the like. Alternatively, bryophyte cells can be selected, for example from species of the genera *Physcomitrella, Funaria, Sphagnum, Ceratodon, Marchantia*, and *Sphaerocarpos*. Exemplary of plant cells is the bryophyte cell of *Physcomitrella patens*, which has been disclosed in WO 2004/057002 and WO2008/006554. Expression systems using plant cells can further manipulated to have altered glycosylation pathways to enable the cells to produce immunoglobulins that have predominantly particular N-glycans. For example, the cells can be genetically engineered to have a dysfunctional or no core fucosyltransferase and/or a dysfunctional or no xylosyltransferase, and/or a dysfunctional or no β1,4-galactosyltransferase. Alternatively, the galactose, fucose and/or xylose can be removed from the immunoglobulin by treatment with enzymes removing the residues. Any enzyme resulting in the release of galactose, fucose and/or xylose residues from N-glycans which are known in the art can be used, for example α-galactosidase, β-xylosidase, and α-fucosidase. Alternatively an expression system can be used which synthesizes modified N-glycans which can not be used as substrates by 1,3-fucosyltransferase and/or 1,2-xylosyltransferase, and/or 1,4-galactosyltransferase. Methods for modifying glycosylation pathways in plant cells has been disclosed in U.S. Published Application No. 2004/0018590.

The methods disclosed herein can be adapted for use in mammalian, insect, and plant cells. The regulatable promoters selected for regulating expression of the expression cassettes in mammalian, insect, or plant cells should be selected for functionality in the cell-type chosen. Examples of suitable regulatable promoters include but are not limited to the tetracycline-regulatable promoters (See for example, Berens & Hillen, Eur. J. Biochem. 270: 3109-3121 (2003)), RU 486-inducible promoters, ecdysone-inducible promoters, and kanamycin-regulatable systems. These promoters can replace the promoters exemplified in the expression cassettes described in the examples. The capture moiety can be fused to a cell surface anchoring protein suitable for use in the cell-type chosen. Cell surface anchoring proteins including GPI proteins are well known for mammalian, insect, and plant cells. GPI-anchored fusion proteins has been described by Kennard et al., Methods Biotechnol. Vo. 8: Animal Cell Biotechnology (Ed. Jenkins. Human Press, Inc., Totowa, NJ) pp. 187-200 (1999). The genome targeting sequences for integrating the expression cassettes into the host cell genome for making stable recombinants can replace the genome targeting and integration sequences exemplified in the examples. Transfection methods for making stable and transiently transfected mammalian, insect, plant host cells are well known in the art. Once the transfected host cells have been constructed as disclosed herein, the cells can be screened for expression of the immunoglobulin of interest and selected as disclosed herein.

The present invention also encompasses kits containing the expression and helper vectors of this invention in suitable packaging. Each kit necessarily comprises the reagents which render the delivery of vectors into a host cell possible. The selection of reagents that facilitate delivery of the vectors may vary depending on the particular transfection or infection method used. The kits may also contain reagents useful for generating labeled polynucleotide probes or proteinaceous probes for detection of exogenous sequences and the protein product. Each reagent can be supplied in a solid form or dissolved/suspended in a liquid buffer suitable for inventory storage, and later for exchange or addition into the reaction medium when the experiment is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

All publications, patents, and other references mentioned herein are hereby incorporated by reference in their entireties.

The following examples are intended to promote a further understanding of the present invention.

Example 1

Utility of the invention was demonstrated using *Pichia pastoris* as a model. The glycoengineered *Pichia pastoris* strain yGLY2696 was the background strain used. In strain yGLY2696, the gene encoding the endogenous PDI replaced with a nucleic acid molecule encoding the human PDI and a nucleic acid molecule encoding the human GRP94 protein inserted into the PEP4 locus. The strain was further engineered to alter the endogenous glycosylation pathway to produce glycoproteins that have predominantly $Man_5GlcNAc_2$ N-glycans. Strain YGLY2696 has been disclosed in co-pending Application Ser. No. 61/066,409, filed 20 Feb. 2008. This strain was shown to be useful for producing immunoglobulins and for producing immunoglobulins that have reduced O-glycosylation.

Figure 8:
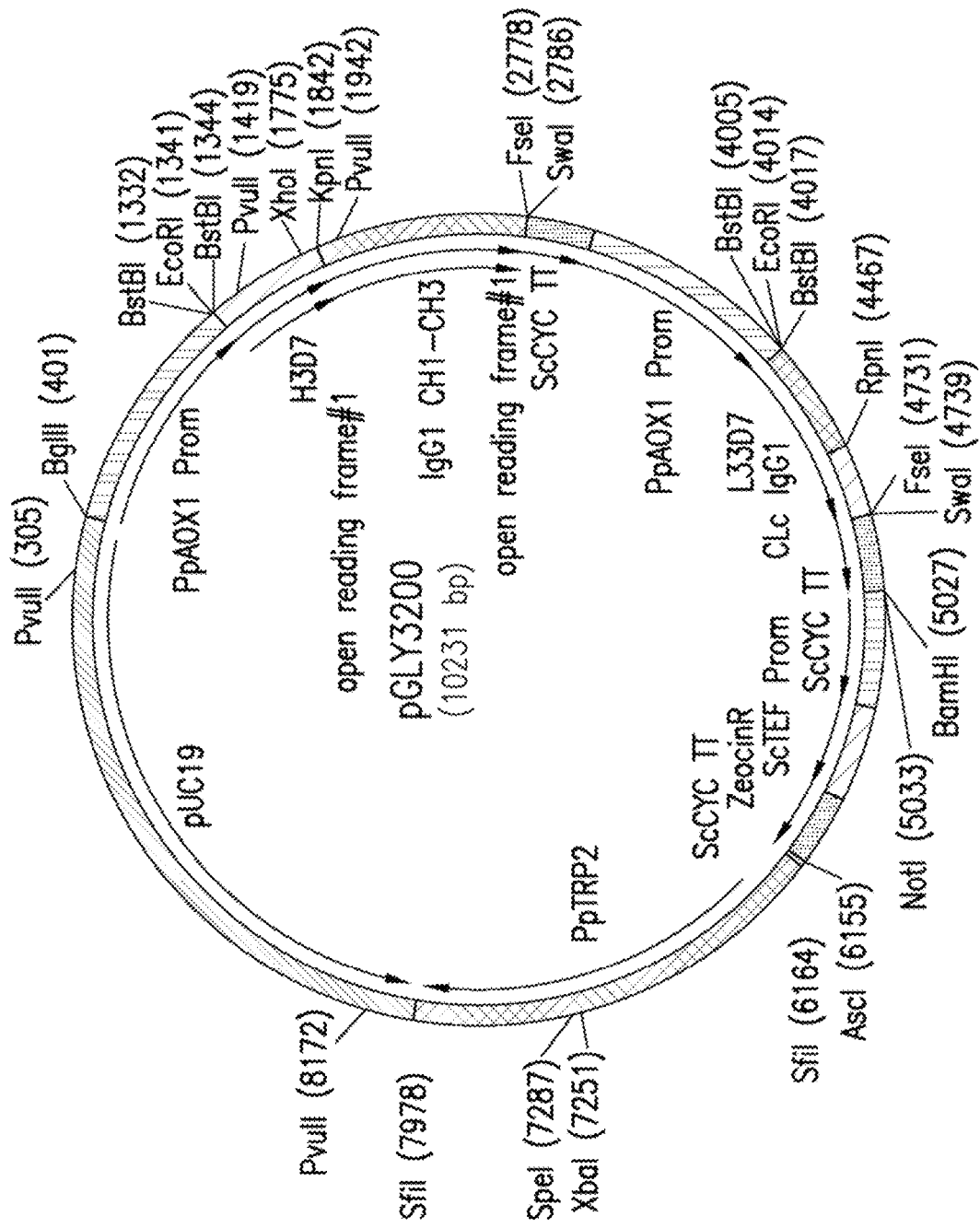
FIG. 8 shows a map of plasmid vector pGLY3200.

Construction of strain yGLY2696 involved the following steps. Construction of expression/integration plasmid vector pGLY642 comprising an expression cassette encoding the human PDI protein and nucleic acid molecules to target the plasmid vector to the *Pichia pastoris* PDI1 locus for replacement of the gene encoding the *Pichia pastoris* PDI/with a nucleic acid molecule encoding the human PDI was as follows and is shown in FIG. 8. cDNA encoding the human PDI1 was amplified by PCR using the primers hPDI/UP1: 5' AGCGC TGACG CCCCC GAGGA GGAGG ACCAC 3' (SEQ ID NO: 1) and hPDI/LP-PacI: 5' CCTTA ATTAA TTACA GTTCA TCATG CACAG CTTTC TGATC AT 3' (SEQ ID NO: 2), Pfu turbo DNA polymerase (Stratagene, La Jolla, CA), and a human liver cDNA (BD Bioscience, San Jose, CA). The PCR conditions were 1 cycle of 95° C. for two minutes, 25 cycles of 95° C. for 20 seconds, 58° C. for 30 seconds, and 72° C. for 1.5 minutes, and followed by one cycle of 72° C. for 10 minutes. The resulting PCR product was cloned into plasmid vector pCR2.1 to make plasmid vector pGLY618. The nucleotide and amino acid sequences of the human PDI1 (SEQ ID NOs:39 and 40, respectively) are shown in Table 1.

The nucleotide and amino acid sequences of the *Pichia pastoris* PDI1 (SEQ ID NOs:41 and 42, respectively) are shown in Table 1. Isolation of nucleic acid molecules comprising the *Pichia pastoris* PDI1 5' and 3' regions was performed by PCR amplification of the regions from *Pichia pastoris* genomic DNA. The 5' region was amplified using primers PB248: 5' ATGAA TTCAG GCCAT ATCGG CCATT GTTTA CTGTG CGCCC ACAGT AG 3' (SEQ ID NO: 3); PB249: 5' ATGTT TAAAC GTGAG GATTA CTGGT GATGA AAGAC 3' (SEQ ID NO: 4). The 3' region was amplified using primers PB250: 5' AGACT AGTCT ATTTG GAGAC ATTGA CGGAT CCAC 3' (SEQ ID NO: 5); PB251: 5' ATCTC GAGAG GCCAT GCAGG CCAAC CACAA GATGA ATCAA ATTTT G-3' (SEQ ID NO: 6). *Pichia pastoris* strain NRRL-11430 genomic DNA was used for PCR amplification. The PCR conditions were one cycle of 95° C. for two minutes, 25 cycles of 95° C. for 30 seconds, 55° C. for seconds, and 72° C. for 2.5 minutes, and followed by one cycle of 72° C. for 10 minutes. The resulting PCR fragments, PpPDI1 (5') and PpPDI1 (3'), were separately cloned into plasmid vector pCR2.1 to make plasmid vectors pGLY620 and pGLY617, respectively. To construct pGLY678, DNA fragments PpARG3-5' and PpARG-3' of integration plasmid vector pGLY24, which targets the plasmid vector to *Pichia pastoris* ARG3 locus, were replaced with DNA fragments PpPDI (5') and PpPDI (3'), respectively, which targets the plasmid vector pGLY678 to the PDI1 locus and disrupts expression of the PDI1 locus.

Figure 2A:
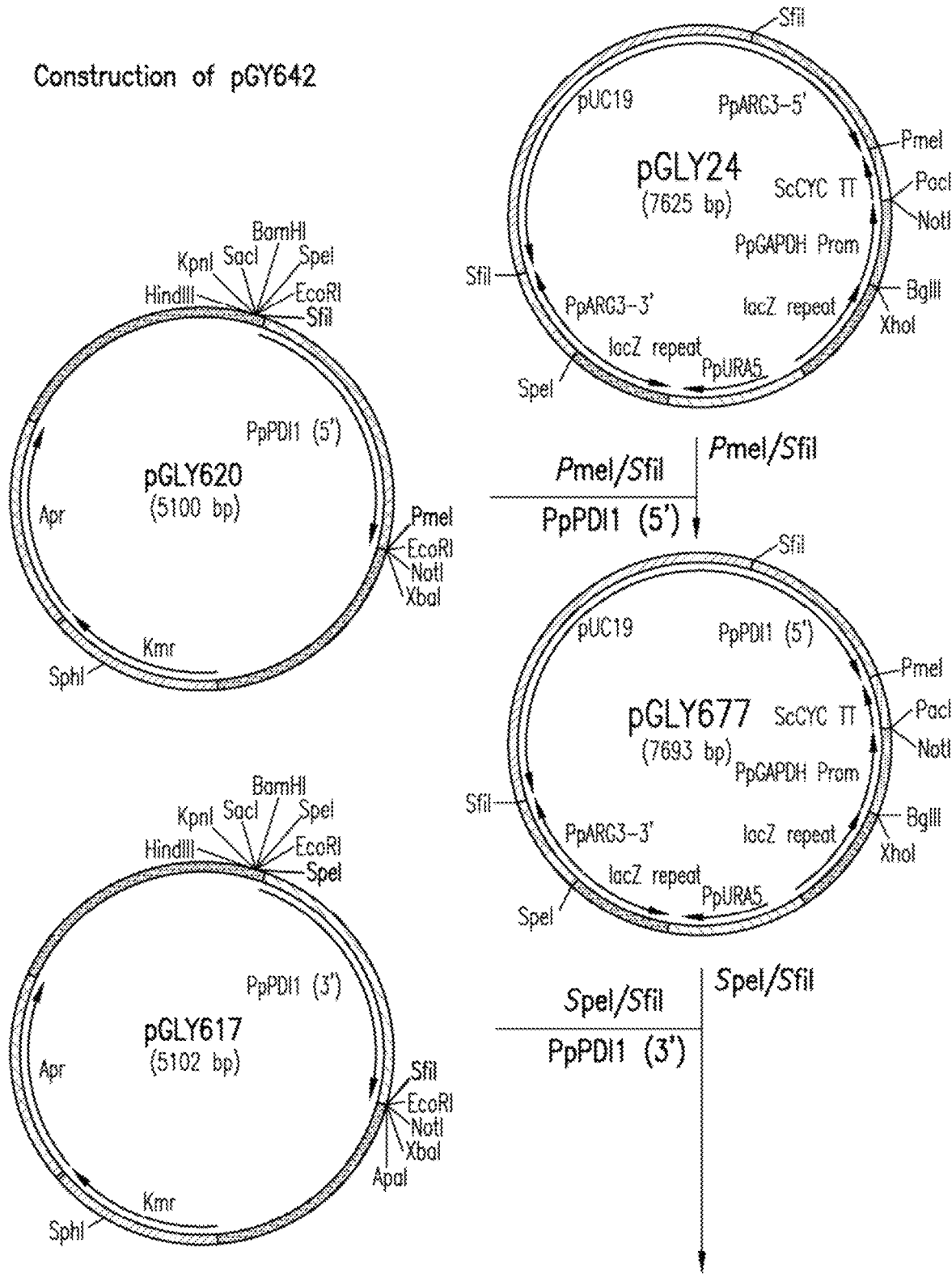
FIG. 2A and FIG. 2B illustrate the construction of plasmid vector pGLY642.
Figure 2B:
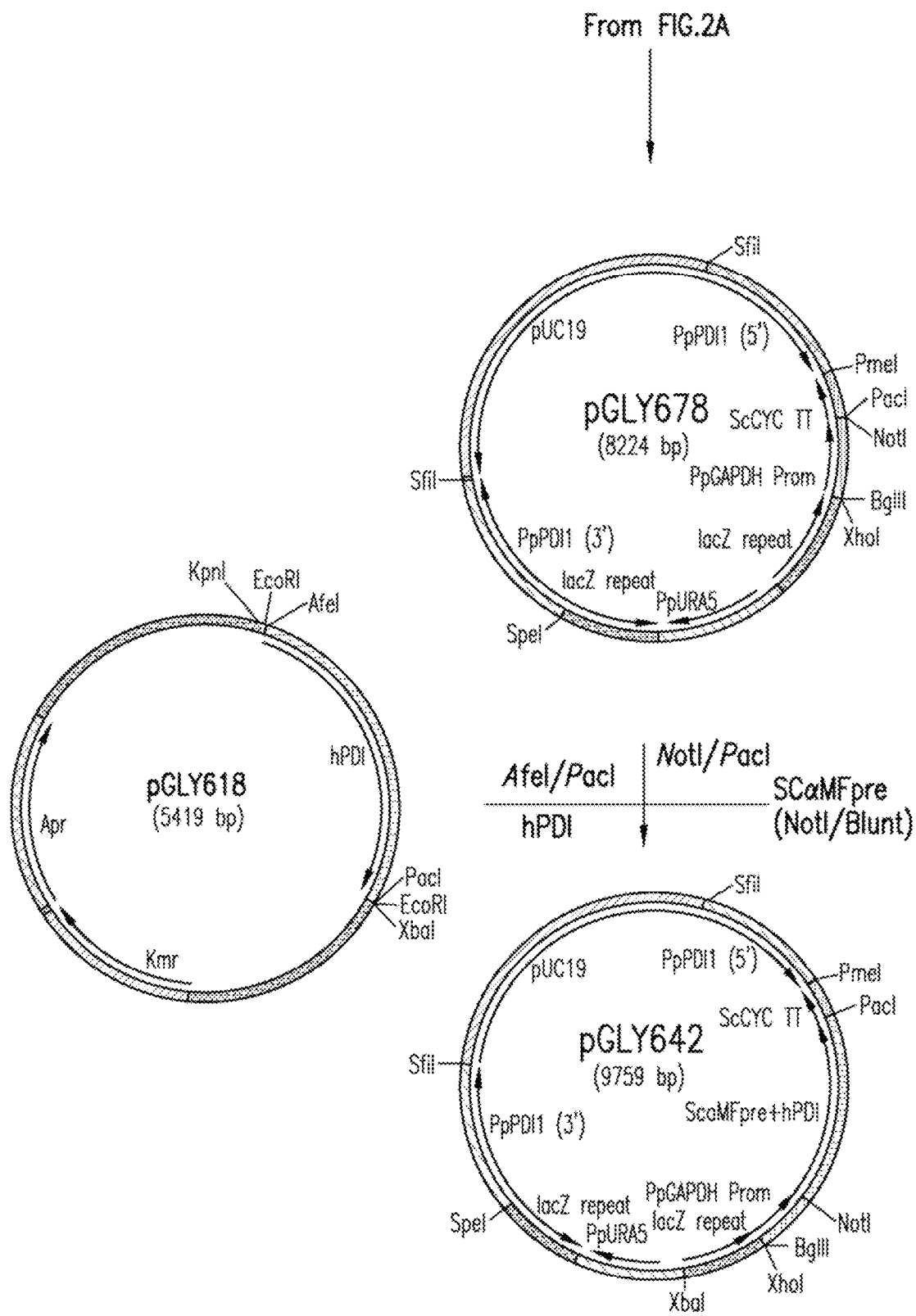

The nucleic acid molecule encoding the human PDI was then cloned into plasmid vector pGLY678 to produce plasmid vector pGLY642 in which the nucleic acid molecule encoding the human PDI was placed under the control of the *Pichia pastoris* GAPDH promoter (PpGAPDH). Expression/integration plasmid vector pGLY642 was constructed by ligating a nucleic acid molecule encoding the *Saccharomyces cerevisiae* alpha mating factor (MF) presequence signal peptide (Sc(MFpre-signal peptide) having a NoI restriction enzyme site at the 5' end and a blunt 3' end and the expression cassette comprising the nucleic acid molecule encoding the human PDI released from plasmid vector pGLY618 with AfeI and PacI to produce a nucleic acid molecule having a blunt 5' end and a PacI site at the 3' end into plasmid vector pGLY678 digested with NotI and PacI. The resulting integration/expression plasmid vector pGLY642 comprises an expression cassette encoding a human PDI1/ScaMFpre-signal peptide fusion protein operably linked to the *Pichia pastoris* promoter and nucleic acid molecule sequences to target the plasmid vector to the *Pichia pastoris* PDI1 locus for disruption of the PDI1 locus and integration of the expression cassette into the PDI1 locus. FIG. 2A and FIG. 2B illustrate the construction of plasmid vector pGLY642. The nucleotide and amino acid sequences of the ScαMFpre-signal peptide are shown in SEQ ID NOs:27 and 28, respectively.

Figure 3:
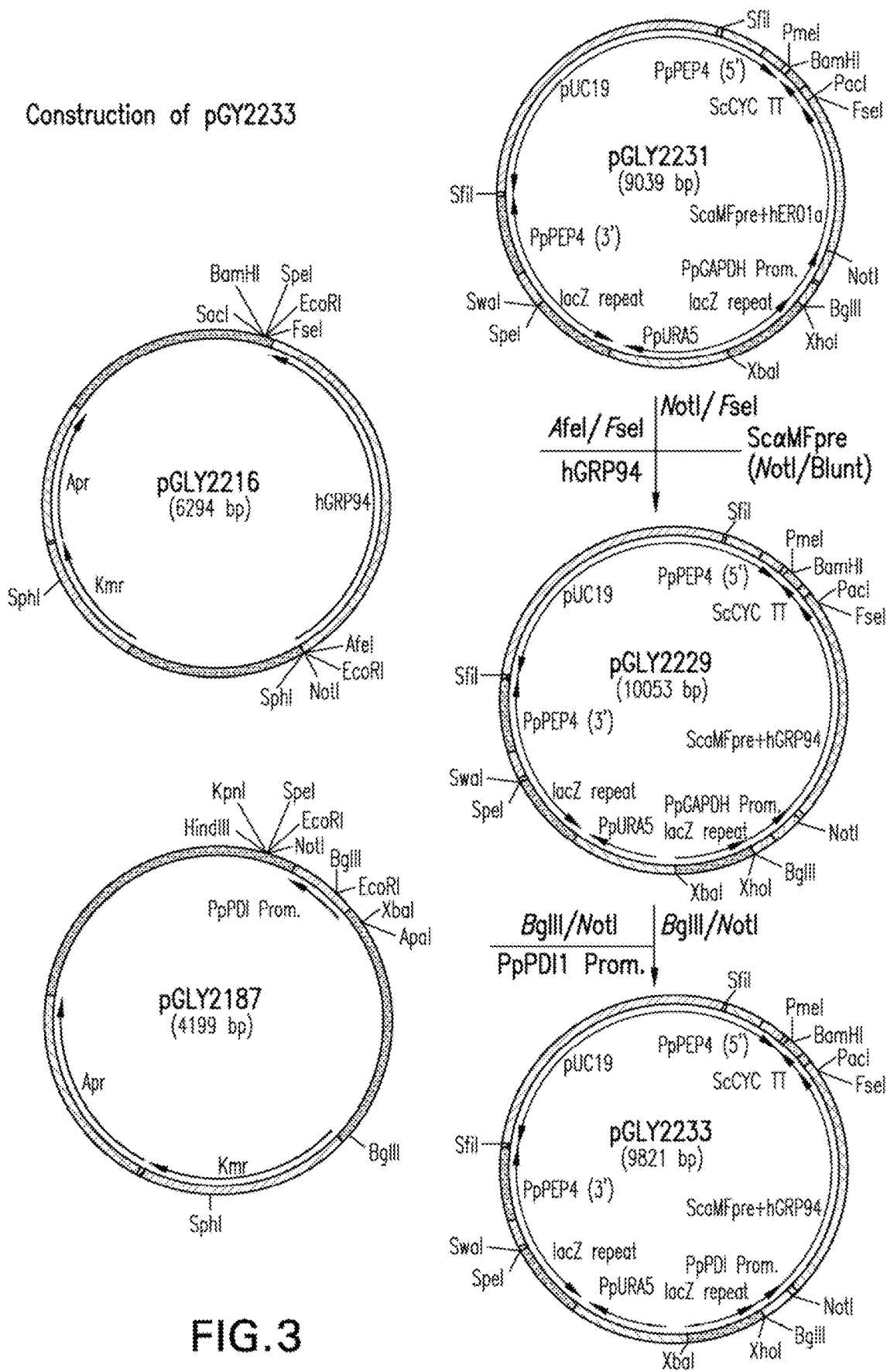
FIG. 3 illustrates the construction of plasmid vector pGLY2233

Construction of expression/integration vector pGLY2233 encoding the human GRP94 protein was as follows and is shown in FIG. 3. The human GRP94 was PCR amplified from human liver cDNA (BD Bioscience) with the primers hGRP94/UP1: 5'-AGCGC TGACG ATGAA GTTGA TGTGG ATGGT ACAGT AG-3'; (SEQ ID NO: 15); and hGRP94/LP1: 5'-GGCCG GCCTT ACAAT TCATC ATGTT CAGCT GTAGA TTC 3'; (SEQ ID NO: 16). The PCR conditions were one cycle of 95° C. for two minutes, 25 cycles of 95° C. for 20 seconds, 55° C. for 20 seconds, and 72° C. for 2.5 minutes, and followed by one cycle of 72° C. for 10 minutes. The PCR product was cloned into plasmid vector pCR2.1 to make plasmid vector pGLY2216. The nucleotide and amino acid sequences of the human GRP94 (SEQ ID NOs:43 and 44, respectively) are shown in Table 1.

The nucleic acid molecule encoding the human GRP94 was released from plasmid vector pGLY2216 with AfeI and FseI. The nucleic acid molecule was then ligated to a nucleic acid molecule encoding the ScαMPpre-signal peptide having NotI and blunt ends as above and plasmid vector pGLY2231 digested with NotI and FseI carrying nucleic acid molecules comprising the *Pichia pastoris* PEP4 5' and 3' regions (PpPEP4-5' and PpPEP4-3' regions, respectively) to make plasmid vector pGLY2229. Plasmid vector pGLY2229 was digested with BglII and NotI and a DNA fragment containing the PpPDI1 promoter was removed from plasmid vector pGLY2187 with BglII and NoII and the DNA fragment ligated into pGLY2229 to make plasmid vector pGLY2233. Plasmid vector pGLY2233 encodes the human GRP94 fusion protein under control of the *Pichia pastoris* PDI promoter and includes the 5' and 3' regions of the *Pichia pastoris* PEP4 gene to target the plasmid vector to the PEP4 locus of genome for disruption of the PEP4 locus and integration of the expression cassette into the PEP4 locus. FIG. 3 illustrates the construction of plasmid vector pGLY2233.

Construction of plasmid vectors pGLY1162, pGLY1896, and pGFI207t was as follows. All *Trichoderma reesei* α-1,2-mannosidase expression plasmid vectors were derived from pGFI165, which encodes the *T. reesei* α-1,2-mannosidase catalytic domain (See published International Application No. WO2007061631) fused to *S. cerevisiae* uMATpre signal peptide (ScαMPpre-signal peptide) herein expression is under the control of the *Pichia pastoris* GAP promoter and wherein integration of the plasmid vectors is targeted to the *Pichia pastoris* PRO1 locus and selection is using the *Pichia pastoris* URA5 gene. A map of plasmid vector pGFI165 is shown in FIG. 4A.

Figure 5:
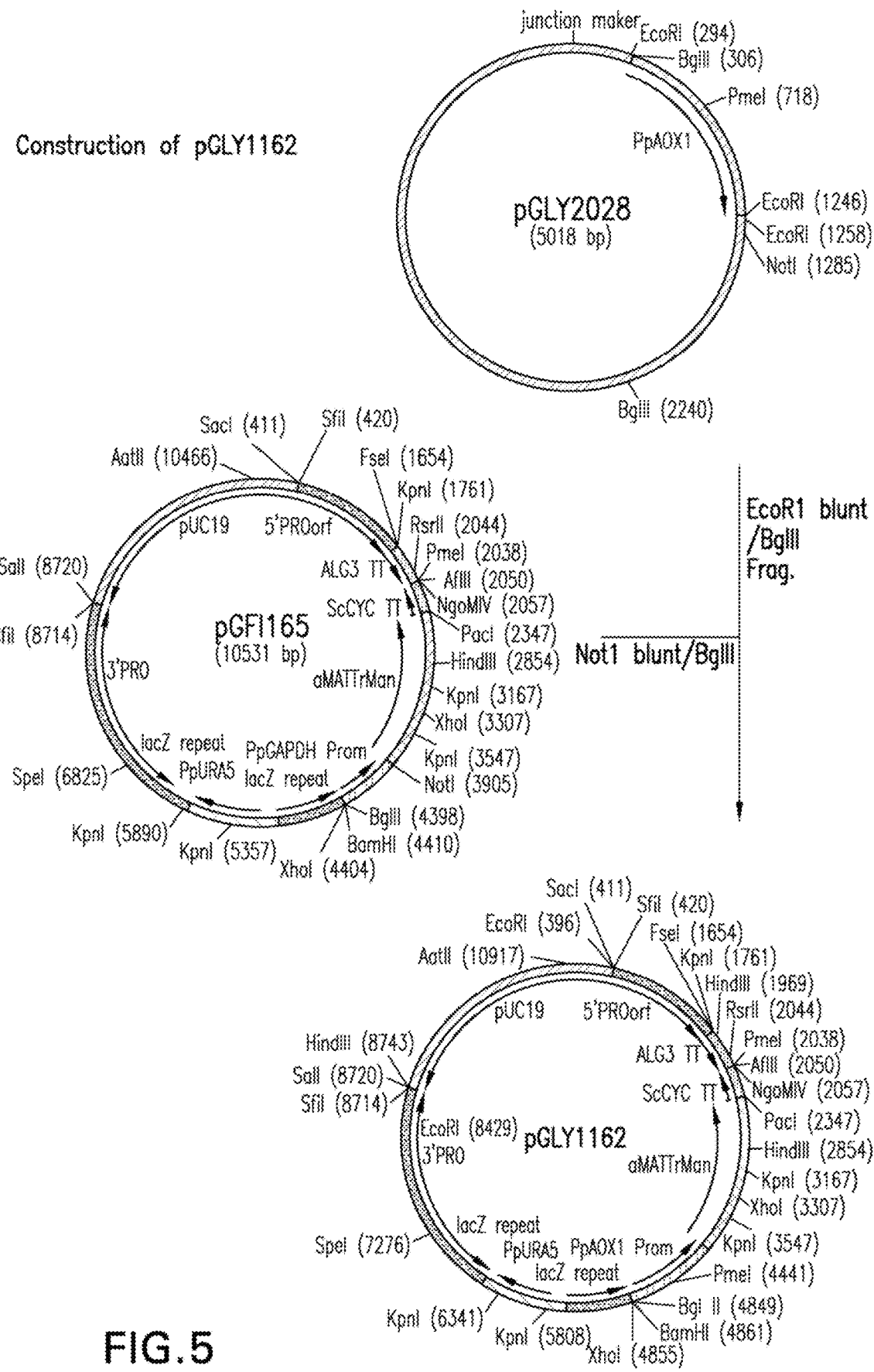
FIG. 5 illustrates the construction of plasmid vector pGLY1162.

Plasmid vector pGLY1162 was made by replacing the GAP promoter in pGFI165 with the *Pichia pastoris* AOX1 (PpAOX1) promoter. This was accomplished by isolating the PpAOX1 promoter as an EcoRI (made blunt)-BglII fragment from pGLY2028, and inserting into pGFII65 that was digested with NotI (made blunt) and BglII. Integration of the plasmid vector is to the *Pichia pastoris* PROJ locus and selection is using the *Pichia pastoris* URA5 gene. A map of plasmid vector pGLY1162 is shown in FIG. 5.

Plasmid vector pGLY1896 contains an expression cassette encoding the mouse α-1,2-mannosidase catalytic domain fused to the *S. cerevisiae* MNN2 membrane insertion leader peptide fusion protein (See Choi et al., Proc. Natl. Acad. Sci. USA 100: 5022 (2003)) inserted into plasmid vector pGFI165 (FIG. 5). This was accomplished by isolating the GAPp-ScMNN2-mouse MNSI expression cassette from pGLY1433 digested with XhoI (and the ends made blunt) and PmeI, and inserting the fragment into pGFI165 that digested with PmeI. Integration of the plasmid vector is to the *Pichia pastoris* PRO1 locus and selection is using the *Pichia pastoris* URA5 gene. A map of plasmid vector pGLY1896 is shown in FIG. 4A.

Plasmid vector pGFI207t is similar to pGLY1896 except that the URA5 selection marker was replaced with the *S. cerevisiae* ARR3 (ScARR3) gene, which confers resistance to arsenite. This is accomplished by isolating the ScARR3 gene from pGFI166 digested with AscI and the AscI ends made blunt) and BglII, and inserting the fragment into pGLY1896 that digested with SpeI and the SpeI ends made blunt and BglII. Integration of the plasmid vector is to the *Pichia pastoris* PROJ locus and selection is using the *Saccharomyces cerevisiae* ARR3 gene. A map of plasmid vector pGFI207t is shown in FIG. 4B. The ARR3 gene from *S. cerevisiae* confers arsenite resistance to cells that are grown in the presence of arsenite (Bobrowicz et al., Yeast, 13:819-828 (1997); Wysocki et al., J. Biol. Chem. 272: 30061-066 (1997)).

Yeast transfections with the above expression/integration vectors were as follows. *Pichia pastoris* strains were grown in 50 mL YPD media (yeast extract (1%), peptone (2%), dextrose (2%)) overnight to an OD of between about 0.2 to 6. After incubation on ice for 30 minutes, cells were pelleted by centrifugation at 2500-3000 rpm for 5 minutes. Media was removed and the cells washed three times with ice cold sterile 1 M sorbitol before resuspending in 0.5 ml ice cold sterile 1 M sorbitol. Ten μL linearized DNA (5-20 pg) and 100 μL cell suspension was combined in an electroporation cuvette and incubated for 5 minutes on ice. Electroporation was in a Bio-Rad GenePulser Xcell following the preset *Pichia pastoris* protocol (2 kV, 25 F, 200 Q), immediately followed by the addition of 1 mL YPDS recovery media (YPD media plus 1 M sorbitol). The transfected cells were allowed to recover for four hours to overnight at room temperature (26° C.) before plating the cells on selective media.

Figure 6:
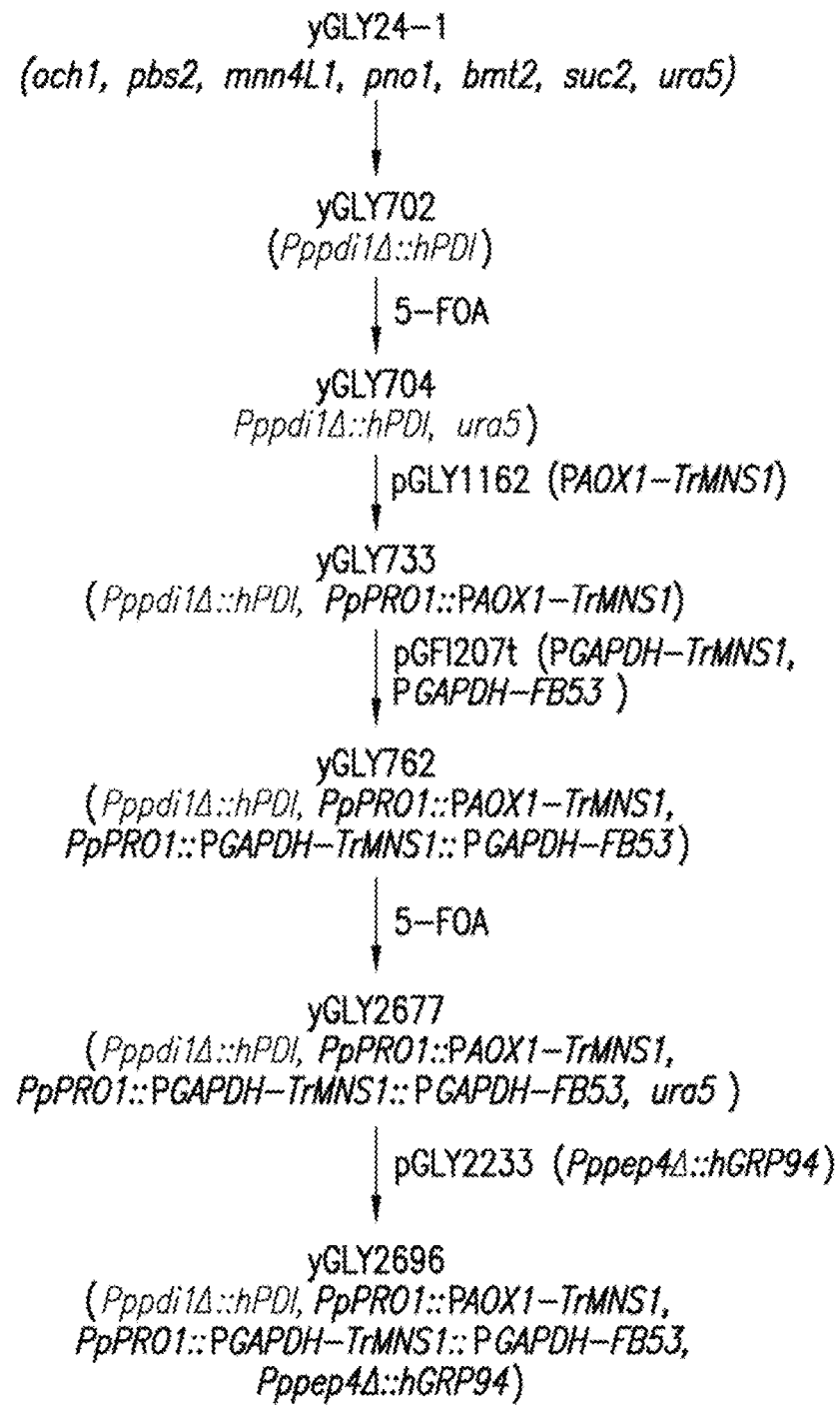
FIG. 6 illustrates the genealogy of some of the yeast strains used to demonstrate operation of the present invention.

Generation of Cell Lines was as follows and is shown in FIG. 6. The strain yGLY24-1 (ura5Δ::MET1 och1 Δ: lacZ bmt2Δ::lacZKlMNN2-2/mnn4L1 Δ::lacZ1 MmSLC35A3 pno1Δmnn4Δ::lacZ me16Δ::lacZ), was constructed using methods described earlier (See for example, Nett and Gerngross, Yeast 20:1279 (2003); Choi et al., Proc. Natl. Acad. Sci. USA 100:5022 (2003); Hamilton et al., Science 301: 1244 (2003)). The BMT2 gene has been disclosed in Mille et al., J. Biol. Chem. 283: 9724-9736 (2008) and U.S. Published Application No. 20060211085. The PNO1 gene has been disclosed in U.S. Pat. No. 7,198,921 and the mnn4L1 gene (also referred to as mnn4b) has been disclosed in U.S. Pat. No. 7,259,007. The mnn4 refers to mnn4L2 or mnn4a. In the genotype, K1MNN2-2 is the *Kluveromyces lactis* GlcNAc transporter and MmSLC35A3 is the *Mus musculus* GlcNAc transporter. The URA5 deletion renders the yGLY24-1 strain auxotrophic for uracil (See U.S. Published application No. 2004/0229306) and was used to construct the humanized chaperone strains that follow. While the various expression cassettes were integrated into particular loci of the *Pichia pastoris* genome in the examples herein, it is understood that the operation of the invention is independent of the loci used for integration. Loci other than those disclosed herein can be used for integration of the expression cassettes. Suitable integration sites include those enumerated in U.S. Published application No. 20070072262 and include homologs to loci known for *Saccharomyces cerevisiae* and other yeast or fungi.

Strains yGLY702 and yGLY704 were generated in order to test the effectiveness of the human PDI1 expressed in *Pichia pastoris* cells in the absence of the endogenous *Pichia pastoris* PDI gene. Strains yGLY702 and yGLY704 (huPDI) were constructed as follows. Strain yGLY702 was generated by transfecting yGLY24-1 with plasmid vector pGLY642 containing the expression cassette encoding the human PDI under control of the constitutive PpGAPDH promoter. Plasmid vector pGLY642 also contained an expression cassette encoding the *Pichia pastoris* URA5 which rendered strain yGLY702 prototrophic for uracil. The URA5 expression cassette was removed by counterselecting yGLY702 on 5-FOA plates to produce strain yGLY704 in which, so that the *Pichia pastoris* PDI1 gene has been stably replaced by the human PDI gene and the strain is auxotrophic for uracil.

Strain yGLY733 was generated by transfecting with plasmid vector pGLY1162, which comprises an expression cassette that encodes the *Trichoderma Reesei* mannosidase (TrMNS1) operably linked to the *Pichia pastoris* AOX1 promoter (PpAOX1-TrMNS1), into the PRO1 locus of yGLY704. This strain has the gene encoding the *Pichia pastoris* PD1 replaced with the expression cassette encoding the human PDI1, has the PpAOX1-TrMNS1 expression cassette integrated into the PRO1 locus, and is a URA5 auxotroph. The PpAOX1 promoter allows overexpression when the cells are grown in the presence of methanol.

Strain yGLY762 was constructed by integrating expression cassettes encoding TrMNS1 and mouse mannosidase IA (MuMNS1A), each operably linked to the *Pichia pastoris* GAPDH promoter in plasmid vector pGFI207t into control strain yGLY733 at the 5' PRO1 locus UTR in *Pichia pastoris* genome. This strain has the gene encoding the *Pichia pastoris* PD1 replaced with the expression cassette encoding the human PDI1, has the PpGAPDH-TrMNS1 and PpGAPDH-MuMNS1A expression cassettes integrated into the PROJ locus, and is a URA5 auxotroph.

Strain yGLY2677 was generated by counterselecting yGLY762 on 5-FOA plates. This strain has the gene encoding the *Pichia pastoris* PD1 replaced with the expression cassette encoding the human PDI1, has the PpAOX1-TrMNS1 expression cassette integrated into the PRO1 locus, has the PpGAPH-TrMNS1 and PpGAPDH-MuMNS1A expression cassettes integrated into the PROJ locus, and is a URA5 prototroph.

Strains yGLY2696 was generated by integrating plasmid vector pGLY2233, which encodes the human GRP94 protein, into the PEP4 locus. This strain has the gene encoding the *Pichia pastoris* PD1 replaced with the expression cassette encoding the human PDI1, has the PpAOX1-TrMNS1 expression cassette integrated into the PRO1 locus, has the PpGAPDH-TrMNS1 and PpGAPDH-MuMNS1A expression cassettes integrated into the PRO1 locus, has the human GRP64 integrated into the PEP4 locus, and is a URA5 prototroph. The genealogy of this chaperone-humanized strain is shown in FIG. 6.

Example 2

Expression vectors encoding an anti-Her2 antibody and an anti-CD20 antibody were constructed as follows.

Figure 7:
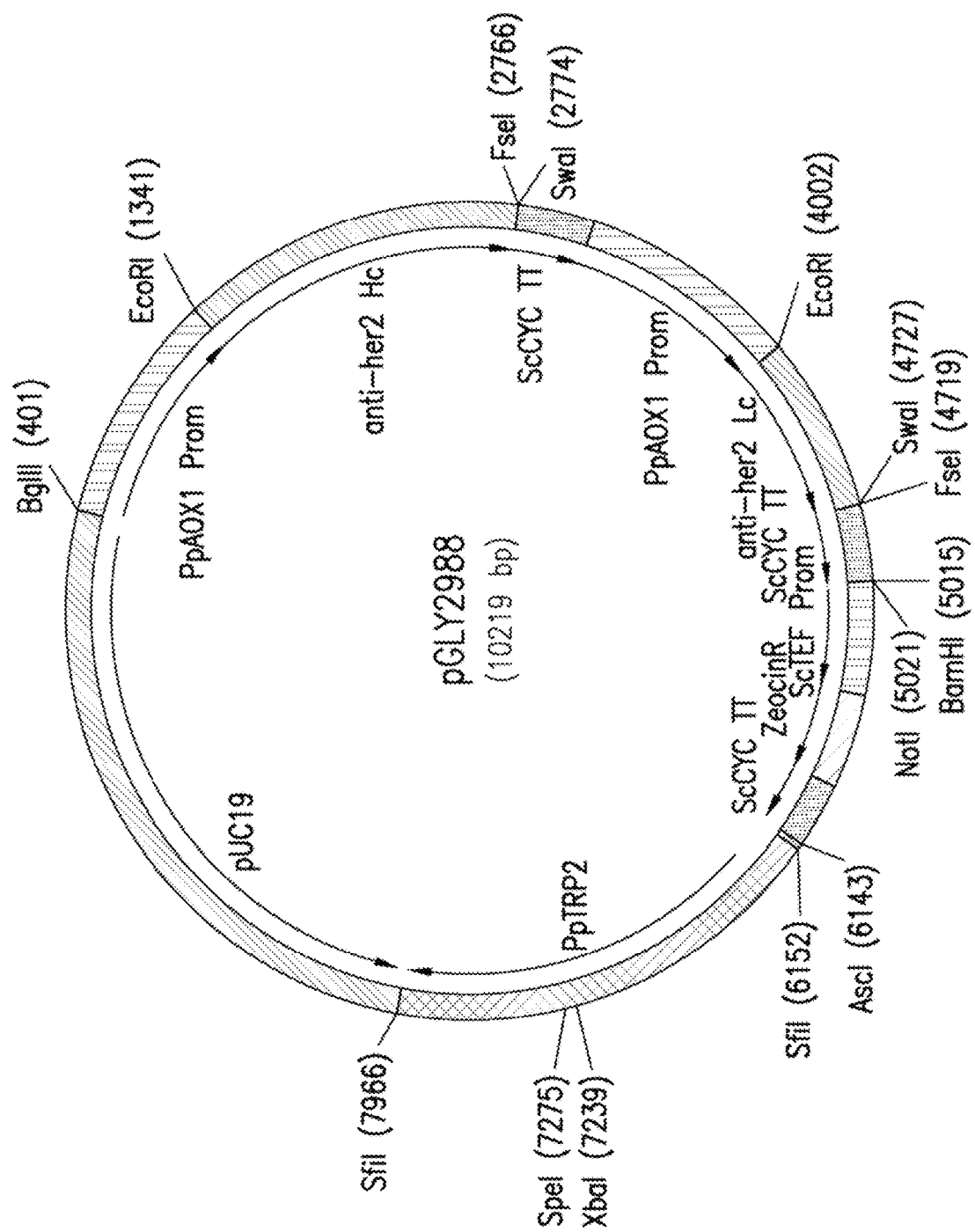
FIG. 7 shows a map of plasmid vector pGLY2988.

Expression/integration plasmid vector pGLY2988 contains expression cassettes encoding the heavy and light chains of an anti-Her2 antibody. Anti-Her2 heavy (HC) and light (LC) chains fused at the N-terminus to α-MAT pre signal peptide were synthesized by GeneArt AG. The nucleotide and amino acid sequences for the α-amylase signal peptide are shown in SEQ ID NOs:27 and 28. Each was synthesized with unique 5' EcoR1 and 3' Fse1 sites. The nucleotide and amino acid sequences of the anti-Her2 HC are shown in SEQ ID Nos:29 and 30, respectively. The nucleotide and amino acid sequences of the anti-Her2 LC are shown in SEQ ID Nos:31 and 32, respectively. Both nucleic acid molecule fragments encoding the HC and LC fusion proteins were separately subcloned using 5' EcoR1 and 3' Fse1 unique sites into an expression plasmid vector pGLY2198 (contains the *Pichia pastoris* TRP2 targeting nucleic acid molecule and the Zeocin®-resistance marker) to form plasmid vector pGLY2987 and pGLY2338, respectively. The LC expression cassette encoding the LC fusion protein under the control of the *Pichia pastoris* AOX1 promoter and *Saccharomyces cerevisiae* CYC terminator was removed from plasmid vector pGLY2338 by digesting with BamHI and NoII and then cloning the DNA fragment into plasmid vector pGLY2987 digested with BamH1 and Not1, thus generating the final expression plasmid vector pGLY2988 (FIG. 7).

Expression/integration plasmid vector pGLY3200 (map is identical to pGLY2988 except LC and HC are anti-CD20 with α-amylase signal sequences). Anti-CD20 sequences were from GenMab sequence 2C6 except Light chain (LC) framework sequences matched those from VKappa 3 germline. Heavy (HC) and LC variable sequences fused at the N-terminus to the α-amylase (from *Aspergillus niger*) signal peptide were synthesized by GeneArt AG. The nucleotide and amino acid sequences for the α-amylase signal peptide are shown in SEQ ID NOs:33 and 34. Each was synthesized with unique 5' EcoR1 and 3' KpnI sites which allowed for the direct cloning of variable regions into expression vectors containing the IgG1 and V kappa constant regions. The nucleotide and amino acid sequences of the anti-CD20 HC are shown in SEQ ID Nos:37 and 38, respectively. The nucleotide and amino acid sequences of the anti-CD20 LC are shown in SEQ ID Nos:35 and 36, respectively. Both HC and LC fusion proteins were subcloned into IgG1 plasmid vector pGLY3184 and VKappa plasmid vector pGLY2600, respectively, (each plasmid vector contains the *Pichia pastoris* TRP2 targeting nucleic acid molecule and Zeocin-resistance marker) to form plasmid vectors pGLY3192 and pGLY3196, respectively. The LC expression cassette encoding the LC fusion protein under the control of the *Pichia pastoris* AOX1 promoter and *Saccharomyces cerevisiae* CYC terminator was removed from plasmid vector pGLY3196 by digesting with BamHI and NotI and then cloning the DNA fragment into plasmid vector pGLY3192 digested with BamH1 and Not1, thus generating the final expression plasmid vector pGLY3200 (FIG. 8).

Transfection of strain yGLY2696 with the above anti-Her2 or anti-CD20 antibody expression/integration plasmid vectors was performed essentially as follows. Appropriate *Pichia pastoris* strains were grown in 50 mL YPD media (yeast extract (1%), peptone (2%), dextrose (2%)) overnight to an OD of between about 0.2 to 6. After incubation on ice for 30 minutes, cells were pelleted by centrifugation at 2500-3000 rpm for 5 minutes. Media were removed and the cells washed three times with ice cold sterile 1M sorbitol before resuspending in 0.5 mL ice cold sterile 1 M sorbitol. Ten L linearized DNA (5-20 µg) and 100 µL cell suspension was combined in an electroporation cuvette and incubated for 5 minutes on ice. Electroporation was in a Bio-Rad GenePulser Xcell™ following the preset *Pichia pastoris* protocol (2 kV, 25 F, 200 Q), immediately followed by the addition of 1 mL YPDS recovery media (YPD media plus 1 M sorbitol). The transfected cells were allowed to recover for four hours to overnight at room temperature (26° C.) before plating the cells on selective media. Strain yGLY2696 transfected with pGLY2988 encoding the anti-HER2 antibody was designated yGLY4134. Strain yGLY2696 transfected with pGLY3200 encoding the anti-CD20 antibody was designated yGLY3920.

Example 3

This example describes the construction of plasmids comprising expression cassettes encoding cell surface anchoring proteins fused to binding moieties capable of binding an immunoglobulin, which are suitable for use in *Pichia pastoris*. The plasmids comprise a nucleic acid molecule encoding sed1p, a cell surface anchoring protein that inherently contains an attached glycophosphotidylinositol (GPI) post-translational modification that anchors the protein in the cell wall. The nucleic acid molecule encoding the sed1p was linked in frame to a nucleic acid molecule encoding an antibody-binding moiety that is capable of binding whole, intact antibodies.

Figure 9:
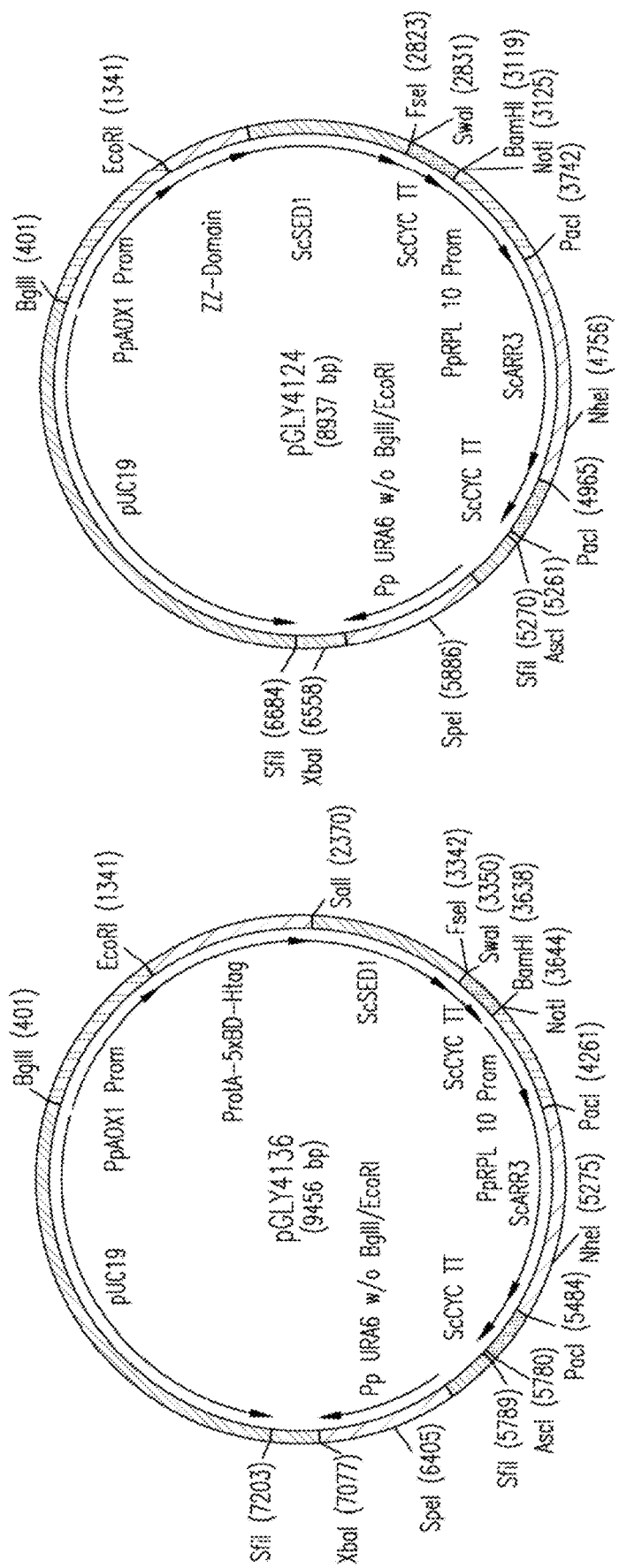
FIG. 9 shows maps of plasmid vectors pGLY4136 and pGLY4124.
Figure 10:
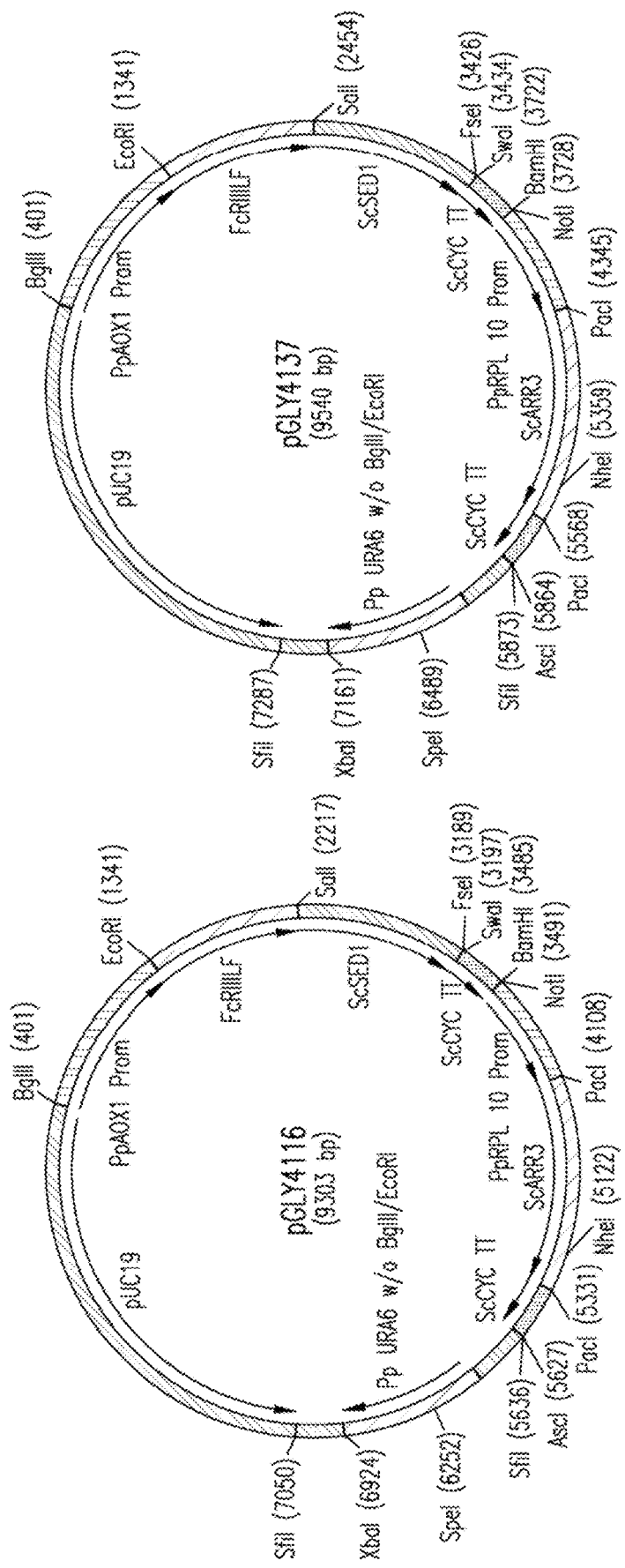
FIG. 10 shows maps of plasmid vectors pGLY4116 and pGLY4137.

Four plasmids were constructed containing antibody binding moiety/cell surface anchor fusion protein expression cassettes. Plasmid pGLY4136 encodes the five Fc binding domains of Protein A fused to the *Saccharomyces cerevisiae* SED1 (ScSED1) gene followed by the CYC terminator, all under the control of the AOX promoter (FIG. 9). Plasmid pGLY4116 encodes the Fc receptor III (FcRIII (LF)) fused to the ScSED1 gene (FIG. 10). Plasmid pGLY4137 encodes Fc receptor 1 (FcR1) fused to the ScSEDI gene (FIG. 10) and plasmid pGLY4124 (FIG. 9) encodes the ZZ-domain from Protein A fused to the ScSED1 gene. The ZZ-domain consists of two of the five Fc binding domains. All four plasmids contain a pUC19 *E. coli* origin and an arsenite resistance marker and are integrated into the *Pichia pastoris* genome at the URA6 locus.

Figure 20:
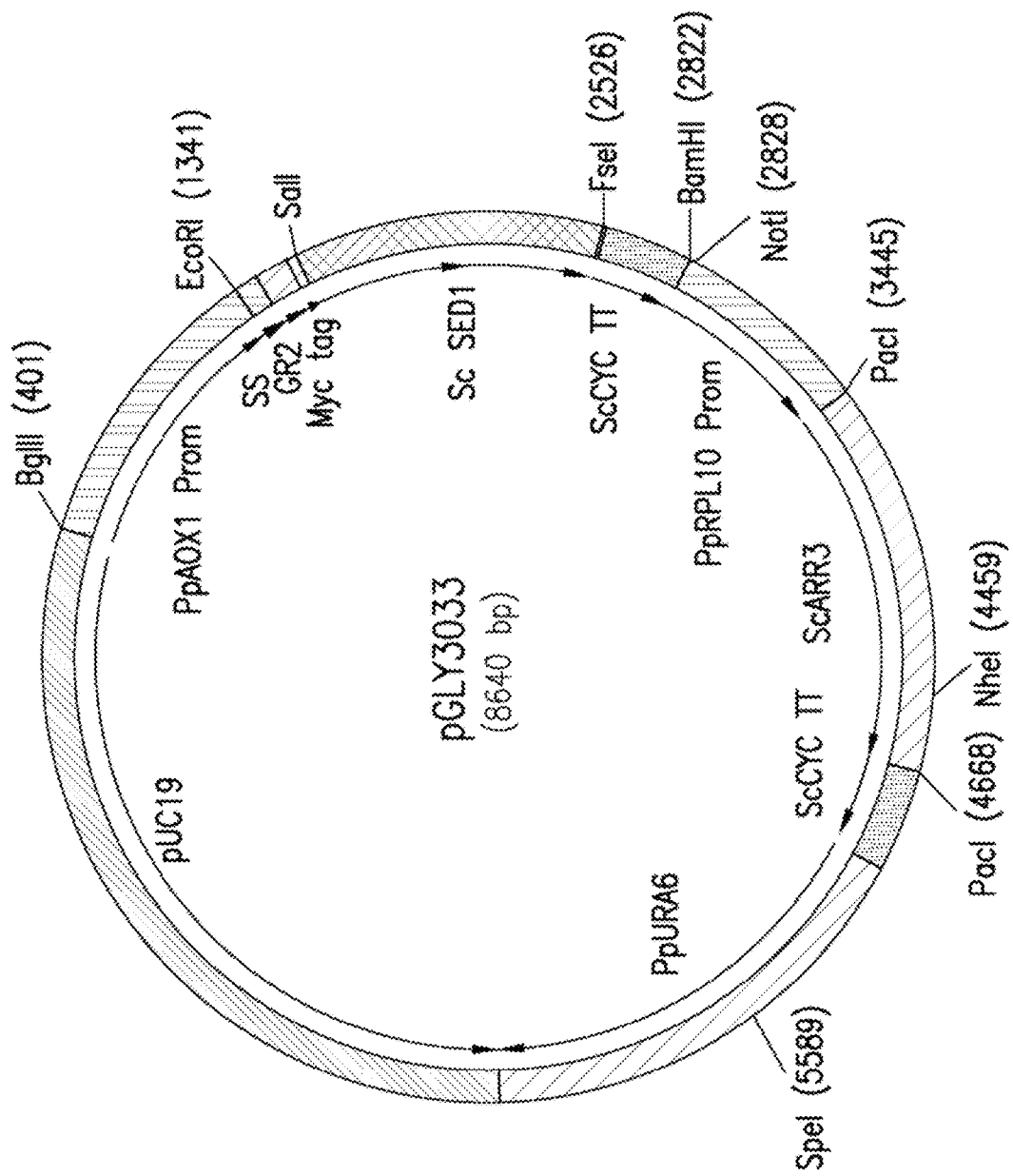
FIG. 20 shows a map of plasmid vector pGLY3033.

Plasmid pGLY3033 comprising an expression cassette encoding a fusion protein comprising the *Saccharomyces cerevisiae* SED1 GPI anchoring protein without its endogenous signal peptide (SED1 fragment) has been described in copending Application Ser. No. 61/067,965 filed Mar. 3, 2008. The SED1 amino acid sequence without its endogenous signal peptide is shown in SEQ ID NO:60. A nucleic acid molecule encoding the SED1 fragment was synthesized by GeneArt AG. The codons encoding the fragment had been optimized for expression in *Pichia pastoris*. The nucleotide sequence encoding the SED1 fragment is shown in SEQ ID NO:61). The *Pichia pastoris* URA6 locus was chosen as an integrating site for the GPI anchoring protein expression cassette. The URA6 gene was PCR amplified from *Pichia pastoris* genomic DNA and cloned into pCR2.1 TOPO™ (Invitrogen, La Jolla, CA) to produce plasmid pGLY1849. The BglII and EcoRI sites within the gene were mutated by silent mutation for cloning purposes. The TRP2 targeting nucleic acid molecule of plasmid pGLY2184 was replaced with the *Pichia pastoris* URA6 gene from pGLY1849. In addition, the *Pichia pastoris* ARG1 selection marker was replaced with the Arsenite marker cassette from plasmid pGFI8. The final plasmid was named pGFI30t and was used to make plasmid pGLY3033 (FIG. 20), containing an expression cassette comprising a nucleic acid molecule encoding the SED1 fragment protein fused at its amino terminus to a GR2 coiled-coil peptide and *Aspergillus niger* alpha-amylase signal peptide operably linked to the PpAOX1 promoter. The GR2 coiled coil and signal peptide encoding fragment can be removed by EcoRI and SalI digestion and replaced with an antibody capture moiety to make a fusion protein in which the capture moiety is fused to a cell surface anchoring protein.

Plasmid pGLY4136 comprising an expression cassette encoding the five Fc binding domains of protein A fused to the SED1 fragment under the control of the AOX1 promoter was constructed as follows. A nucleic acid molecule fragment encoding the five Fc binding domains from protein A was synthesized by GeneArt AG to encode the five Fc binding domains fused to the *Saccharomyces cerevisiae* α-Mating Factor pre signal sequence at the N-terminus and an HA and 9× HIS Tag sequence at the C-terminus and to have an EcoRI 5' end and a SalI 3' end. The fragment apre-5xBD-Htag has the nucleotide sequence shown in SEQ ID NO:45. The apre-5xBD-Htag fusion protein has the amino acid sequence shown in SEQ ID NO:46. The nucleic acid molecule encoding the apre-5xBD-Htag fusion protein was digested with EcoRI and SalI and the fragment cloned into pGLY3033, which had been digested with EcoRI and SalI to remove the GR2 coiled coil encoding fragment. This produced plasmid pGLY4136, which contains operably linked to the PpAOX1 promoter, the nucleic acid molecule encoding the apre-5xBD-Htag fusion protein linked in-frame to the nucleic acid molecule encoding the SED1 fragment. The plasmid is an integration/expression vector that targets the plasmid to the URA6 locus. The fusion protein expressed by this integration/insertion plasmid is referred to herein as the Protein A/SED1 fusion protein.

To put the Protein A/SED1 fusion protein under the control of the GAPDH promoter, plasmid pGLY4136 was digested with BglII and EcoRI to release the AOX1 promoter and to insert the *Pichia pastoris* GAPDH promoter from pGLY880. This produced plasmid pGLY4139.

Plasmid pGLY4124 comprising an expression cassette encoding the Protein A ZZ domain fused to the SED1 fragment under the control of the AOX1 promoter was constructed as follows. The ZZ-domain from GeneArt© plasmid 0706208 ZZHAtag was PCR amplified using the following primers: primer alpha-amy-ProtAZZ/up:

```
primer alpha-amy-ProtAZZ/up:
                                    (SEQ ID NO: 47)
CGGAATTCacgATGGTCGCTTGGTGGTCTTTGTTTCTGTACGGTCTTCA
GGTCGCTGCACCTGCTTTTGGCTTCTGGTGGTGTTACTCCAGCTGCTAAC
GCTGCTCAACACG
and HA-ProtAZZ-XhoIZZ/lp:
                                    (SEQ ID NO: 48)
GCCTCGAGAGCGTAGTCTGGAACATCGTATGGGTAACCACCACCAGCAT
C.
```

T1 a 1 a2a r ZZ/up primer includes in-frame the coding sequence for the first amino acids of the *Aspergillus niger* α-amylase signal peptide (underlined). The primers introduce an EcoRI site at the 5' end of the coding region and a XhoI site at the 3' end. The nucleic acid sequence of the ZZ-domain as an EcoRI/XhoI fragment is shown in SEQ ID NO:49. The amino acid sequence of the ZZ-domain is shown in SEQ ID NO:50. The PCR conditions were one cycle of 95° C. for 2 minutes, 20 cycles of 98° C. for 10 seconds, 65° C. for 10 seconds, and 72° C. for 1 minute, and followed by one cycle of 72° C. for 10 minutes.

The PCR fragment was cloned into plasmid pCR2.1 TOPO and the cloned fragment sequenced to confirm the sequence encoded the Protein A ZZ domain. The ZZ-domain fragment was extracted from the pCR2.1 TOPO™ vector by EcoRI and XhoI digest and the EcoRI/XhoI fragment was cloned into plasmid pGLY3033, which had been digested with EcoRI and Sα/l to remove the GR2 coiled coil encoding fragment. This produced plasmid pGLY4124, which contains operably linked to the PpAOX1 promoter, the nucleic acid molecule encoding the Protein A ZZ domain-alpha amylase signal peptide fusion protein linked in-frame to the nucleic acid molecule encoding the SED1 fragment. The plasmid is an integration/expression vector that targets the plasmid to the URA6 locus. The fusion protein expressed by this integration/insertion plasmid is referred to herein as the ZZ/SED1 fusion protein.

Plasmid pGLY4116 comprising an expression cassette encoding the FcRIIIa LF receptor fused to the SED1 fragment under the control of the AOX1 promoter was constructed as follows. A nucleic acid molecule encoding the FcRIIIa LF receptor was PCR amplified from plasmid pGLY3247 (FcRIIIa LF) as an EcoRI/SalI fragment. In plasmid pGLY3247, the FcRIIIa LF receptor is a fusion protein in which the endogenous signal peptide had been replaced with the α-MFpre-pro. The 5' primer anneals to the sequence encoding the signal peptide and the 3' primer anneals to the His-tag at the end of the receptor and omits the stop codon for the receptor. The 5' primer was 5Ecoapp:

```
The 5' primer was 5Ecoapp:
                                    (SEQ ID NO: 51)
AACGGAATTCATGAGATTTCCTTCAATTTTTAC
and the 3' primer was 3HtagSal
                                    (SEQ ID NO: 52)
CGATGTCGACGTGATGGTGATGGTGGTGATGATGATGACCACC.
```

The PCR conditions were one cycle of 95° C. for 2 minutes, 25 cycles of 95° C. for 30 seconds, 58° C. for 30 seconds, and 72° C. for 70 seconds, and followed by one cycle of 72° C. for 10 minutes.

The PCR fragment encoding the receptor fusion protein was cloned into plasmid pCR2.1 TOPO™ and the cloned fragment sequenced to confirm the sequence encoded the receptor. The nucleotide sequence of the FcRIII(LF) as an EcoRI/SalI fragment is shown in SEQ ID NO:53. The amino acid sequence of the FcRIII(LF) with a MF pre-signal sequence is shown in SEQ ID NO:54.

Plasmid pCR2.1 TOPO™ was digested with EcoRI and SalI and the EcoRI/SalI fragment encoding the receptor was cloned into pGLY3033, which had been digested with EcoRI and SalI to remove the GR21 coiled coil encoding fragment. This produced plasmid pGLY4116, which contains operably linked to the PpAOX1 promoter, the nucleic acid molecule encoding the FcRIIIa LF/α-MF pre-pro signal peptide fusion protein linked in-frame to the nucleic acid molecule encoding the SED1 fragment. The plasmid is an integration/expression vector that targets the plasmid to the URA6 locus. The fusion protein expressed by this integration/insertion plasmid is referred to herein as the FcRIIIa fusion protein.

Plasmid pGLY4137 encoding the FcRI receptor fused to the SED1 fragment was constructed as follows. A nucleic acid molecule encoding the FcRI receptor was PCR amplified from plasmid pGLY3248 as an EcoRI/SalI fragment. In plasmid pGLY3248, the FcRI receptor is a fusion protein in which the endogenous signal peptide had been replaced with the α-MFpre-pro. The 5' primer anneals to the sequence encoding the signal peptide and the 3' primer anneals to the His-tag at the end of the receptor and omits the stop codon for the receptor. The 5' primer was 5Ecoapp:

```
                                    (SEQ ID NO: 51)
AACGGAATTCATGAGATTTCCTTCAATTTTTAC
and the 3' primer was 3HtagSal (SEQ ID NO: 52)
CGATGTCGACGTGATGGTGATGGTGGTGATGATGATGACCACC.
```

The PCR conditions were one cycle of 95° C. for 2 minutes, 25 cycles of 95° C. for 30 seconds, 58° C. for 30 seconds, and 72° C. for 70 seconds, and followed by one cycle of 72° C. for 10 minutes.

The PCR fragment encoding the receptor fusion protein was cloned into plasmid pCR2.1 TOPO™ and the cloned fragment sequenced to confirm the sequence encoded the receptor. The nucleic acid sequence of the FcRI as an EcoRI/SalI fragment is shown in SEQ ID NO:55. The amino acid sequence of the FcRI with a MF pre-signal sequence is shown in SEQ ID NO:56.

Plasmid pCR2.1 TOPO™ was digested with EcoRI and SalI and the EcoRI/SalI fragment encoding the receptor was cloned into pGLY3033, which had been digested with EcoRI and SalI to remove the GR21 coiled coil encoding fragment. This produced plasmid pGLY4116, which contains operably linked to the PpAOX1 promoter, the nucleic acid molecule encoding the FcRI/α-MF pre-pro signal peptide fusion protein linked in-frame to the nucleic acid molecule encoding the SED1 fragment. The plasmid is an integration/expression vector that targets the plasmid to the URA6 locus. The fusion protein expressed by this integration/insertion plasmid is referred to herein as the FcRI fusion protein.

Example 4

Co-Expression of antibody and antibody binding moiety/cell surface anchor fusion protein in *Pichia pastoris* was as follows.

*Pichia pastoris* strains yGLY4134 (expresses anti-HER2 antibody) and yGLY3920 (expresses anti-CD20 antibody) were each transfected with pGLY4116 (expresses FcRIII receptor/SED fusion protein), pGLY4136 (expresses Protein A/SED fusion protein), pGLY4124 (expresses Protein A ZZ domain/SED fusion protein), or pGLY4137 (expresses FcRI receptor/SED fusion protein). YGLY2696 was also transfected with each of the above four expression/integration vectors. For transfection, the strains are grown in 50 mL BMGY media until the culture reached a density of about OD600=2.0. The cells are washed three times with 1 M sorbitol and resuspended in 1 mL 1 M sorbitol. About 1 to 2 μg of linearized plasmid are mixed with the cells. Transfection is performed with a BioRad electroporation apparatus using the manufacturer's program specific for electroporation of nucleic acid molecules into *Pichia pastoris*. One mL of recovery media is added to the cells, which are then plated out on YPG (yeast extract:peptone:glycerol medium) with 50 pg/mL arsenite.

Cell surface labeling was as follows. Strain yGLY4134 (expresses anti-Her2 antibody), strain yGLY4134 transfected with pGLY4136 (expresses anti-Her2 antibody and Protein A/SED1 fusion protein, and strain YGLY2696 transfected with pGLY4136 (expresses Protein A/SED1 fusion protein) were grown in 600 μL BMGY (buffered minimal glycerol medium-yeast extract, Invitrogen) in a 96 deep well plate or 50 mL BMGY in a 250 mL shake flask for two days. The cells were collected by centrifugation and the supernatant was discarded. The cells were induced by incubation in 300 μL or 25 mL BMMY with Pmti-3 inhibitor overnight following the methods taught in WO2007/061631. Pmti-3 is 3-hydroxy-4-(2-phenylethoxy)benzaldehyde; 3-(1-phenylethoxy)-4-(2-phenylethoxy)-benzaldehyde, which as been described in U.S. Pat. No. 7,105,554 and Published International Application No. WO 2007061631. The Pmti-3 inhibitor reduces the O-glycosylation occupancy, that is the number of total O-glycans on the antibody molecule. The cell further express a *T. reesei* alpha-1,2-mannsodase catalytic domain linked to the *Saccharomyces cerevisiea* MAT pre signal peptide to control the chain length of those O-glycans that are on the antibody molecule.

Figure 11:
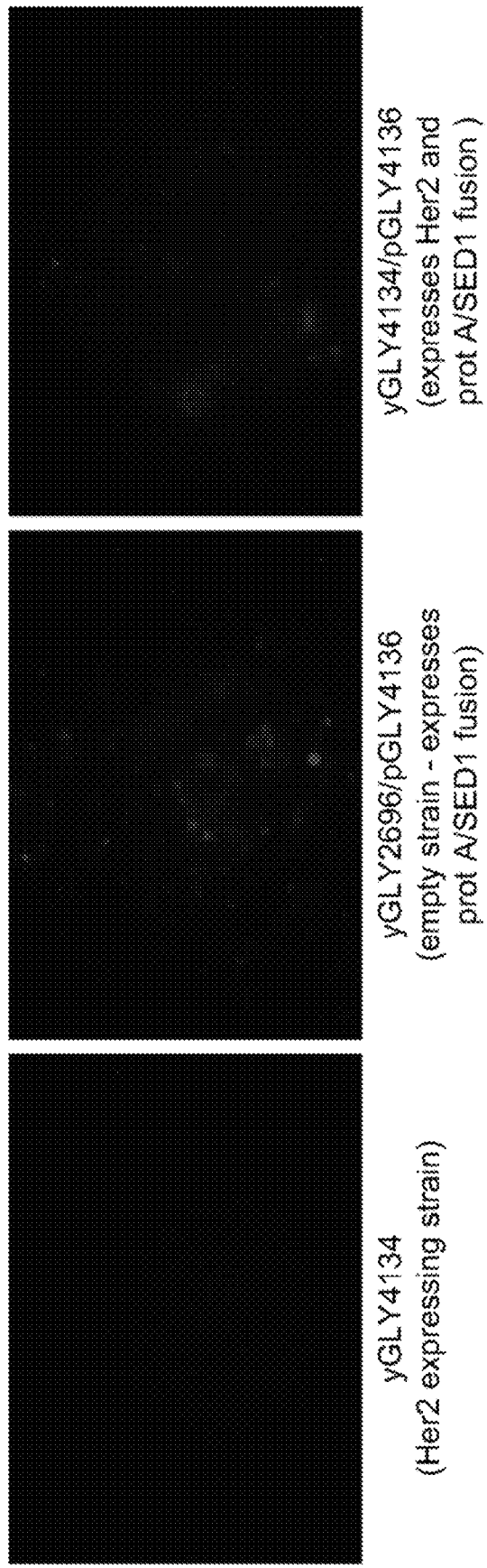
FIG. 11 shows fluorescence microscopy results of strain yGLY4134 (expresses anti-Her2 antibody), strain yGLY2696 (empty strain) transfected with pGLY4136 encoding Protein A/SED1 fusion protein, and strain yGLY4134 (expresses anti-Her2 antibody) transfected with pGLY4136 encoding Protein A/SED1 fusion protein incubated with goat anti-human IgG (H+L)-Alexa Fluor® 488.
Figure 12:
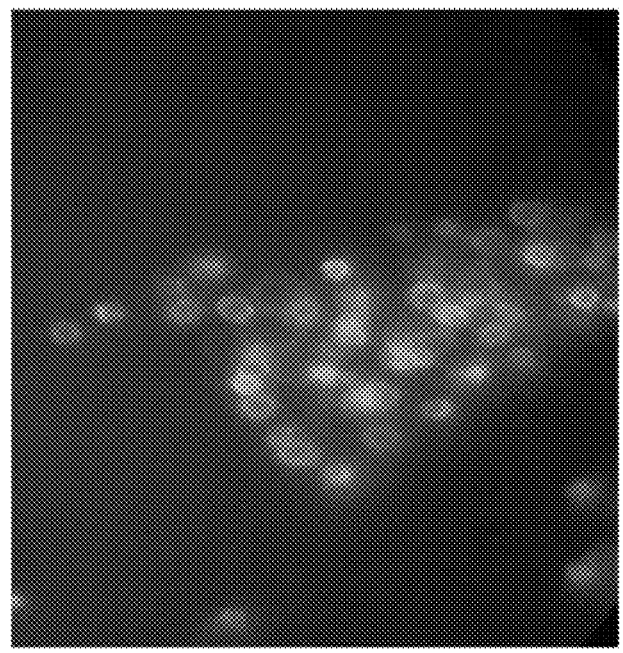
FIG. 12 shows fluorescence microscopy results of strain yGLY2696 (empty strain) transfected with pGLY4136 encoding the Protein A/SED1 fusion protein incubated with anti-Her2 antibody. Goat anti-human IgG (H+L)-Alexa Fluor® 488 was used for detection of anti-antibody bound to the Protein A/SED1 fusion protein anchored to the cell surface.

Induced cells were labeled with goat anti-human heavy and light chain (H+L) Alexa Fluor® 488 (Invitrogen, Carlsbad, CA) conjugated antibody and viewed using fluorescence microscopy as follows. After induction, cells at density of about 0.5-1.0 OD600 were collected by centrifugation in a 1.5-mL tube. The cells were rinsed twice with 1 mL PBS and 0.5 mL goat anti-human IgG (H+L)-Alexa Fluor®-488 (1:500 in 1% BSA in PBS) was added. The tubes were rotated for one hour at 37° C., centrifuged, and rinsed 3x with 1 mL PBS to remove the detection antibody. The cells were resuspended in about 50-100 μL of PBS and a 10 μL aliquot viewed with a fluorescence microscope and photographed (FIG. 12). As expected, both the anti-Her2 antibody expressing strain yGLY4134 without pGLY4136 encoding the protein A/SED1 fusion protein and yGLY2696 with pGLY4136 encoding the Protein A/SED1 fusion protein but no anti-Her2 antibody showed no surface labeling. The weak labeling that was visible on the cells of yGLY2696 transfected with pGLY4136 might be due to cross reaction of the goat anti human heavy and light chain (H+L) Alexa Fluor®488 conjugated antibody to the expressed Protein A. However, as can also be seen in FIG. 11, co-expression of the Protein A/SED1 fusion protein and the anti-Her2 antibody (strain yGLY4134 transfected with pGLY4136) did not result in displayed antibody on the cell surface and showed only background labeling. This result suggested that simultaneously expressing the antibody and Protein A/SED1 protein interfered with display of the antibody on the cell surface or the Protein A/SED1 protein was not properly anchored to the cell surface.

Example 5

This example demonstrates that the Protein A/SED1 fusion protein is properly anchored to the cell surface and that co-expressing the anti-Her2 antibody and Protein A/SED1 fusion protein at the same time interfere with capture and display of the antibody on the cell surface.

To test whether the Protein A/SED1 fusion protein itself is displayed on the cell surface, strain yGLY2696 transfected pGLY4136 encoding the Protein A/SED1 fusion protein was grown and induced as described in the previous example. At a cell density of about 0.5-1.0 OD600, cells were collected by centrifugation in a 1.5-mL tube and rinsed twice with 1 mL PBS. Either 10 or 50 ng of anti-Her2 antibody was added externally to the cells and the cells incubated for one hour. Afterwards, the cells were washed 3× in 1 ml PBS and labeled with goat anti human H+L as described in the previous example. The results showed that the anti-Her2 antibody was captured and displayed on the surface of the cells. This can be seen in FIG. 12, which shows strong cell surface staining. The results confirm that the Protein A/SED1 fusion protein is expressed, the expressed fusion protein is properly inserted into the cell surface, and the fusion protein is able to capture and display antibodies on the cell surface.

Figure 13:
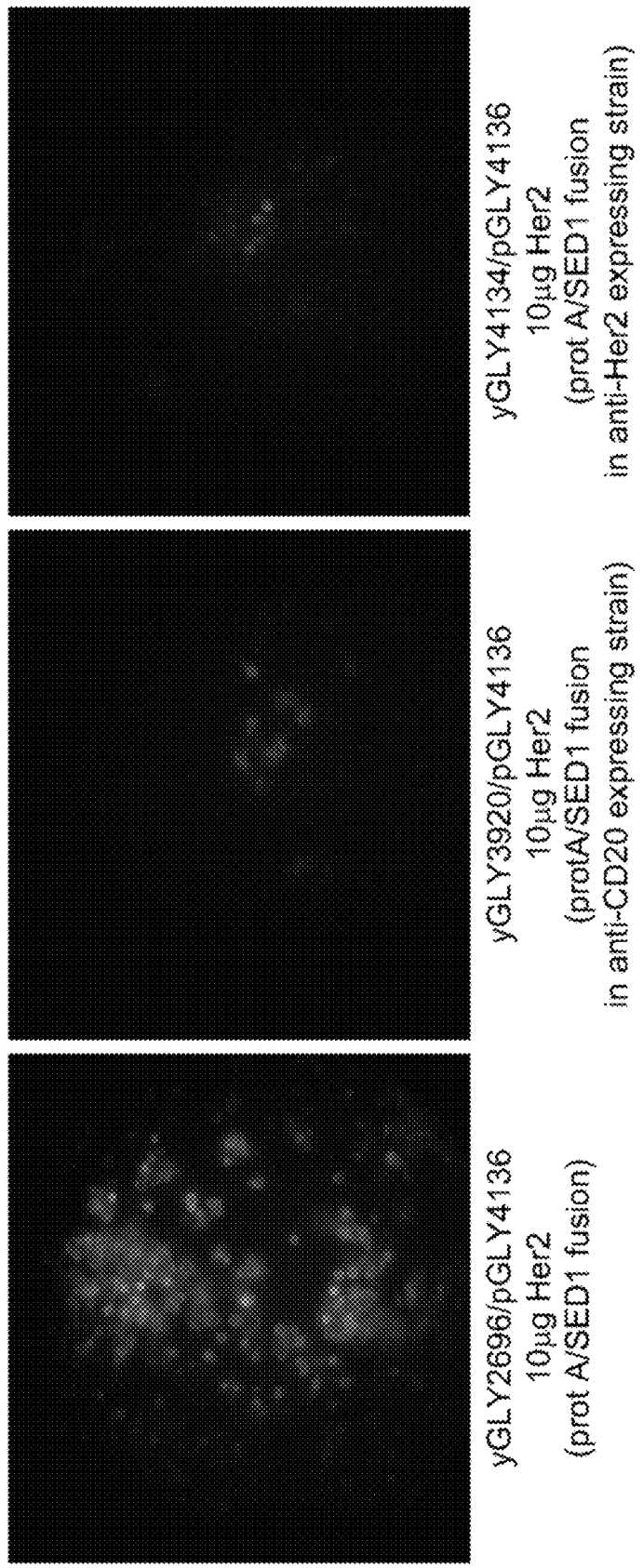
FIG. 13 shows fluorescence microscopy results of strain yGLY2696 (empty strain) transfected with pGLY4136 encoding Protein A/SED1 fusion protein, strain yGLY3920 (expresses anti-CD20 antibody) transfected with pGLY4136 encoding Protein A/SED1 fusion protein, and strain yGLY4134 (expresses anti-Her2 antibody) transfected with pGLY4136 encoding Protein A/SED1 fusion protein incubated with anti-Her2 antibody. Goat anti-human IgG (H+L)-Alexa Fluor® 488 was used for detection of anti-antibody bound to the Protein A/SED1 fusion protein anchored to the cell surface.

To determine whether co-expression interfered with display of the antibody on the cell surface, strain yGLY2696 transfected with pGLY4136 (empty strain that expresses Protein A/SED1 fusion protein), strain yGLY4134 transfected with pGLY4136 (strain expresses anti-Her2 antibody and Protein A/SED1 fusion protein), and strain yGLY3920 transfected with pGLY4136 (strain expresses anti-CD20 antibody and Protein A/SED1 fusion protein) were grown and induced as in the previous example. Cells were incubated with 10 ng externally added anti-Her2 antibody, labeled, and detected as in the previous example. FIG. 13 illustrates strong cell surface labeling of the empty strain expressing only the Protein A/SED1 fusion protein (yGLY2696 transfected with pGLY4136), but only weak staining in the strains when the Protein A/SED1 fusion protein and the antibody were co-expressed (yGLY4134 transfected with pGLY4136 and yGLY3920 transfected with pGLY4136). Cells expressing the Protein A/SED1 fusion protein were able to capture externally added antibody and display it while cells co-expressing antibody and Protein A/SED1 fusion protein were unable to capture externally added antibody nor display their own secreted antibody.

These results suggested that the Protein A/SED1 fusion protein is not displayed well on the cell surface in an antibody co-expressing strain. This may be because co-expression of the Protein A/SED1 fusion protein and the antibody from the strong AOX promoter under methanol induction may lead to aggregation of the antibody—Protein A/SED1 fusion protein complex in the ER and degradation. Alternatively, the antibody—Protein A/SED1 fusion protein complex produced in the ER may not secrete well because of its molecular weight or steric hindrance.

Example 6

Other antibody binding moieties were tested for their ability to display antibody on the cell surface of *P. pastoris*. These include the Fc receptor 1 (FcRI), the Fc receptor 111 (FcRIII) and the Protein A ZZ-domain. Strains yGLY2696 (empty), yGLY4134 (expresses anti-Her2 antibody) and yGLY3920 (expresses anti-CD20 antibody) were separately transfected with each of plasmids pGLY4116 (encodes FcRIII/SED1 fusion protein), pGLY4124 (encodes Protein A ZZ domain/SED1 fusion protein), and pGLY4136 (encodes Protein A/SED1 fusion protein), were grown, induced and labeled as in Example 4.

The results for the ZZ-domain were similar to those for Protein A albeit the staining was somewhat weaker. This suggests that two Fc binding domains have a lower affinity for the antibody compared to the intact Protein A, which has five Fc binding domains.

Figure 14:
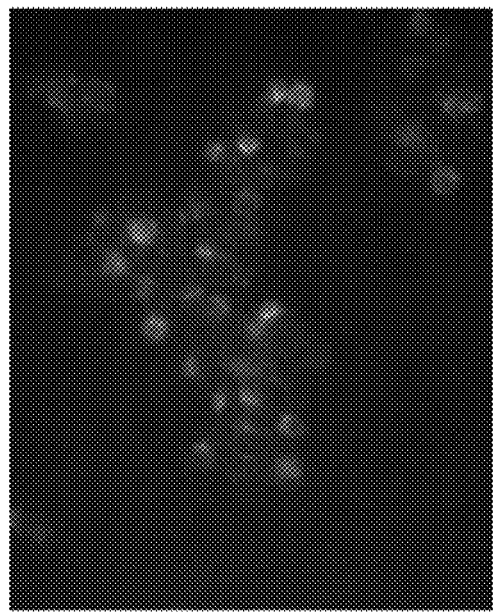
FIG. 14 shows fluorescence microscopy results of strain yGLY2696 (empty strain) transfected with pGLY4116 encoding the FcRIII/SED1 fusion protein incubated with anti-Her2 antibody. Goat anti-human IgG (H+L)-Alexa Fluor® 488 was used for detection of anti-antibody bound to the Protein A/SED1 fusion protein anchored to the cell surface.

Co-expression of the FcRIII/SED1 fusion protein and antibody resulted in a lack of cell surface staining. Strain yGLY2696 transfected with pGLY4116 (encodes FcRIII/SED1 fusion protein) was grown and induced as described in Example 4 and the cells were incubated with 10 or 50 ng externally added anti-Her2 antibody. Contrary to the results from strains that expressed the Protein A/SED1 fusion protein, cell surface staining was absent while some intracellular staining is observed (FIG. 14). The results suggest that while the FcRIII/SED1 fusion protein may be expressed in the cell, it did not appear to be secreted.

Example 7

This example demonstrates that temporal expression of the Protein A/SED1 fusion protein and the antibody enables proper expression and capture of the secreted antibody on the cell surface.

The above experiments suggested that co-expression of the antibody binding moiety/cell surface anchor fusion protein and the antibody together does not allow the anchor to be displayed at the cell surface. In the above experiments, both the antibody binding moiety/cell surface anchor fusion protein and antibody were expressed from nucleic acid molecules operably linked to the strong AOX inducible promoter. It was hypothesized that inducing expression of the antibody binding moiety/cell surface anchor fusion protein first, then after sufficient antibody binding moiety/cell surface anchor fusion protein had been made and anchored to the cell surface, inhibiting expression of the antibody binding moiety/cell surface anchor fusion protein and inducing expression of the antibody, would enable the antibody that is made to be captured at the cell surface by the antibody binding moiety/cell surface anchor fusion protein. Therefore, different promoters that would allow temporal expression of the nucleic acid molecules encoding the antibody binding moiety/cell surface anchor fusion protein and antibody were tested.

The GUT1 promoter is a promoter that is induced in cells grown in the presence of glycerol and repressed when the cells are switched to a medium that lacks glycerol but contains dextrose. PCR was used to amplify the GUT1 promoter from genomic DNA of *Pichia pastoris* as BglII/EcoRI fragment using primer 5gutBglII ATTGAGATCT ACCCAATTTA GCAGCCTGCA TTCTC (SEQ ID NO:57) and primer 3gutEcoRI GTCAGAATTC ATCTGTGGTA TAGTGTGAAA AAGTAG (SEQ ID NO:58). The PCR fragment was then cloned into the pCR2.1 TOPO vector, and then sequenced to confirm the sequence. The GUT1 promoter fragment was extracted from the pCR2.1 TOPO™ vector by BglII/EcoRI digest and cloned into pGLY4136 digested with BglII/EcoRI to exchange the AOX1 promoter by the GUT1 promoter. The nucleotide sequence of the GUT1 promoter including the BglI and EcoRI ends is shown in SEQ ID NO:59.

Figure 15:
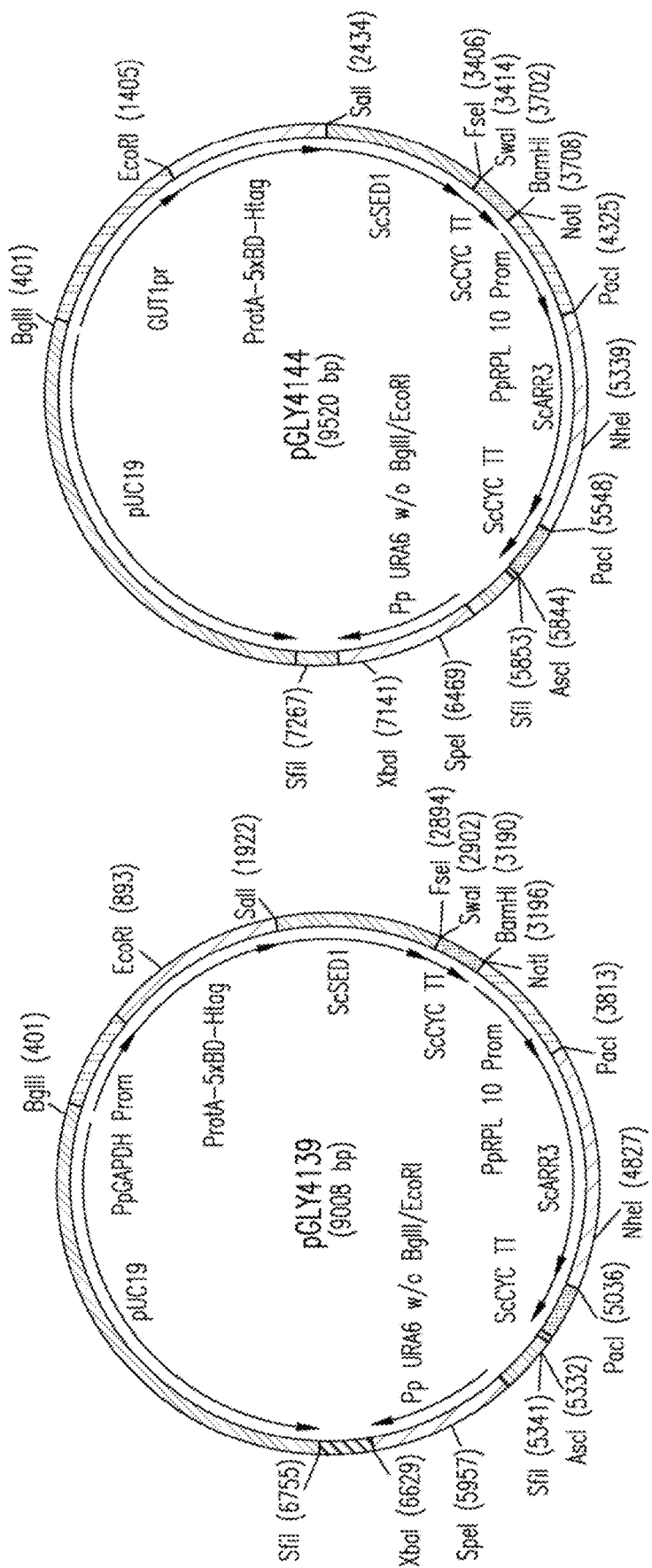
FIG. 15 shows maps of plasmid vectors pGLY439 and pGLY4144.

The AOX promoter from the Protein A/SED1 fusion protein plasmid pGLY4136 was replaced either by the PpGAPDH promoter resulting in plasmid pGLY4139 or the GUT1 promoter producing the plasmid pGLY4144 (FIG. 15). The PpGAPDH promoter is induced in dextrose and at about 80% of that level in glycerol, while the GUT1 promoter is induced in glycerol and repressed in dextrose. pGLY4139 was transfected into yGLY4134, expressing anti-Her2 antibody under control of the AOX promoter. Additionally, pGLY4144 has been transfected into strain yGLY5434 (yGLY2696 transfected with pGLY4142), in which anti-Her2 expression is regulated by the GAPDH promoter.

Strain yGLY4134 transfected with pGLY4136, in which expression of the Protein A/SED1 fusion protein and the anti-Her2 antibody are both regulated by the AOX promoter, was grown in 600 μL BMGY (glycerol as carbon source) in a 96 deep well plate or 50 mL BMGY in a 250 mL shake flask for two days. The cells were collected by centrifugation and the supernatant was discarded. The cells were induced by incubation overnight in 300 μL or 25 mL BMMY (methanol as carbon source) with PMTi inhibitor.

Strain yGLY4134 transfected with pGLY4139, in which expression of the Protein A/SED1 fusion protein is regulated by the PpGAPDH promoter and expression of the anti-Her2 antibody regulated by the AOX promoter, was grown in BMGY (glycerol as carbon source) and induced in BMMY with PMTi inhibitor (methanol as carbon source).

Strain yGLY5434 transfected with pGLY4144, in which expression of the Protein A/SED1 fusion protein is regulated by the GUT1 promoter and expression of the anti-Her2 antibody is regulated by the GAPDH promoter, was grown in BMGY (glycerol as carbon source) and induced in BMDY with PMTi inhibitor (dextrose as carbon source). Dextrose inhibits transcription from the GUT1 promoter. After induction, all three strains were labeled with goat anti human IgG (H+L)-Alexa Fluor®488 as described in Example 1. In general, growth can be between 1.5 days to 3 days and induction between 1 to 2 days. Strains are usually grown for 2 days and then induced for another 2 days: afterwards the analysis is done.

Figure 16:
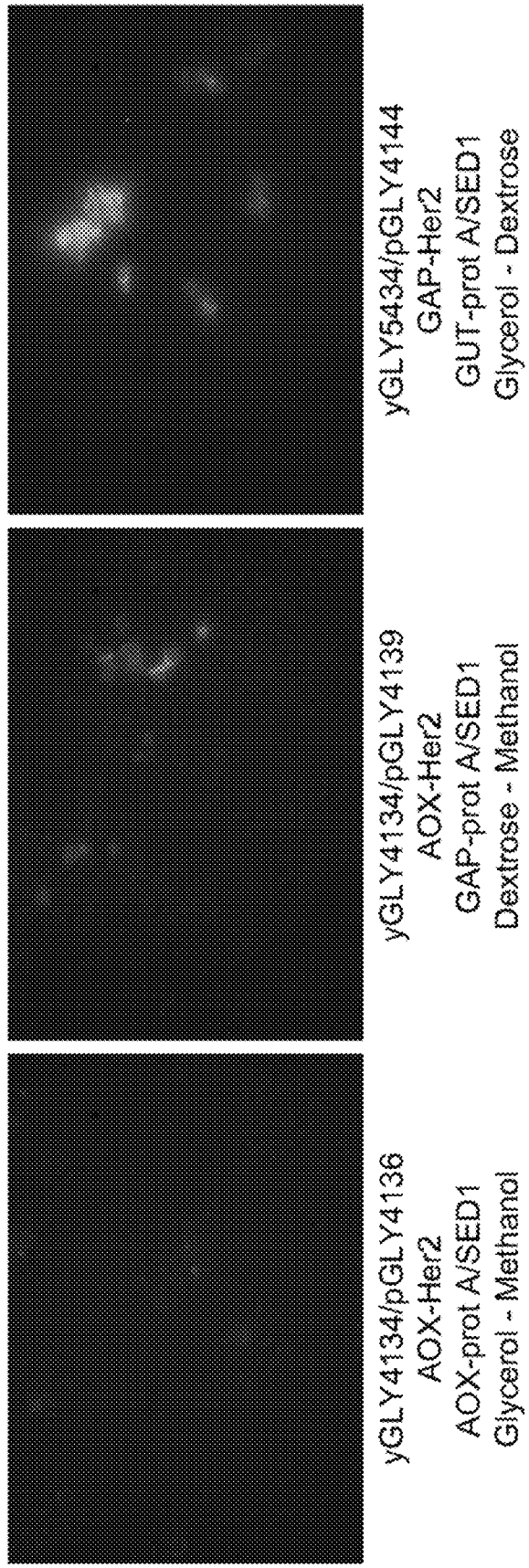
FIG. 16 shows fluorescence microscopy results of strain yGLY4134 (AOX promoter-anti-Her2 antibody) transfected with pGLY4136 (AOX promoter-Protein A/SED1 fusion protein), strain yGLY4134 (AOX promoter-anti-Her2 antibody) transfected with pGLY4139 (GAPDH promoter-Protein A/SED1 fusion protein), and strain yGLY5434(GAPDH promoter-anti-Her2 antibody) transfected with pGLY4139 (GUT1 promoter-Protein A/SED1 fusion protein). Goat anti-human IgG (H+L)-Alexa Fluor® 488 was used for detection of anti-antibody bound to the Protein A/SED1 fusion protein anchored to the cell surface.

FIG. 16 illustrates the results of cell surface staining of the above strains. As was shown in Example 5, co-expression of the Protein A/SED1 fusion protein and anti-Her2 antibody, both under the strong AOX promoter (yGLY4134 transfected with pGLY4136) does not show any cell surface labeling. Expression of the Protein A/SED1 fusion protein under the GAPDH promoter during growth in glycerol and the expression of anti-Her2 antibody regulated by the AOX promoter during induction with methanol (yGLY4134 transfected with pGLY4139) shows some weak but visible cell surface labeling. In this case the Protein A/SED1 fusion protein is still expressed at some level during induction of the antibody because the GAPDH promoter is not completely repressed under methanol induction conditions. However, expression of the Protein A/SED1 fusion protein under the GUT1 promoter during growth in glycerol followed by induction of the anti-Her2 antibody regulated by the GAPDH promoter during induction in dextrose (YGLY5434 transfected with pGLY4144) showed strong cell surface labeling. In this case, the Protein A/SED1 fusion protein was not expressed under antibody induction conditions because the GUT1 promoter is completely repressed in dextrose.

FIG. 17 is a chart that illustrates the expected expression patterns of Protein A/SED1 fusion protein and antibody under the control of different combinations of promoters. Expression of the Protein A/SED1 fusion protein and the antibody under the strong AOX promoter, which is repressed in the glycerol growth phase and induced in the methanol induction phase, led to no detectable cell surface display. Likely, co-expression leads to a Protein A/SED1 fusion protein—antibody complex in the ER, which does not secrete to the cell surface or is degraded.

Expression of the Protein A/SED1 fusion protein under the GAPDH promoter during growth in glycerol and expression of the antibody under the AOX promoter during induction in methanol resulted in weak cell surface display. In this case, the Protein A/SED1 fusion protein is still expressed at some level during induction of the antibody because the GAPDH promoter is not repressed completely under methanol induction conditions. This means that under induction conditions, there might be complex formation between the Protein A/SED1 fusion protein and the antibody in the ER, which then clogs the secretory pathway leading to only a small amount of Protein A/SED1 fusion protein at the cell surface.

Expression of the Protein A/SED1 fusion protein under the GUT1 promoter during growth in glycerol followed by expression of the antibody under the GAPDH promoter while simultaneously repressing expression of the Protein A/SED1 fusion protein during induction of antibody expression with dextrose led to strong cell surface display. Thus, when the Protein A/SED1 fusion protein is expressed first and then completely repressed during antibody induction, the Protein A/SED1 fusion protein is secreted to the cell wall where it can capture the antibody when it is secreted. Although the antibody is expressed at some level during Protein A/SED1 fusion protein growth because the GAPDH promoter is not repressed under glycerol, the level of expression of the antibody appears to be low enough to not interfere with the Protein A/SED1 fusion protein secretion.

To demonstrate that the cell surface display of whole antibody by Protein A/SED1 fusion protein regulated under the GUT1 promoter is functional for different antibodies, the anti-CD20 antibody expressing strain yGLY5757 was also transfected with plasmid pGLY4144, which encodes Protein A/SED1 fusion protein whose expression is regulated the GUT1 promoter. Strain yGLY5757 is strain yGLY2696 transfected with the plasmid pGLY4078. Plasmid pGLY4078 encodes the heavy and light chain of the anti-CD20 antibody under the regulation of the GAPDH promoter.

Figure 18:
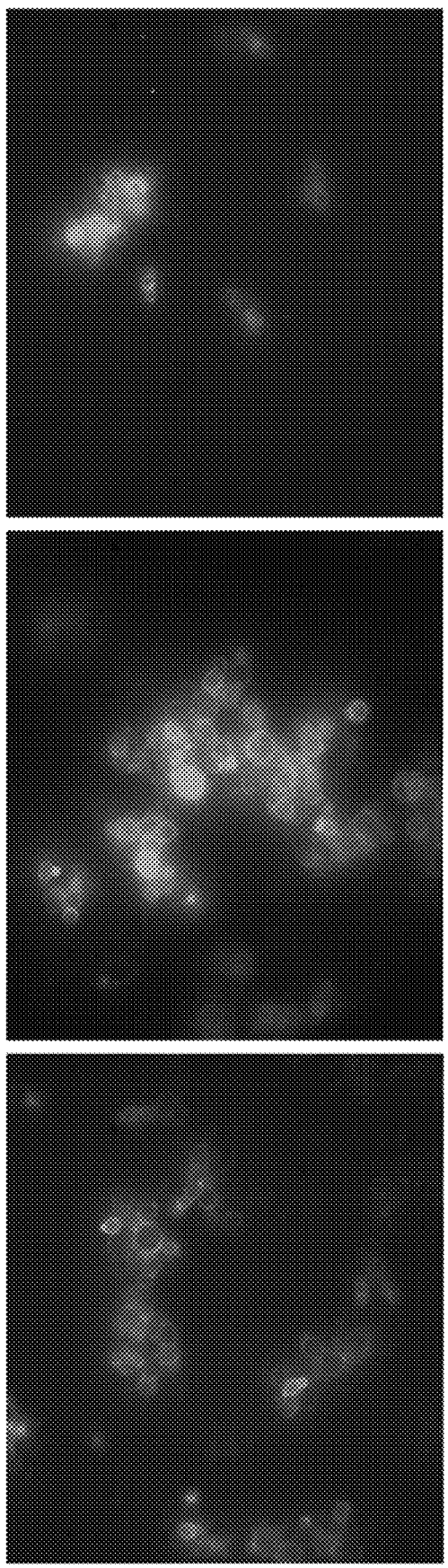
FIG. 18 shows fluorescence microscopy results of strains yGLY5757 (expresses anti-CD20 antibody under control of the GAPDH promoter) and yGLY5434 (expresses anti-Her2 antibody under control of the GAPDH promoter), each transfected with pGLY4144 encoding Protein A/SED1 fusion protein under the control of the GUT1 promoter. Protein A/SED1 fusion protein expression (GUT1 promoter) was induced first under glycerol conditions; then antibody expression from the GAPDH promoter was induced under dextrose conditions, which also inhibits expression of the Protein A/SED1 fusion protein. Goat anti-human IgG (H+L)-Alexa Fluor® 488 was used for detection of anti-antibody bound to the Protein A/SED1 fusion protein anchored to the cell surface.

Strain yGLY5757 expressing the anti-CD20 antibody operably linked to the GAPDH promoter and transfected with pGLY4144 (encodes Protein A/SED1 fusion protein under control of the GUT1 promoter) and strain yGLY5434 expressing the anti-Her2 antibody operably linked to the GAPDH promoter transfected with pGLY4144 were grown in glycerol for Protein A/SED1 fusion protein expression followed by induction in dextrose for antibody expression and secretion as described for FIG. 6. Strong cell surface staining was observed for both antibodies (FIG. 18). This demonstrates that temporal regulation enables different antibodies and not just the anti-Her2 antibodies to be displayed on the yeast surface by an anchored antibody binding moiety.

Figure 19A:
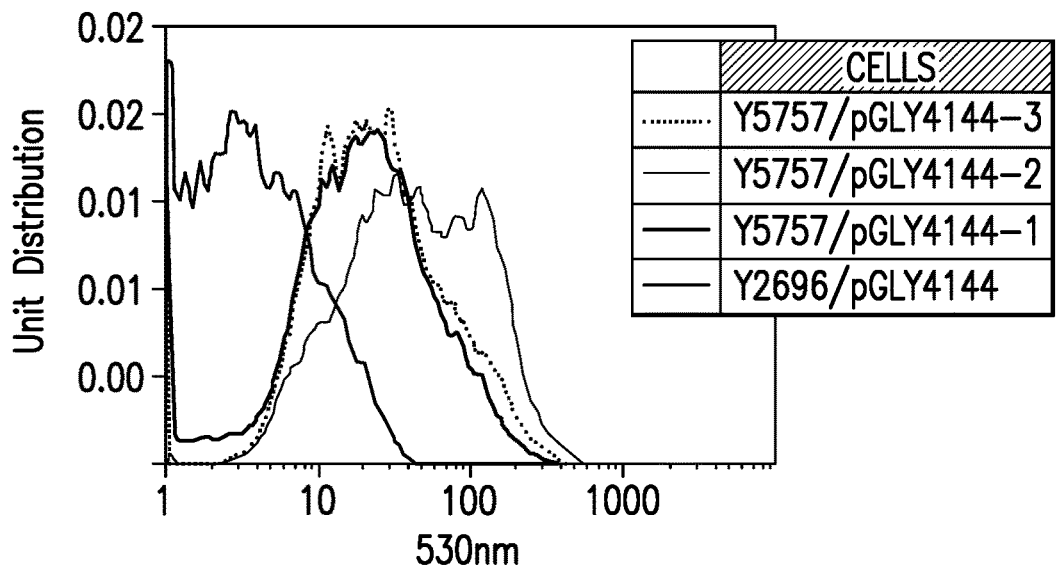
FIG. 19A and FIG. 19B show the results of FACS sorting of the cells shown in FIG. 18.
Figure 19B:
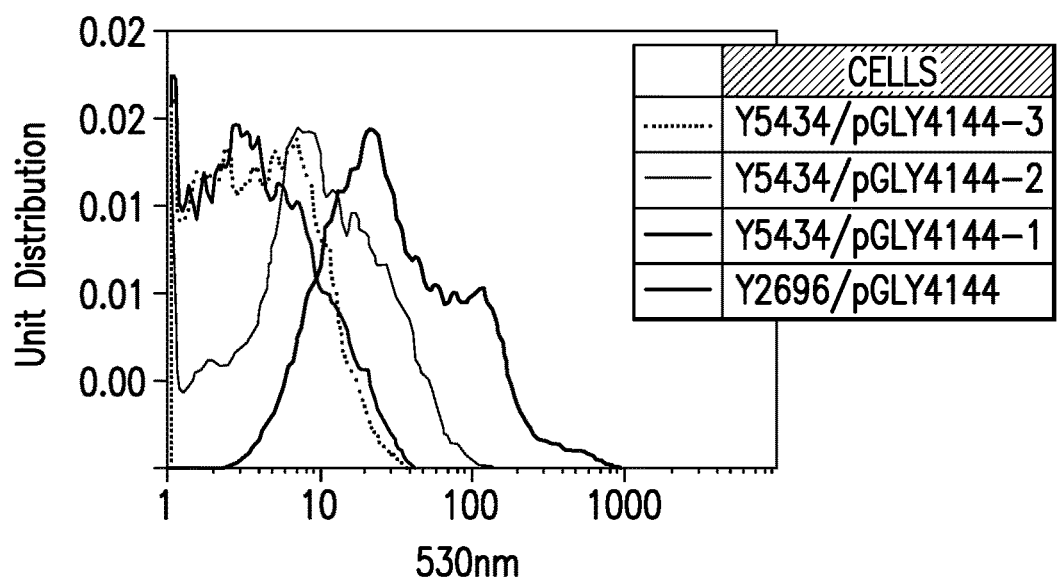

FIG. 19A-19B show the results of FACS sorting of the samples from FIG. 8. The anti-Her2 expressing strain yGLY5757 transfected with pGLY4144, the anti-CD20 expressing strain yGLY5434 transfected with pGLY4144 and the empty strain yGLY2696 transfected with pGLY4144 were grown in glycerol and then induced in dextrose. Cells were labeled with goat anti human IgG (H+L)-Alexa Fluor®488 and analyzed by FACS sorting. As shown in FIG. 19A and FIG. 19B, the empty strain without antibody expression displayed background fluorescent staining while for three clones of the anti-CD20 expressing strain, the fluorescence was shifted to the right showing cell surface labeling. The same was also seen for the anti-Her2 expressing strain. One clone of this strain showed no cell surface labeling, which could be a false positive from a transfection that does not express the antibody or the anchor. These results demonstrate that the cells displaying whole antibodies can be sorted using FACS sorting.

TABLE 1

BRIEF DESCRIPTION OF THE SEQUENCES

| SEQ ID NO: | Description | Sequence |
|---|---|---|
| 1 | PCR primer hPDI/UP1 | AGCGCTGACGCCCCCGAGGAGGAGGACCAC |
| 2 | PCR primer hPDI/LP-PacI | CCTTAATTAATTACAGTTCATCATGCACAGCTTTCTGAT CAT |
| 3 | PCR primer PB248 | ATGAATTCAGGC CATATCGGCCATTGTTTACTGTGCG CCCACAGTAG |

TABLE 1-continued

BRIEF DESCRIPTION OF THE SEQUENCES

| SEQ ID NO: | Description | Sequence |
|---|---|---|
| 4 | PCR primer PB249 | ATGTTTA AACGTGAGGATTACTGGTGATGAAAGAC |
| 5 | PCR primer PB250 | AGACTAGTCTATTTGGAG ACATTGACGGATCCAC |
| 6 | PCR primer PB251 | ATCTCGAGAGGCCATGCAGGCCAACCACAAGATGAAT CAAATTTTG |
| 7 | PCR primer PpPDI/UPi-1 | GGTGAGGTTGAGGTCCCAAGTGACTATCAAGGTC |
| 8 | PCR primer PpPDI/LPi-1 | GACCTTGATAGTCACTTGGGACCTCAACCTCACC |
| 9 | PCR primer PpPDI/UPi-2 | CGCCAATGATGAGGATGCCTCTTCAAAGGTTGTG |
| 10 | PCR primer PpPDI/LPi-2 | CACAACCTTTGAAGAGGCATCCTCATCATTGGCG |
| 11 | PCR primer PpPDI-5'/UP | GGCGATTGCATTCGCGAC TGTATC |
| 12 | PCR primer hPDI-3'/LP | CCTAGAGAGCGGTGG CCAAGATG |
| 13 | PCR primer hPDI/UP | GTGGCCACACCAGGGGGC ATGGAAC |
| 14 | PCR primer hPDI-3'/LP | CCTAGAGAGCGGTGG CCAAGATG |
| 15 | PCR primer hGRP94/UP1 | AGCGCTGACGATGAAGTTGATGTGGATGGTACA GTAG |
| 16 | PCR primer hGRP94/LP1 | GGCCGGCCTTACAATTCATCATG TTCAGCTGTAGATTC |
| 17 | PCR primer PMT1-KO1 | TGAACCCATCTGTAAATAGAATGC |
| 18 | PCR primer PMT1-KO2 | GTGTCACCTAAATCGTATGTGCCCATTTACTGGA AGCTGCTAACC |
| 19 | PCR primer PMT1-KO3 | CTCCCTATAGTGAGTCGTATTCATCATTGTACTTT GGTATATTGG |
| 20 | PCR primer PMT1-KO4 | TATTTGTACCTGCGTCCTGTTTGC |
| 21 | PCR primer PR29 | CACATACGATTTAGGTGACAC |
| 22 | PCR primer PR32 | AATACGACTCACTATAGGGAG |
| 23 | PCR primer PMT4-KO1 | TGCTCTCCGCGTGCAATAGAAACT |
| 24 | PCR primer PMT4-KO2 | CTCCCTATAGTGAGTCGTATTCACAGTGTACCATCT TTCATCTCC |
| 25 | PCR primer PMT4-KO3 | GTGTCACCTAAATCGTATGTGAACCTAACTCTAA TTCTTCAAAGC |
| 26 | PCR primer PMT4-KO4 | ACTAGGGTATATAATTCCCAAGGT |

TABLE 1-continued

BRIEF DESCRIPTION OF THE SEQUENCES

| SEQ ID NO: | Description | Sequence |
|---|---|---|
| 27 | Pre-pro α-mating factor signal peptide (ScαMTprepro) (DNA) | ATG AGA TTC CCA TCC ATC TTC ACT GCT GTT TTG TTC GCT GCT TCT TCT GCT TTG GCT |
| 28 | Pre-pro α-mating factor signal peptide (protein) | MRFPSIFTAVLFAASSALA |
| 29 | Anti-Her2 Heavy chain (VH + IgG1 constant region) (DNA) | GAGGTTCAGTTGGTTGAATCTGGAGGAGGATTGGTTCA<br>ACCTGGTGGTTCTTTGAGATTGTCCTGTGCTGCTTCCGG<br>TTTCAACATCAAGGACACTTACATCCACTGGGTTAGAC<br>AAGCTCCAGGAAAGGGATTGGAGTGGGTTGCTAGAAT<br>CTACCCAACTAACGGTTACACAAGATACGCTGACTCCG<br>TTAAGGGAAGATTCACTATCTCTGCTGACACTTCCAAG<br>AACACTGCTTACTTGCAGATGAACTCCTTGAGAGCTGA<br>GGATACTGCTGTTTACTACTGTTCCAGATGGGGTGGTG<br>ATGGTTTCTACGCTATGGACTACTGGGGTCAAGGAACT<br>TTGGTTACTGTTTCCTCCGCTTCTACTAAGGGACCATCT<br>GTTTTCCCATTGGCTCCATCTTCTAAGTCTACTTCCGGT<br>GGTACTGCTGCTTTGGGATGTTTGGTTAAAGACTACTT<br>CCCAGAGCCAGTTACTGTTTCTTGGAACTCCGGTGCTT<br>TGACTTCTGGTGTTCACACTTTCCCAGCTGTTTTGCAAT<br>CTTCCGGTTTGTACTCTTTGTCCTCCGTTGTTACTGTTC<br>CATCCTCTTCCTTGGGTACTCAGACTTACATCTGTAACG<br>TTAACCACAAGCCATCCAACACTAAGGTTGACAAGAA<br>GGTTGAGCCAAAGTCCTGTGACAAGACTCATACTTGTC<br>CACCATGTCCAGCTCCAGAATTGTTGGGTGGTCCTTCC<br>GTTTTTTTGTTCCCACCAAAGCCAAAGGACACTTTGAT<br>GATCTCCAGAACTCCAGAGGTTACATGTGTTGTTGTTG<br>ACGTTTCTCACGAGGACCCAGAGGTTAAGTTCAACTGG<br>TACGTTGACGGTGTTGAAGTTCACAACGCTAAGACTAA<br>GCCAAGAGAGGAGCAGTACAACTCCACTTACAGAGTT<br>GTTTCCGTTTTGACTGTTTTGCACCAGGATTGGTTGAAC<br>GGAAAGGAGTACAAGTGTAAGGTTTCCAACAAGGCTT<br>TGCCAGCTCCAATCGAAAAGACTATCTCCAAGGCTAAG<br>GGTCAACCAAGAGAGCCACAGGTTTACACTTTGCCACC<br>ATCCAGAGATGAGTTGACTAAGAACCAGGTTTCCTTGA<br>CTTGTTTGGTTAAGGGATTCTACCCATCCGACATTGCT<br>GTTGAATGGGAGTCTAACGGTCAACCAGAGAACAACT<br>ACAAGACTACTCCACCTGTTTTGGACTCTGACGGTTCC<br>TTTTTCTTGTACTCCAAGTTGACTGTTGACAAGTCCAGA<br>TGGCAACAGGGTAACGTTTTCTCCTGTTCCGTTATGCA<br>TGAGGCTTTGCACAACCACTACACTCAAAAGTCCTTGT<br>CTTTGTCCCCTGGTAAGTAA |
| 30 | Anti-Her2 Heavy chain (VH + IgG1 constant region) (protein) | EVQLVESGGGLVQPGGSLRLSCAASGFNIKDTYIHWVRQ<br>APGKGLEWVARIYPTNGYTRYADSVKGRFTISADTSKNT<br>AYLQMNSLRAEDTAVYYCSRWGGDGFYAMDYWGQGT<br>LVTVSSASTKGPSVFPLAPSSKSTSGGTAALGCLVKDYFP<br>EPVTVSWNSGALTSGVHTFPAVLQSSGLYSLSSVVTVPSS<br>SLGTQTYICNVNHKPSNTKVDKKVEPKSCDKTHTCPPCP<br>APELLGGPSVFLFPPKPKDTLMISRTPEVTCVVVDVSHED<br>PEVKFNWYVDGVEVHNAKTKPREEQYNSTYRVVSVLTV<br>LHQDWLNGKEYKCKVSNKALPAPIEKTISKAKGQPREPQ<br>VYTLPPSRDELTKNQVSLTCLVKGFYPSDIAVEWESNGQP<br>ENNYKTTPPVLDSDGSFFLYSKLTVDKSRWQQGNVFSCS<br>VMHEALHNHYTQKSLSLSPGK |
| 31 | Anti-Her2 light chain (VL + Kappa constant region) (DNA) | GACATCCAAATGACTCAATCCCCATCTTCTTTGTCTGCT<br>TCCGTTGGTGACAGAGTTACTATCACTTGTAGAGCTTC<br>CCAGGACGTTAATACTGCTGTTGCTTGGTATCAACAGA<br>AGCCAGGAAAGGCTCCAAAGTTGTTGATCTACTCCGCT<br>TCCTTCTTGTACTCTGGTGTTCCATCCAGATTCTCTGGT<br>TCCAGATCCGGTACTGACTTCACTTTGACTATCTCCTCC<br>TTGCAACCAGAAGATTTCGCTACTTACTGTCAGCA<br>GCACTACACTACTCCACCAACTTTCGGACAGGGTACTA<br>AGGTTGAGATCAAGAGAACTGTTGCTGCTCCATCCGTT<br>TTCATTTTCCCACCATCCGACGAACAGTTGAAGTCTGG<br>TACAGCTTCCGTTGTTTGTTTGTTGAACAACTTCTACCC<br>AAGAGAGGCTAAGGTTCAGTGGAAGGTTGACAACGCT |

TABLE 1-continued

BRIEF DESCRIPTION OF THE SEQUENCES

| SEQ ID NO: | Description | Sequence |
|---|---|---|
| | | TTGCAATCCGGTAACTCCCAAGAATCCGTTACTGAGCA<br>AGACTCTAAGGACTCCACTTACTCCTTGTCCTCCACTTT<br>GACTTTGTCCAAGGCTGATTACGAGAAGCACAAGGTTT<br>ACGCTTGTGAGGTTACACATCAGGGTTTGTCCTCCCCA<br>GTTACTAAGTCCTTCAACAGAGGAGAGTGTTAA |
| 32 | Anti-Her2 light chain (VL + Kappa constant region) | DIQMTQSPSSLSASVGDRVTITCRASQDVNTAVAWYQQK<br>PGKAPKLLIYSASFLY<br>SGVPSRFSGSRSGTDFTLTISSLQPEDFATYYCQQHYTTPP<br>TFGQGTKVEIKRTVAAPSVFIFPPSDEQLKSGTASVVC<br>LNNFYPREAKVQWKVDNALQSGNSQESVTEQ<br>DSKDSTYSLSSTLTLSKADYEKHKVYACEVTHQGLSSPV<br>TKSFNRGEC |
| 33 | Alpha amylase signal peptide (from *Aspergillus niger* α-amylase) (DNA) | ATGGTTGCTT GGTGGTCCTT GTTCTTGTAC<br>GGATTGCAAG TTGCTGCTCC AGCTTTGGCT |
| 34 | Alpha amylase signal peptide (from *Aspergillus niger* α-amylase) | MVAWWSLFLY GLQVAAPALA |
| 35 | Anti-CD20 Light chain Variable Region (DNA) | GAGATCGTTT TGACACAGTC CCCAGCTACT<br>TTGTCTTTGT CCCCAGGTGA AAGAGCTACA<br>TTGTCCTGTA GAGCTTCCCA ATCTGTTTCC<br>TCCTACTTGG CTTGGTATCA ACAAAAGCCA<br>GGACAGGCTC CAAGATTGTT GATCTACGAC<br>GCTTCCAATA GAGCTACTGG TATCCCAGCT<br>AGATTCTCTG GTTCTGGTTC CGGTACTGAC<br>TTCACTTTGA CTATCTCTTC CTTGGAACCA<br>GAGGACTTCG CTGTTTACTA CTGTCAGCAG<br>AGATCCAATT GGCCATTGAC TTTCGGTGGT<br>GGTACTAAGG TTGAGATCAA AGCGTACGGTT<br>GCTGCTCCTT CCGTTTTCAT TTTCCCACCA<br>TCCGACGAAC AATTGAAGTC TGGTACCCAA TTCGCCC |
| 36 | Anti-CD20 Light chain Variable Region | EIVLTQSPAT LSLSPGERAT LSCRASQSVS<br>SYLAWYQQKP GQAPRLLIYD ASNRATGIPA<br>RFSGSGSGTD FTLTISSLEP EDFAVYYCQQ<br>RSNWPLTFGG GTKVEIKRTV<br>AAPSVFIFPPSDEQLKSGTQFA |
| 37 | Anti-CD20 Heavy chain Variable Region (DNA) | GCTGTTCAGC TGGTTGAATC TGGTGGTGGA<br>TTGGTTCAAC CTGGTAGATC CTTGAGATTG<br>TCCTGTGCTG CTTCCGGTTT TACTTTCGGT<br>GACTACACTA TGCACTGGGT TAGACAAGCT<br>CCAGGAAAGG GATTGGAATG GGTTTCCGGT<br>ATTTCTTGGA ACTCCGGTTC CATTGGTTAC<br>GCTGATTCCG TTAAGGGAAG ATTCACTATC<br>TCCAGAGACA ACGCTAAGAA CTCCTTGTAC<br>TTGCAGATGA ACTCCTTGAG AGCTGAGGAT<br>ACTGCTTTGT ACTACTGTAC TAAGGACAAC<br>CAATACGGTT CTGGTTCCAC TTACGGATTG<br>GGAGTTTGGG GACAGGGAAC TTTGGTTACT<br>GTCTCGAGTC CTTCTACTAA GGGACCATCC<br>GTTTTTCCAT TGGCTCCATC CTCTAAGTCT<br>ACTTCCGGTG GTACCCAATT CGCCC |
| 38 | Anti-CD20 Heavy chain Variable Region | AVQLVESGGG LVQPGRSLRL SCAASGFTFG<br>DYTMHWVRQA PGKGLEWVSG ISWNSGSIGY<br>ADSVKGRFTI SRDNAKNSLY LQMNSLRAED<br>TALYYCTKDN QYGSGSTYGL GVWGQGTLVT<br>VSSASTKGPS VFPLAPSSKS TSGGTQFA |
| 39 | human PDI Gene (DNA) | GACGCCCCCG AGGAGGAGGA CCACGTCTTG GTGCTGCGGAA<br>AAGCAACTTC GCGGAGGCGC TGGCGGCCCA CAAGTACCCGC<br>CGGTGGAGTT CCATGCCCCC TGGTGTGGCC ACTGCAAGGCT |

TABLE 1-continued

BRIEF DESCRIPTION OF THE SEQUENCES

| SEQ ID NO: | Description | Sequence |
|---|---|---|
| | | CTGGCCCCTGAGTATGCCAAAGCCGCTGGGAAGCTGAAGGC<br>AGAAGGTTCCGAGATCAGGTTGGCCAAGGTGGACGCCACGG<br>AGGAGTCTGACCTAGCCCAGCAGTACGGCGTGCGCGGCTAT<br>CCCACCATCAAGTTCTTCAGGAATGGAGACACGGCTTCCCC<br>CAAGGAATATACAGCTGGCAGAGAGGCTGATGACATCGTGA<br>ACTGGCTGAAGAAGCGCACGGGCCCGGCTGCCACCACCCTG<br>CCTGACGGCGCAGCTGCAGAGTCCTTGGTGGAGTCCAGCGA<br>GGTGGCCGTCATCGGCTTCTTCAAGGACGTGGAGTCGGACT<br>CTGCCAAGCAGTTTTTGCAGGCAGCAGAGGCCATCGATGAC<br>ATACCATTTGGGATCACTTCCAACAGTGACGTGTTCTCCAAA<br>TACCAGCTCGACAAAGATGGGGTTGTCCTCTTTAAGAAGTTT<br>GATGAAGGCCGGAACAACTTTGAAGGGGAGGTCACCAAGG<br>AGAACCTGCTGGACTTTATCAAACACAACCAGCTGCCCCTT<br>GTCATCGAGTTCACCGAGCAGACAGCCCCGAAGATTTTTGG<br>AGGTGAAATCAAGACTCACATCCTGCTGTTCTTGCCCAAGA<br>GTGTGTCTGACTATGACGGCAAACTGAGCAACTTCAAAACA<br>GCAGCCGAGAGCTTCAAGGGCAAGATCCTGTTCATCTTCAT<br>CGACAGCGACCACACCGACAACCAGCGCATCCTCGAGTTCT<br>TTGGCCTGAAGAAGGAAGAGTGCCCGGCCGTGCGCCTCATC<br>ACCTTGGAGGAGGAGATGACCAAGTACAAGCCCGAATCGG<br>AGGAGCTGACGGCAGAGAGGATCACAGAGTTCTGCCACCGC<br>TTCCTGGAGGGCAAAATCAAGCCCCACCTGATGAGCCAGGA<br>GCTGCCGGAGGACTGGGACAAGCAGCCTGTCAAGGTGCTTG<br>TTGGGAAGAACTTTGAAGACGTGGCTTTTGATGAGAAAAAA<br>AACGTCTTTGTGGAGTTCTATGCCCCATGGTGTGGTCACTGC<br>AAACAGTTGGCTCCCATTTGGGATAAACTGGGAGAGACGTA<br>CAAGGACCATGAGAACATCGTCATCGCCAAGATGGACTCGA<br>CTGCCAACGAGGTGGAGGCCGTCAAAGTGCACGGCTTCCCC<br>ACACTCGGGTTCTTTCCTGCCAGTGCCGACAGGACGGTCATT<br>GATTACAACGGGGAACGCACGCTGGATGGTTTTAAGAAATT<br>CCTAGAGAGCGGTGGCCAAGATGGGCAGGGGATGTTGAC<br>GACCTCGAGGACCTCGAAGAAGCAGAGGAGCCAGACATGG<br>AGGAAGACGATGACCAGAAAGCTGTGAAAGATGAACTGTA<br>A |
| 40 | human PDI Gene (protein) | DAPEEEDHVLVLRKSNFAEALAAHKYPPVEFHAPWCGHCKAL<br>APEYAKAAGKLKAEGSEIRLAKVDATEESDLAQQYGVRGYPTI<br>KFFRNGDTASPKEYTAGREADDIVNWLKKRTGPAATTLPDGA<br>AAESLVESSEVAVIGFFKDVESDSAKQFLQAAEAIDDIPFGITSN<br>SDVFSKYQLDKDGVVLFKKFDEGRNNFEGEVTKENLLDFIKHN<br>QLPLVIEFTEQTAPKIFGGEIKTHILLFLPKSVSDYDGKLSNFKT<br>AAESFKGKILFIFIDSDHTDNQRILEFFGLKKEECPAVRLITLEEE<br>MTKYKPESEELTAERITEFCHRFLEGKIKPHLMSQELPEDWDK<br>QPVKVLVGKNFEDVAFDEKKNVFVEFYAPWCGHCKQLAPIW<br>DKLGETYKDHENIVIAKMDSTANEVEAVKVHGFPTLGFFPASA<br>DRTVIDYNGERTLDGFKKFLESGGQDGAGDVDDLEDLEEAEEP<br>DMEEDDDQKAVHDEL |
| 41 | *Pichia pastoris* PDI1 Gene (DNA) | ATGCAATTCAACTGGAATATTAAAACTGTGGCAAGTATTTT<br>GTCCGCTCTCACACTAGCACAAGCAAGTGATCAGGAGGCTA<br>TTGCTCCAGAGGACTCTCATGTCGTCAAATTGACTGAAGCC<br>ACTTTTGAGTCTTTCATCACCAGTAATCCTCACGTTTTGGCA<br>GAGTTTTTTGCCCCTTGGTGTGGTCACTGTAAGAAGTTGGGC<br>CCTGAACTTGTTTCTGCTGCCGAGATCTTAAAGGACAATGA<br>GCAGGTTAAGATTGCTCAAATTGATTGTACGGAGGAGAAGG<br>AATTATGTCAAGGCTACGAAATTAAAGGGTATCCTACTTTG<br>AAGGTGTTCCATGGTGAGGTTGAGGTCCCAAGTGACTATCA<br>AGGTCAAAGACAGAGCCAAAGCATTGTCAGCTATATGCTAA<br>AGCAGAGTTTACCCCCTGTCAGTGAAATCAATGCAACCAAA<br>GATTTAGACGACACAATCGCCGAGGCAAAAGAGCCCGTGAT<br>TGTGCAAGTACTACCGGAAGATGCATCCAACTTGGAATCTA<br>ACACCACATTTTACGGAGTTGCCGGTACTCTCAGAGAGAAA<br>TTCACTTTTGTCTCCACTAAGTCTACTGATTATGCCAAAAAA<br>TACACTAGCGACTCGACTCCTGCCTATTTGCTTGTCAGACCT<br>GGCGAGGAACCTAGTGTTTACTCTGGTGAGGAGTTAGATGA<br>GACTCATTTGGTGCACTGGATTGATATTGAGTCCAAACCTCT<br>ATTTGGAGACATTGACGGATCCACCTTCAAATCATATGCTG<br>AAGCTAACATCCCTTTAGCCTACTATTTCTATGAGAACGAAG<br>AACAACGTGCTGCTGCCGATATTATTAAACCTTTTGCTA<br>AAGAGCAACGTGGCAAAATTAACTTGTTGGCTTAGATGCC<br>GTTAAATTCGGTAAGCATGCCAAGAACTTAAACATGGATGA<br>AGAGAAACTCCCTCTATTTGTCATTCATGATTTGGTGAGCAA<br>CAAGAAGTTTGGAGTTCCTCAAGACCAAGAATTGACGAACA<br>AAGATGTGACCGAGCTGATTGAGAAATTCATCGCAGGAGAG |

TABLE 1-continued

BRIEF DESCRIPTION OF THE SEQUENCES

| SEQ ID NO: | Description | Sequence |
|---|---|---|
| | | GCAGAACCAATTGTGAAATCAGAGCCAATTCCAGAAATTCA<br>AGAAGAGAAAGTCTTCAAGCTAGTCGGAAAGGCCCACGAT<br>GAAGTTGTCTTCGATGAATCTAAAGATGTTCTAGTCAAGTAC<br>TACGCCCCTTGGTGTGGTCACTGTAAGAGAATGGCTCCTGCT<br>TATGAGGAATTGGCTACTCTTTACGCCAATGATGAGGATGC<br>CTCTTCAAAGGTTGTGATTGCAAAACTTTGATCACACTTTGAA<br>CGATGTCGACAACGTTGATATTCAAGGTTATCCTACTTTGAT<br>CCTTTATCCAGCTGGTGATAAATCCAATCCTCAACTGTATGA<br>TGGATCTCGTGACCTAGAATCATTGGCTGAGTTTGTAAAGG<br>AGAGAGGAACCCACAAAGTGGATGCCCTAGCACTCAGACC<br>AGTCGAGGAAGAAAAGGAAGCTGAAGAAGAAGCTGAAAGT<br>GAGGCAGACGCTCACGACGAGCTTTAA |
| 42 | Pichia pastoris PDI1 Gene (protein) | MQFNWNIKTVASILSALTLAQASDQEAIAPEDSHVVKLTEATF<br>ESFITSNPHVLAEFFAPWCGHCKKLGPELVSAAEILKDNEQVKI<br>AQIDCTEEKELCQGYEIKGYPTLKVFHGEVEVPSDYQGQRQSQ<br>SIVSYMLKQSLPPVSEINATKDLDDTIAEAKEPVIVQVLPEDAS<br>NLESNTTFYGVAGTLREKFTFVSTKSTDYAKKYTSDSTPAYLL<br>VRPGEEPSVYSGEELDETHLVHWIDIESKPLFGDIDGSTFKSYA<br>EANIPLAYYFYENEEQRAAAADIIKPFAKEQRGKINFVGLDAV<br>KFGKHAKNLNMDEEKLPLFVIHDLVSNKKFGVPQDQELTNKD<br>VTELIEKFIAGEAEPIVKSEPIPEIQEEKVFKLVGKAHDEVVFDE<br>SKDVLVKYYAPWCGHCKRMAPAYEELATLYANDEDASSKVV<br>IAKLDHTLNDVDNVDIQGYPTLILYPAGDKSNPQLYDGSRDLE<br>SLAEFVKERGTHKVDALALRPVEEEKEAEEEAESEADAHDEL |
| 43 | human GRP94 Gene (DNA) | GATGATGAAGTTGACGTTGACGGTACTGTTGAAGAGGACTT<br>GGGAAAGTCTAGAGAGGGTTCCAGAACTGACGACGAAGTT<br>GTTCAGAGAGAGGAAGAGGCTATTCAGTTGGACGGATTGAA<br>CGCTTCCCAAATCAGAGAGTTGAGAGAGAAGTCCGAGAAGT<br>TCGCTTTCCAAGCTGAGGTTAACAGAATGATGAAATTGATT<br>ATCAACTCCTTGTACAAGAACAAAGAGATTTTCTTGAGAGA<br>GTTGATCTCTAACGCTTCTGACGCTTTGGACAAGATCAGATT<br>GATCTCCTTGACTGACGAAAACGCTTTGTCCGGTAACGAAG<br>AGTTGACTGTTAAGATCAAGTGTGACAAAGAGAAGAACTTG<br>TTGCACGTTACTGACACTGGTGTTGGAATGACTAGAGAAGA<br>GTTGGTTAAGAACTTGGGTACTATCGCTAAGTCTGGTACTTC<br>CGAGTTCTTGAACAAGATGACTGAGGCTCAAGAAGATGGTC<br>AATCCACTTCCGAGTTGATTGGTCAGTTCGGTGTTGGTTTCT<br>ACTCCGCTTTCTTGGTTGCTGACAAGGTTATCGTTACTTCCA<br>AGCACAACAACGACACTCAACACATTTGGGAATCCGATTCC<br>AACGAGTTCTCCGTTATTGCTGACCCAAGAGGTAACACTTTG<br>GGTAGAGGTACTACTATCACTTTGGTTTTGAAAGAAGAGGC<br>TTCCGACTACTTGGAGTTGGACACTATCAAGAACTTGGTTAA<br>GAAGTACTCCCAGTTCATCAACTTCCCAATCTATGTTTGGTC<br>CTCCAAGACTGAGACTGTTGAGGAACCAATGGAAGAAGAA<br>GAGGCTGCTAAAGAAGAGAAAGAGGAATCTGACGACGAGG<br>CTGCTGTTGAAGAAGAGGAAGAAGAAAAAGAAGCCAAAGAC<br>TAAGAAGGTTGAAAAGACTGTTTGGGACTGGGAGCTTATGA<br>ACGACATCAAGCCAATTTGGCAGAGACCATCCAAAGAGGTT<br>GAGGAGGACGAGTACAAGGCTTTCTACAAGTCCTTCTCCAA<br>AGAATCCGATGACCCAATGGCTTACATCCACTTCACTGCTG<br>AGGGTGAAGTTACTTTCAAGTCCATCTTGTTCGTTCCAACTT<br>CTGCTCCAAGAGGATTGTTCGACGAGTACGGTTCTAAGAAG<br>TCCGACTACATCAAACTTTATGTTAGAAGAGTTTTCATCACT<br>GACGACTTCCACGATATGATGCCAAAGTACTTGAACTTCGTT<br>AAGGGTGTTGTTGATTCCGATGACTTGCCATTGAACGTTTCC<br>AGAGAGACTTTGCAGCAGCACAAGTTGTTGAAGGTTATCAG<br>AAAGAAACTTGTTAGAAAGACTTTGGACATGATCAAGAAGA<br>TCGCTGACGACAAGTACAACGACACTTTCTGGAAAGAGTTC<br>GGAACTAACATCAAGTTGGGTGTTATTGAGGACCACTCCAA<br>CAGAACTAGATTGGCTAAGTTGTTGAGATTCCAGTCCTCTCA<br>TCACCCAACTGACATCACTTCCTTGGACCAGTACGTTGAGA<br>GAATGAAAGAAGCAGGACAAAATCTACTTCATGGCTGGT<br>TCCTCTAGAAAAGAGGCTGAATCCTCCCCATTCGTTGAGAG<br>ATTGTTGAAGAAGGGTTACGAGGTTATCTACTTGACTGAGC<br>CAGTTGACGAGTACTGTATCCAGGCTTTGCCAGAGTTTGAC<br>GGAAAGAGATTCCAGAACGTTGCTAAAGAGGGTGTTAAGTT<br>CGACGAATCCGAAAAGACTAAAGAATCCAGAGAGGCTGTT<br>GAGAAAGAGTTCGAGCCATTGTTGAACTGGATGAAGGACAA<br>GGCTTTGAAGGACAAGATCGAGAAGGCTGTTGTTTCCCAGA<br>GATTGACTGAATCCCCATGTGCTTTGGTTGCTTCCCAATACG<br>GATGGAGTGGTAACATGGAAAGAATCATGAAGGCTCAGGCT<br>TACCAAAACTGGAAAGGACATCTCCACTAACTACTACGCTTC |

TABLE 1-continued

BRIEF DESCRIPTION OF THE SEQUENCES

| SEQ ID NO: | Description | Sequence |
|---|---|---|
|  |  | CCAGAAGAAAACTTTCGAGATCAACCCAAGACACCCATTGA<br>TCAGAGACATGTTGAGAAGAATCAAAGAGGACGAGGACGA<br>CAAGACTGTTTTGGATTTGGCTGTTGTTTTGTTCGAGACTGC<br>TACTTTGAGATCCGGTTACTTGTTGCCAGACACTAAGGCTTA<br>CGGTGACAGAATCGAGAGAATGTTGAGATTGTCCTTGAACA<br>TTGACCCAGACGCTAAGGTTGAAGAAGAACCAGAAGAAGA<br>GCCAGAGGAAACTGCTGAAGATACTACTGAGGACACTGAAC<br>AAGACGAGGACGAAGAGATGGATGTTGGTACTGACGAAGA<br>GGAAGAGACAGCAAAGGAATCCACTGCTGAACACGACGAG<br>TTGTAA |
| 44 | human GRP94 Gene (protein) | DDEVDVDGTVEEDLGKSREGSRTDDEVVQREEEAIQLDGLNA<br>SQIRELREKSEKFAFQAEVNRMMKLIINSLYKNKEIFLRELISNA<br>SDALDKIRLISLTDENALSGNEELTVKIKCDKEKNLLHVTDTGV<br>GMTREELVKNLGTIAKSGTSEFLNKMTEAQEDGQSTSELIGQF<br>GVGFYSAFLVADKVIVTSKHNNDTQHIWESDSNEFSVIADPRG<br>NTLGRGTTITLVLKEEASDYLELDTIKNLVKKYSQFINFPIYVW<br>SSKTETVEEPMEEEEAAKEEKEESDDEAAVEEEEEEKKPKTKK<br>VEKTVWDWELMNDIKPIWQRPSKEVEEDEYKAFYKSFSKESD<br>DPMAYIHFTAEGEVTFKSILFVPTSAPRGLFDEYGSKKSDYIKL<br>YVRRVFITDDFHDMMPKYLNFVKGVVDSDDLPLNVSRETLQQ<br>HKLLKVIRKKLVRKTLDMIKKIADDKYNDTFWKEFGTNIKLGV<br>IEDHSNRTRLAKLLRFQSSHHPTDITSLDQYVERMKEKQDKIYF<br>MAGSSRKEAESSPFVERLLKKGYEVIYLTEPVDEYCIQALPEFD<br>GKRFQNVAKEGVKFDESEKTKESREAVEKEFEPLLNWMKDKA<br>LKDKIEKAVVSQRLTESPCALVASQYGWSGNMERIMKAQAYQ<br>TGKDISTNYYASQKKTFEINPRHPLIRDMLRRIKEDEDDKTVLD<br>LAVVLFETATLRSGYLLPDTKAYGDRIERMLRLSLNIDPDAKV<br>EEEPEEEPEETAEDTTEDTEQDEDEEMDVGTDEEEETAKESTAE<br>FIDEL |
| 45 | ProteinA fusion protein (apre-5xBD-Htag) as EcoRI/SalI fragment, including alpha MF pre signal sequence (underlined), 5 Fc binding domains, and a HA and 9 x HIS tag at the C-terminus. | GAATTCGAAACGATGAGATTCCCATCCATCTTCACTGCTGTT<br>TTGTTCGCTGCTTCTTCTGCTTTGGCGGCCGCTAATGCTGCTC<br>AACACGACGAAGCTCAACAGAACGCTTTCTACCAGGTTTTG<br>AACATGCCAAACTTGAACGCTGACCAGAGGAATGGTTTCAT<br>CCAGTCCTTGAAGGATGACCCATCTCAATCCGCTAACGTTTT<br>GGGTGAAGCTCAGAAGTTGAACGACAGTCAAGCTCCTAAGG<br>CTGATGCTAACAAAACAACTTCAACAAGGACCAGCAATCT<br>GCTTTCTACGAAATCTTGAATATGCCTAATTTGAACGAGGCT<br>CAGAGAAATGGATTCATCCAATCTTTGAAAGACGACCCATC<br>CCAGTCTACTAATGTTTTGGGAGAGGCTAAGAAACTTAATG<br>AAAGTCAGGCTCCTAAAGCTGACAACAACTTTAACAAAGAG<br>CAGCAGAACGCTTTTTATGAGATTCTTAACATGCCTAACTTG<br>AACGAAGAGCAAAGAAACGGTTTTATTCAATCATTGAAGGA<br>CGATCCTTCACAGTCTGCTAACTTGTTGTCCGAGGCTAAAAA<br>GTTGAACGAATCTCAGGCTCCTAAGGCTGATAATAAGTTCA<br>ACAAAGAACAACAAAATGCTTTCTACGAGATTTTGCACTTG<br>CCAAATTTGAATGAGGAACAGAGAAACGGTTTTATTCAGTC<br>ATTGAAGGATGACCCTTCCCAATCTGCTAATTTGTTGGCTGA<br>AGCTAAGAAATTGAACGACGCTCAGGCTCCAAAAGCTGATA<br>ACAAATTCAACAAAGAGCAACAGAACGCTTTCTACGAAATC<br>TTGCATTTGCCAAACTTGACAGAAGAGCAGAGAAACGGATT<br>CATTCAGTCTTTGAAGGATGACCCTTCCGTTTCCAAAGAGAT<br>TTTGGCTGAGGCTAAAAAGTTGAATGATGCTCAAGCTCCAA<br>AAGGTGGTGGTTACCCATACGATGTTCCAGATTACGCTGGA<br>GGTCATCATCATCACCACCATCACCATCATGGTGGTGTCGAC |
| 46 | Protein A fusion protein; alpha-MF-pre-signal is underlined | MRFPSIFTAVLFAASSALAAANAAQHDEAQQNAFYQVLNMPN<br>LNADQRNGFIQSLKDDPSQSANVLGEAQKLNDSQAPKADAQQ<br>NNFNKDQQSAFYEILNMPNLNEAQRNGFIQSLKDDPSQSTNVL<br>GEAKKLNESQAPKADNNFNKEQQNAFYEILNMPNLNEEQRNG<br>FIQSLKDDPSQSANLLSEAKKLNESQAPKADNKFNKEQQNAFY<br>EILHLPNLNEEQRNGFIQSLKDDPSQSANLLAEAKKLNDAQAP<br>KADNKFNKEQQNAFYEILHLPNLTEEQRNGFIQSLKDDPSVSK<br>EILAEAKKLNDAQAPKGGGYPYDVPDYAGGHHHHHHHHHGG<br>VD |
| 47 | alpha-amylase-ProtAZZ/up: | CGGAATTCacgatggtcgcttggtggtctttgtttctgtacggtcttcaggtcgctgca<br>cctgctttggctTCTGGTGGTGTTACTCCAGCTGCTAACGCTG<br>CTCAACACG |
| 48 | HA-ProtAZZ-XhoIZZ/lp: | GCCTCGAGAGCGTAGTCTGGAACATCGTATGGGTAACCACC<br>ACCAGCATC |

TABLE 1-continued

BRIEF DESCRIPTION OF THE SEQUENCES

| SEQ ID NO: | Description | Sequence |
|---|---|---|
| 49 | DNA sequence of the ZZ-domain as EcoRI/XhoI fragment: Alpha-amylase sequence underlined | GAATTCacgatggtcgcttggtggtattgtttctgtacggtcttcaggtcgctgcacct gattggctTCTGGTGGTGTTACTCCAGCTGCTAACGCTGCT CAACACGATGAAGCTGTTGACAACAAGTTCAACAAAG AGCAGCAGAACGCTTTCTACGAGATCTTGCACTTGCCA AACTTGAACGAAGAGCAAAGAAACGCTTTCATCCAGT CCTTGAAGGATGACCCATCTCAATCCGCTAACTTGTTG GCTGAGGCTAAGAAGTTGAACGACGCTCAAGCTCCAA AGGTCGACAATAAGTTTAACAAAGAACAACAAAATGC CTTCTACGAAATTCTGCATCTGCCCAACCTTAACGAGG AACAGAGAAACGCCTTCATTCAGAGTTTGAAGGACGA TCCTTCCCAGTCTGCTAATTTGCTTGCCGAAGCCAAGA AATTGAATGATGCCCAGGCTCCAAAAGTTGATGCTGGT GGTGGTTACCCATACGATGTTCCAGACTACGCTCTCGA G |
| 50 | Protein sequence of the ZZ-domain: Alpha-amylase leader is underlined | MVAWWSLFLYGLQVAAPALASGGVTPAANAAQHDEAV DNKFNKEQQNAFYEILHLPNLNEEQRNAFIQSLKDDPSQS ANLLAEAKKLNDAQAPKVDNKFNKEQQNAFYEILHLPN LNEEQRNAFIQSLKDDPSQSANLLAEAKKLNDAQAPKVD AGGGYPYDVPDYALE |
| 51 | 5Ecoapp: | AACGGAATTCATGAGATTTCCTTCAATTTTTAC |
| 52 | 3Htag Sal | CGATGTCGACGTGATGGTGATGGTGGTGATGATGATGACCA CC |
| 53 | DNA sequence of the FcRIII(LF) as EcoRI/SalI fragment: | GAATTCATGAGATTTCCTTCAATTTTTACTGCTGTTTTATTCG CAGCATCCTCCGCATTAGCTGCTCCAGTCAACACTACAACA GAAGATGAAACGGCACAAATTCCGGCTGAAGCTGTCATCGG TTACTCAGATTTAGAAGGGGATTTCGATGTTGCTGTTTTGCC ATTTTCCAACAGCACAAATAACGGGTTATTGTTTATAAATAC TACTATTGCCAGCATTGCTGCTAAAGAAGAAGGGGTATCTC TCGAGAAAAGAGCTGGAATGAGAACTGAGGACTTGCCAAA GGCTGTTGTTTTCTTGGAGCCACAGTGGTACAGAGTTTTGGA GAAGGATTCCGTTACTTTGAAGTGTCAGGGAGCTTACTCTCC AGAAGATAACTCCACTCAGTGGTTCCACAACGAATCCTTGA TTTCTTCTCAGGCTTCCTCCTACTTCATTGACGCTGCTACTGT TGACGATTCCGGTGAGTACAGATGTCAGACTAACTTGTCCA CTTTGTCCGACCCAGTTCAATTGGAGGTTCACATCGGTTGGT TGTTGTTGCAAGCTCCAAGATGGGTTTTCAAGGAGGAGGAC CCAATTCATTTGAGATGTCACTCTTGGAAGAACACTGCTTTG CACAAAGTTACTTACTTGCAGAACGGAAAGGGTAGAAAGTA TTTTCCACCACAACTCCGACTTCTACATCCCAAAGGCTACTTT GAAGGATTCCGGTTCCTACTTCTGTAGAGGATTGTTCGGTTC CAAGAACGTTTCTTCCGAGACTGTTAACATCACTATCACTCA GGGATTGGCTGTTTCCACTATCTCTTCCTTCTTCCCACCAGG TTATCAAGGTGGTGGTCATCATCATCACCACCATCACCATCA CGTCGAC |
| 54 | Protein sequence of the FcRIII(LF) with alpha MF pre signal sequence and HIS Tag: | MRFPSIFTAVLFAASSALAAPVNTTTEDETAQIPAEAVIGYSDLE GDFDVAVLPFSNSTNNGLLFINTTIASIAAKEEGVSLEKRAGMR TEDLPKAVVFLEPQWYRVLEKDSVTLKCQGAYSPEDNSTQWF HNESLISSQASSYFIDAATVDDSGEYRCQTNLSTLSDPVQLEVHI GWLLLQAPRWVFKEEDPIHLRCHSWKNTALHKVTYLQNGKG RKYFHHNSDFYIPKATLKDSGSYFCRGLFGSKNVSSETVNITIT QGLAVSTISSFFPPGYQGGGHHEIHHHHHHVD |
| 55 | DNA sequence of the FcRIas EcoRI/SalI fragment: | GAATTCATGAGATTTCCTTCAATTTTTACTGCTGTTTTATTCG CAGCATCCTCCGCATTAGCTGCTCCAGTCAACACTACAACA GAAGATGAAACGGCACAAATTCCGGCTGAAGCTGTCATCGG TTACTCAGATTTAGAAGGGGATTTCGATGTTGCTGTTTTGCC ATTTTCCAACAGCACAAATAACGGGTTATTGTTTATAAATAC TACTATTGCCAGCATTGCTGCTAAAGAAGAAGGGGTATCTC TCGAGAAAAGAGCTGATACTACTAAGGCTGTTATCACTTTG CAACCACCATGGGTTTCCGTTTTCCAGGAGGAGACTGTTACT TTGCACTGTGAGGTTTTGCATTTGCCTGGTTCCTCTTCCACTC AGTGGTTCTTGAACGGTACTGCTACTCAAACTTCCACTCCAT CCTACAGAATTACTTCCGCTTCCGTTAACGATTCTGGTGAGT ACAGATGTCAGAGAGGATTGTCTGGTAGATCCGACCCAATT CAGTTGGAGATTCACAGAGGATGGTTGTTGTTGCAGGTTTCC TCCAGAGTTTTCACTGAGGGTGAACCATTGGCTTTGAGATGT CACGCTTGGAAGGACAAGTTGGTTTACAACGTTTTGTACTAC AGAAACGGAAAGGCTTTCAAGTTCTTCCACTGGAACTCCAA |

TABLE 1-continued

BRIEF DESCRIPTION OF THE SEQUENCES

| SEQ ID NO: | Description | Sequence |
|---|---|---|
| | | CTTGACTATCTTGAAAACTAACATCTCCCACAACGGTACTTA<br>CCACTGTTCTGGAATGGGAAAGCACAGATACACTTCCGCTG<br>GTATCTCCGTTACTGTTAAGGAGTTGTTCCCAGCTCCAGTTT<br>TGAACGCTTCCGTTACTTCTCCATTGTTGGAGGGAAACTTGG<br>TTACTTTGTCCTGTGAGACTAAATTGTTGTTGCAAAGACCAG<br>GATTGCAGTTGTACTTCTCCTTCTACATGGGTTCCAAGACTT<br>TGAGAGGTAGAAACACTTCCTCCGAGTACCAAATCTTGACT<br>GCTAGAAGAGAGGATTCCGGTTTGTACTGGTGTGAAGCTGC<br>TACTGAGGACGGTAACGTTTTGAAGAGATCCCCAGAGTTGG<br>AGTTGCAAGTTTTGGGATTGCAATTGCCAACTCCAGGTGGT<br>GGTCATCATCATCACCACCATCACCATCACGTCGAC |
| 56 | Protein sequence of the FcRI with alpha MF pre signal sequence and HIS Tag: | MRFPSIFTAVLFAASSALAAPVNTTTEDETAQIPAEAVIGYSDLE<br>GDFDVAVLPFSNSTNNGLLFINTTIASIAAKEEGVSLEKRADTT<br>KAVITLQPPWVSVFQEETVTLHCEVLHLPGSSSTQWFLNGTAT<br>QTSTPSYRITSASVNDSGEYRCQRGLSGRSDPIQLEIHRGWLLL<br>QVSSRVFTEGEPLALRCHAWKDKLVYNVLYYRNGKAFKFFH<br>WNSNLTILKTNISHNGTYHCSGMGKHRYTSAGISVTVKELFPA<br>PVLNASVTSPLLEGNLVTLSCETKLLLQRPGLQLYFSFYMGSKT<br>LRGRNTSSEYQILTARREDSGLYWCEAATEDGNVLKRSPELEL<br>QVLGLQLPTPGGGHHEIHHHHHHVD |
| 57 | 5gutBglII: | ATTGAGATCTACCCAATTTAGCAGCCTGCATTCTC |
| 58 | 3 gutEcoRI: | GTCAGAATTCATCTGTGGTATAGTGTGAAAAAGTAG |
| 59 | DNA sequence GUT1 promoter | AGATCTACCCAATTTAGCAGCCTGCATTCTCTTGATTTTATG<br>GGGGAAACTAACAATAGTGTTGCCTTGATTTTAAGTGGCAT<br>TGTTCTTTGAAATCGAAATTGGGGATAACGTCATACCGAAA<br>GGTAAACAACTTCGGGGAATTGCCCTGGTTAAACATTTATT<br>AAGCGAGATAAATAGGGGATAGCGAGATAGGGGGCGGAGA<br>AGAAGAAGGGTGTTAAATTGCTGAAATCTCTCAATCTGGAA<br>GAAACGGAATAAATTAACTCCTTCCTGAGATAATAAGATCC<br>GACTCTGCTATGACCCCACACGGTACTGACCTCGGCATACC<br>CCATTGGATCTGGTGCGAAGCAACAGGTCCTGAAACCTTTA<br>TCACGTGTAGTAGATTGACCTTCCAGCAAAAAAGGCATTA<br>TATATTTTGTTGTTGAAGGGGTGAGGGGAGGTGCAGGTGGT<br>TCTTTTATTCGTCTTGTAGTTAATTTTCCCGGGGTTGCGGAG<br>CGTCAAAAGTTTGCCCGATCTGATAGCTTGCAAGATGCCAC<br>CGCTTATCCAACGCACTTCAGAGAGCTTGCCGTAGAAAGAA<br>CGTTTTCCTCGTAGTATTCCAGCACTTCATGGTGAAGTCGCT<br>ATTTCACCGAAGGGGGGGTATTAAGGTTGCGCACCCCCTCC<br>CCACACCCCAGAATCGTTTATTGGCTGGGTTCAATGGCGTTT<br>GAGTTAGCACATTTTTTCCTTAAACACCCTCCAAACACGGAT<br>AAAAATGCATGTGCATCCTGAAACTGGTAGAGATGCGTACT<br>CCGTGCTCCGATAATAACAGTGGTGTTGGGGTTGCTGTTAGC<br>TCACGCACTCCGTTTTTTTTCAACCAGCAAAATTCGATGGG<br>GAGAAACTTGGGGTACTTTGCCGACTCCTCCACCATACTGGT<br>ATATAAATAATACTCGCCCACTTTTCGTTTGCTGCTTTTATAT<br>TTCAAGGACTGAAAAAGACTCTTCTTCTACTTTTTCACACTA<br>TACCACAGATGAATTC |
| 60 | *S. cerevisiae* SED1 (without endogenous leader sequence | VDQFSNSTSASSTDVTSSSSISTSSGSVTITSSEAPESDNGT<br>STAAPTETSTEAPTTAIPTNGTSTEAPTTAIPTNGTSTEAPT<br>DTTTEAPTTALPTNGTSTEAPTDTTTEAPTTGLPTNGTTSA<br>FPPTTSLPPSNTTTTPPYNPSTDYTTDYTVVTEYTTYCPEP<br>TTFTTNGKTYTVTEPTTLTITDCPCTIEKPTTTSTTEYTVVT<br>EYTTYCPEPTTFTTNGKTYTVTEPTTLTITDCPCTIEKSEAP<br>ESSVPVTESKGTTTKETGVTTKQTTANPSLTVSTVVPVSS<br>SASSHSVVINSNGANVVVPGALGLAGVAMLFL |
| 61 | *S. cerevisiae* SED1 DNA sequence | GTCGACCAATTCTCTAACTCTACTTCCGCTTCCTCTACT<br>GACGTTACTTCCTCCTCCTCTATTTCTACTTCCTCCGGT<br>TCCGTTACTATTACTTCCTCTGAGGCTCCAGAATCTGAC<br>AACGGTACTTCTACTGCTGCTCCAACTGAAACTTCTAC<br>TGAGGCTCCTACTACTGCTATTCCAACTAACGGAACTT<br>CCACAGAGGCTCCAACAACAGCTATCCCTACAAACGG<br>TACATCCACTGAAGCTCCTACTGACACTACTACAGAAG<br>CTCCAACTACTGCTTTGCCTACTAATGGTACATCAACA<br>GAGGCTCCTACAGATACAACAACTGAAGCTCCAACAA<br>CTGGATTGCCAACAACGGTACTACTTCTGCTTTTCCCA<br>CCAACTACTTCCTTGCCACCATCCAACACTACTACTAC<br>TCCACCATACAACCCATCCACTGACTACACTACTGACT<br>ACACAGTTGTTACTGAGTACACTACTTACTGTCCAGAG |

TABLE 1-continued

BRIEF DESCRIPTION OF THE SEQUENCES

| SEQ ID NO: | Description | Sequence |
|---|---|---|
| | | CCAACTACTTTCACAACAAACGGAAAGACTTACACTGT |
| | | TACTGAGCCTACTACTTTGACTATCACTGACTGTCCAT |
| | | GTACTATCGAGAAGCCAACTACTACTTCCACTACAGAG |
| | | TATACTGTTGTTACAGAATACACAACATATTGTCCTGA |
| | | GCCAACAACATTCACTACTAATGGAAAAACATACACA |
| | | GTTACAGAACCAACTACATTGACAATTACAGATTGTCC |
| | | TTGTACAATTGAGAAGTCCGAGGCTCCTGAATCTTCTG |
| | | TTCCAGTTACTGAATCCAAGGGTACTACTACTAAAGAA |
| | | ACTGGTGTTACTACTAAGCAGACTACTGCTAACCCATC |
| | | CTTGACTGTTTCCACTGTTGTTCCAGTTTCTTCCTCTGC |
| | | TTCTTCCCACTCCGTTGTTATCAACTCCAACGGTGCTAA |
| | | CGTTGTTGTTCCTGGTGCTTTGGGATTGGCTGGTGTTGC |
| | | TATGTTGTTCTTGTAA |

What is claimed:

1. A method for producing yeast host cells that express an immunoglobulin of interest, comprising:
   a. providing yeast host cells that include a first nucleic acid molecule operably linked to a *Pichia pastoris* GUT1 promoter and which encodes a capture moiety comprising a Sed1p protein fused to protein A or ZZ-domain from Protein A integrated into the genome of the yeast host cells;
   b. transfecting the yeast host cells with a plurality of nucleic acid molecules encoding immunoglobulin heavy and light chains, wherein the nucleic acid molecules encoding the heavy chain and light chains are operably linked to a *Pichia pastoris* GAPDH promoter;
   c. (i) growing the yeast host cells under conditions that selectively induce expression of the *Pichia pastoris* GUT1 promoter to produce the capture moiety on the surface of the yeast host cells and (ii) growing the yeast host cells under conditions that selectively induce expression of the *Pichia pastoris* GAPDH promoter to produce yeast host cells in which the immunoglobulins expressed in the yeast host cells are secreted and captured by the capture moiety on the surface of the yeast host cells;
   d. contacting the yeast host cells with a detection means that specifically binds to the immunoglobulin of interest; and
   e. isolating yeast host cells in which the detection means is bound to the immunoglobulin of interest to produce the yeast host cells that express the immunoglobulin of interest.

2. The method of claim 1, wherein the yeast host cells are *Pichia pastoris* or *Saccharomyces cerevisiae*.

3. The method of claim 1, wherein the detection means is an antigen that is bound by the immunoglobulin of interest.

4. The method of claim 1, wherein the immunoglobulin is selected from the group consisting of: IgG1; IgG2; IgG3; IgG4; camel heavy chain; and llama heavy chain.

5. The method of claim 1, wherein the conditions in step c) (i) comprises growing the yeast host cells in growth media containing a first carbon source that selectively induces expression of the *Pichia pastoris* GUT1 promoter and in step c) (ii) comprises growing the yeast host cells in growth media containing a second carbon source that selectively induces the *Pichia pastoris* GAPDH promoter.

6. A method for presenting an immunoglobulin of interest on the surface of a yeast host cell, comprising:
   a. providing yeast host cells that include a first nucleic acid molecule operably linked to a *Pichia pastoris* GUT1 promoter and which encodes a capture moiety comprising a cell surface anchoring protein fused to protein A or ZZ-domain from Protein A integrated into the genome of the yeast host cells;
   b. transfecting the yeast host cells with a plurality of nucleic acid molecules encoding heavy chains and light chains of immunoglobulins wherein the nucleic acid molecules encoding the heavy and light chains are operably linked to a *Pichia pastoris* GAPDH promoter; and c. growing the yeast host cells under conditions wherein
(i) the *Pichia pastoris* GUT1 promoter is selectively induced to produce the capture moiety, so that the capture moiety is anchored to the surface of the yeast host cells prior to inducing expression of the immunoglobulin, and wherein
(ii) the *Pichia pastoris* GAPDH promoter is selectively induced to produce the heavy chains of the immunoglobulins while the *Pichia pastoris* GUT1 promoter is inhibited, wherein the immunoglobulins are secreted from the yeast host cells and bound by the capture moiety anchored to the surface of the yeast host cells.

7. The method of claim 6, further comprising:
d. contacting the yeast host cells of step (c) with a detection means that specifically binds to the immunoglobulin of interest; and
e. isolating the yeast host cells in which the detection means is bound to the immunoglobulin of interest to produce the yeast host cells that express the immunoglobulin of interest.

8. The method of claim 6, wherein the yeast host cells are *Pichia pastoris* or *Saccharomyces cerevisiae*.

9. The method of claim 6, wherein the immunoglobulin is selected from the group consisting of: IgG1; IgG2; IgG3; IgG4; camel heavy chain; and llama heavy chain.

10. A yeast host cell comprising a nucleic acid molecule encoding a Sed1p protein fused to protein A or ZZ-domain from Protein A operably linked to a *Pichia pastoris* GUT1 promoter integrated into the genome of the yeast host cell and nucleic acid molecules encoding the heavy and light chains of an immunoglobulin operably linked to a *Pichia pastoris* GAPDH promoter.

11. The yeast host cell of claim 10, wherein the yeast host cell is *Pichia pastoris* or *Saccharomyces cerevisiae*.

* * * * *